US011527324B2

(12) United States Patent
Pulitzer et al.

(10) Patent No.: US 11,527,324 B2
(45) Date of Patent: Dec. 13, 2022

(54) ARTIFICIAL INTELLIGENCE RESPONSE SYSTEM BASED ON TESTING WITH PARALLEL/SERIAL DUAL MICROFLUIDIC CHIP

(71) Applicant: RELIANT IMMUNE DIAGNOSTICS, INC., Austin, TX (US)

(72) Inventors: Jovan Hutton Pulitzer, Frisco, TX (US); Henry Joseph Legere, III, Austin, TX (US)

(73) Assignee: RELIANT IMMUNE DIAGNOSTICS, INC., Austin, TX (US)

( * ) Notice: Subject to any disclaimer, the term of this patent is extended or adjusted under 35 U.S.C. 154(b) by 1069 days.

(21) Appl. No.: 16/186,517

(22) Filed: Nov. 10, 2018

(65) Prior Publication Data

US 2019/0148013 A1 May 16, 2019

Related U.S. Application Data

(60) Provisional application No. 62/584,704, filed on Nov. 10, 2017.

(51) Int. Cl.
*G16H 50/20* (2018.01)
*G16H 10/60* (2018.01)
(Continued)

(52) U.S. Cl.
CPC ....... *G16H 50/20* (2018.01); *G06F 16/24568* (2019.01); *G06F 16/951* (2019.01);
(Continued)

(58) Field of Classification Search
CPC ........ G16H 50/20; G16H 10/60; G16H 20/10; G16H 80/00; G06F 16/24568;
(Continued)

(56) References Cited

U.S. PATENT DOCUMENTS 5,587,061 A 12/1996 Chen
5,709,788 A 1/1998 Chen
(Continued)

FOREIGN PATENT DOCUMENTS

CN 105954512 A 9/2016
EP 2404673 A1 11/2012
(Continued)

OTHER PUBLICATIONS

Jianjun Li et al. Application of Microfluidic Devices to Proteomics Research. Journal: Molecular & Cellular Proteomics Jan. 3, 2002. 1:157-168. Canada.
(Continued)

*Primary Examiner* — Hien L Duong
(74) *Attorney, Agent, or Firm* — Gregory M. Howison

(57) ABSTRACT

An artificial intelligence response system comprises a centralized system having associated therewith a trained database, a tends engine, and a plurality of patient records, a plurality of interconnected entities connected over a network to the centralized system, and a voice-activated assistant device connected over the network to the centralized system and to the interconnected entities, the voice-activated assistant device including a memory operatively coupled to a processor, wherein the processor is configured to receive medical information pertaining to a patient's health from the centralized system, request a treatment regimen for the patient from the centralized system, receive a voice command from a medical professional to retrieve additional medical information, request additional medical information in response to the voice command, and request one or more actions related to treating a patient.

20 Claims, 63 Drawing Sheets

(51) Int. Cl.
 G06N 3/04 (2006.01)
 G06N 3/08 (2006.01)
 G06F 16/951 (2019.01)
 G06F 16/2455 (2019.01)

(52) U.S. Cl.
 CPC .......... *G06N 3/0427* (2013.01); *G06N 3/084* (2013.01); *G16H 10/60* (2018.01)

(58) Field of Classification Search
 CPC .... G06F 16/951; G06N 3/0427; G06N 3/084; G06N 3/0481; Y02A 90/10
 See application file for complete search history.

(56) References Cited

U.S. PATENT DOCUMENTS

| | | | |
|---|---|---|---|
| 5,904,826 | A | 5/1999 | Chen |
| 6,077,684 | A | 6/2000 | Kravtsov |
| 6,083,682 | A | 7/2000 | Campbell et al. |
| 6,149,865 | A | 11/2000 | Hsu |
| 7,090,802 | B1 | 8/2006 | Wang |
| 7,235,098 | B2 | 6/2007 | Palmaz |
| 7,959,875 | B2 | 6/2011 | Zhou et al. |
| 8,308,452 | B2 | 11/2012 | Amirouche et al. |
| 8,506,901 | B2 | 8/2013 | Chen et al. |
| 8,655,009 | B2 | 2/2014 | Chen et al. |
| 8,807,169 | B2 | 8/2014 | Amirouche et al. |
| 8,877,140 | B2 | 11/2014 | Chen et al. |
| 8,911,679 | B2 | 12/2014 | Chen et al. |
| 9,285,323 | B2 | 3/2016 | Burg et al. |
| 9,347,595 | B2 | 5/2016 | Toner et al. |
| 9,390,237 | B2 | 6/2016 | Myers et al. |
| 9,523,358 | B2 | 12/2016 | Amirouche et al. |
| 9,569,858 | B2 | 2/2017 | Babcock et al. |
| 9,607,380 | B2 | 3/2017 | Burg et al. |
| 9,726,161 | B2 | 8/2017 | Kim et al. |
| 9,996,666 | B1* | 6/2018 | Wilson ................ G06F 16/9537 |
| 10,614,919 | B1* | 4/2020 | Yedwab ................ G16H 10/60 |
| 11,074,998 | B1* | 7/2021 | Liotta ................... G16H 40/60 |
| 2002/0134682 | A1 | 9/2002 | Chen |
| 2002/0187564 | A1 | 12/2002 | Chow et al. |
| 2003/0054425 | A1 | 3/2003 | Parce et al. |
| 2003/0207458 | A1 | 11/2003 | Sookbumroong |
| 2005/0266582 | A1 | 12/2005 | Modlin et al. |
| 2006/0014302 | A1 | 1/2006 | Martinez |
| 2006/0222567 | A1 | 10/2006 | Kloepfer et al. |
| 2006/0245933 | A1 | 11/2006 | Balch |
| 2008/0070599 | A1 | 3/2008 | Apodaca |
| 2008/0118397 | A1 | 5/2008 | Slowey |
| 2009/0138251 | A1 | 5/2009 | Bugrim et al. |
| 2009/0298191 | A1 | 12/2009 | Whitesides et al. |
| 2009/0299767 | A1 | 12/2009 | Michon et al. |
| 2011/0029326 | A1* | 2/2011 | Venon ................... G16H 15/00 705/3 |
| 2011/0077971 | A1 | 3/2011 | Surwit |
| 2011/0124515 | A1 | 5/2011 | Silver |
| 2011/0238039 | A1 | 9/2011 | Leonard et al. |
| 2011/0250585 | A1 | 10/2011 | Ingber et al. |
| 2012/0082598 | A1 | 4/2012 | Baydoun |
| 2012/0224053 | A1 | 9/2012 | Vykoukal et al. |
| 2013/0161190 | A1 | 6/2013 | Ewart et al. |
| 2013/0189794 | A1 | 7/2013 | Emeric et al. |
| 2013/0273528 | A1 | 10/2013 | Ehrenkranz |
| 2014/0051173 | A1 | 2/2014 | Barstis et al. |
| 2014/0072189 | A1 | 3/2014 | Jena |
| 2014/0089006 | A1 | 3/2014 | Abreu |
| 2014/0121487 | A1 | 5/2014 | Faybishenko et al. |
| 2014/0170679 | A1 | 6/2014 | Aitchison |
| 2015/0056719 | A1 | 2/2015 | Karlovac |
| 2015/0161330 | A1* | 6/2015 | Joao ........................ G16H 15/00 705/3 |
| 2015/0269342 | A1* | 9/2015 | Swagger ................ G16H 40/63 705/3 |
| 2015/0359458 | A1 | 12/2015 | Erickson et al. |
| 2016/0077091 | A1 | 3/2016 | Tyrrell et al. |
| 2016/0123857 | A1 | 5/2016 | Kapur et al. |
| 2016/0223536 | A1 | 8/2016 | Johnson et al. |
| 2016/0274020 | A1 | 9/2016 | Winkler et al. |
| 2016/0292385 | A1 | 10/2016 | Lekander et al. |
| 2016/0318019 | A1 | 11/2016 | Ledden et al. |
| 2017/0011193 | A1 | 1/2017 | Arshad et al. |
| 2017/0059566 | A1 | 3/2017 | Reed et al. |
| 2017/0089893 | A1 | 3/2017 | Legere, III |
| 2017/0137861 | A1 | 5/2017 | Elf et al. |
| 2018/0015455 | A1 | 1/2018 | Levner et al. |
| 2018/0060495 | A1* | 3/2018 | Mahapatra ............. G16H 50/50 |
| 2018/0336972 | A1* | 11/2018 | Carbonell .............. G06F 16/93 |
| 2019/0130066 | A1* | 5/2019 | Jaroch ................... G16H 10/60 |

FOREIGN PATENT DOCUMENTS

| | | |
|---|---|---|
| WO | 2010118124 A2 | 10/2010 |
| WO | 2013158504 A1 | 10/2013 |
| WO | 2015143309 A1 | 9/2015 |

OTHER PUBLICATIONS

Kling A. et. al. Electrochemical microfluidic platform for simultaneous multianalyte detection. Article, 2015, 916-919, Europe.
Andre Kling et al. Multianalyte Antibiotic Detection on an Electrochemical Microfluidic Platform. Article. Jul. 19, 2016, 10036-10043, Germany.
Meichei Wang Kadlec et. al. A Cell Phone-Based Microphotometric System for Rapid Antimicrobial Susceptibility Testing. Journal. 2014, vol. 19 (3) 258-266. Tucson, AZ.
Hongying Zhu et al. Cost-effective and compact wide-field fluorescent imaging on a cell-phone. Article. Jan. 21, 2011. 315-322, 11(2). California.
Moffitt Jeffrey R. et al. The single-cell chemostat: an agarose-based, microfluidic device for high-throughput, single-cell studies of bacteria and bacterial communities. Article. Oct. 24, 2017. 21pgs. 12(8).
Temiz Yuksel et al. Microelectronic Engineering. Article. 2015. 156-175. Published by Elsevier B.V. Switzerland.
Vasdekis Andreas et al. Review of methods to probe single cell metabolism and bioenergetics, Journal, Jan. 1, 2015. 115-135. Published by Elsevier.
Wang Shuqi et al. Portable microfluidic chip for detection of *Escherichia coli* produce and blood. International Journal of Nanomedicine. May 27, 2012. 2012:7 2591-2600. MA.
Hoylandm James Donaldson. Microfluidic chip and connector. Nov. 11, 2012, 16pgs. Europe.
Baltekin Ozden et al. Antibiotic susceptibility testing in less than 30 min using direct single-cell imaging. Aug. 22, 2017. 9170-9175 vol. 114-34.
Ashraf Muhammad Waseem. Micro Electromechanical Systems (MEMS) Based Microfluidic Devices for Biomedical Applications. Journal : Molecular Sciences. Jun. 7, 2011. 3648-3704.
U. Hassan et al, A microfluidic biochip for complete blood cell counts at the point-of-care, Dec. 2015, 201-213, 3(4).
Au K. Anthony et al, Microvalves and Micropumps for BioMEMS, May 24, 2011, 179-220.
Sticker Drago et al, Multi-layered, membrane-integrated microfluidics based on replica molding of a thiol-ene epoxy thermoset for . . . Article, Nov. 2015, 4542-4554.
Shaegh et al, Plug-and-play microvalve and micropump for rapid integration with microfluidic chips, Article, Apr. 22, 2015, 557-564, Massachusetts, Springer Berlin Heidelberg.
Schafer Dawn et al, Microfluidic cell counter with embedded optical fibers fabricated by femtosecond laser ablation and anodic bonding, Article, Apr. 13, 2009, 17(8), 6068-6073, Colorado.
Hassan U. et al, A microfluidic biochip for complete blood cell counts at the point-of-care, Dec. 2015, 201-213. 3(4).
PCT: International Search Report and Written Opinion of PCT/US2018/060228 (related application); dated Mar. 22, 2019; 17pgs.
Kim et al, A programmable microfluidic cell array for combinatorial drug screening, 2012, Lab Chip, 12, 1813-1822 (Year: 2012).

(56) References Cited

OTHER PUBLICATIONS

Heo, J. Hua, S. Z. An Overview of Recent Strategies in Pathogen Sensing. Sensors 2009, 9, 4483-4502; doi:10.3390/s90604483.
Schafer, D. et al. Microfluidic cell counter with embedded optical fibers fabricated by femtosecond laser ablation and anodic bonding. Opt Express. Author manuscript; available in PMC Aug. 12, 2011. Published in final edited form as: Opt Express. Apr. 13, 2009; 17(8): 6068-6073.
Shaegh, S .A. M. et al. Plug-and-Play Microvalve and Micropump for Rapid Integration with Microfluidic Chips. Microfluid Nanofluid 19, No. 3 (Apr. 22, 2015): 557-564.
Sticker, D. et al. Multi-layered, membrane-integrated microfluidics based on replica molding of a thiol-ene epoxy thermoset for organ-on-a-chip applications. Lab Chip, 2015, 15, 4542.
Xu, A. K. et al. Microvalves and Micropumps for BioMEMS. Micromachines 2011, 2, 179-220; doi:10.3390/mi2020179.
Kling, A. et al. Multianalyte Antibiotic Detection on an Electrochemical Microfluidic Platform. Analytical Chemistry 2016, 88. Supporting Information.
Hassan, U. A microfluidic biochip for complete blood cell counts at the point-of-care. Technology (Singap World Sci). Author manuscript; available in PMC Feb. 21, 2016. Published in final edited form as: Technology (Singap World Sci). Dec. 2015 ; 3(4): 201-213. doi:10.1142/S2339547815500090.
Ashraf, M. W. Micro Electromechanical Systems (MEMS) Based Microfluidic Devices for Biomedical Applications. Int. J. Mol. Sci. 2011, 12, 3648-4704; doi:10.3390/ijms12063648.
Wang, S. et al. Portable microfluidic chip for detection of *Escherichia coli* in product and blood. International Journal of Nanomedicine, May 27, 2012.
Li, J. et al. Application of Microfluidic Devices to Proteomics Research. The American Society for Biochemistry and Molecular Biology, Inc. Feb. 1, 2002. http://www.mcponline.org/content/mcprot/1/2/157.full.pdf.
Abadian, P. N., Goluch, E. D. Surface Plasmon Resonance Imaging (SPRi) for Multiplexed Evaluation of Bacterial Adhesion onto Surface Coatings. Analytical Methods, Issue 1; 2015. Department of Chemical Engineering, Northeastern University, Boston, MA.
Kling, A. et al. Electrochemical microfluidic platform for simultaneous multi-analyte detection. Procedia Engineering 120; 2015. pp. 916-919.
Kling, A. et al. Multianalyte Antibiotic Detection on an Electrochemical Microfluidic Platform. Analytical Chemistry 2016, 88.
Mercier, M. Microfluidic Continuous Flow Cell Counting and Concentration. Instituto Superior Tecnico, Av. 2007.
Kadlec, M.W. et al. A Cell Phone-Based Microphotometric System for Rapid Antimicrobial Susceptibility Testing. Journal of Laboratory Automation, vol. 19(3), 258-266; 2014.
Zhu, H. et al. Cost-Effective and compact wide-field fluorescent imaging on a cell-phone. Lab Chip, Jan. 21, 2011; 11(2): 315-322.
Moffitt, Jeffrey R., Jeffrey B. Lee, and Philippe Cluzel. 2012. "The Single-Cell Chemostat: An Agarose-Based, Microfluidic Device for High-Throughput, Single-Cell Studies of Bacteria and Bacterial Communities." Lab Chip 12 (8): 1487.
Temiz, Y. et al. Lab-on-a-chip devices: How to close and plug the lab? Microelectronic Engineering 132 (2015) 156-175.
Vasdekis, A. E., Stephanopoulos, G. Review of methods to probe single cell metabolism and bioenergetics. Metab Eng. Author manuscript; available in PMC Apr. 16, 2015. Published in final edited form as: Metab Eng. Jan. 2015 ; 27: 115-135. doi:10.1016/j.ymben.2014.09.007.
Brown, M. C. et al. (2009). Lateral Flow Immunoassay. Tse, H. Y., Wong, R. C. (Eds.). New York, NY: Humana Press.
Baltekin, O., et al. (Aug. 22, 2017) Antibiotic susceptibility testing in less than 30 min using direct single-cell imaging. Proceedings of the National Academy of Sciences. 114(34).
Mudanyali, O. et al. Integrated Rapid-Diagnostic-Test Reader Platform on a Cellphone. Lab on a Chip, vol. 12, No. 15. Aug. 7, 2012; pp. 7, 12.
FisherSCI. Anti-Zika virus ELISA (IgM) test instruction. Sep. 2, 2016.
Acharya, D. et al. An ultrasensitive electrogenerated chemiluminescence-based immunoassay for specific detection of Zika virus. Scientific Reports 6, Article No. 32227. Aug. 2016.
International Search Report and Written Opinion of the International Searching Authority from PCT/US17/57037, dated Dec. 28, 2017.
International Search Report and Written Opinion of the International Searching Authority from PCT/US17/57039, dated Dec. 26, 2017.
International Search Report and Written Opinion of the International Searching Authority from PCT/US17/57041, dated Dec. 14, 2017.
International Search Report and Written Opinion of the International Searching Authority from PCT/US17/60252, dated Jan. 12, 2018.
International Search Report and Written Opinion of the International Searching Authority from PCT/US17/66528, dated Mar. 7, 2018.

\* cited by examiner

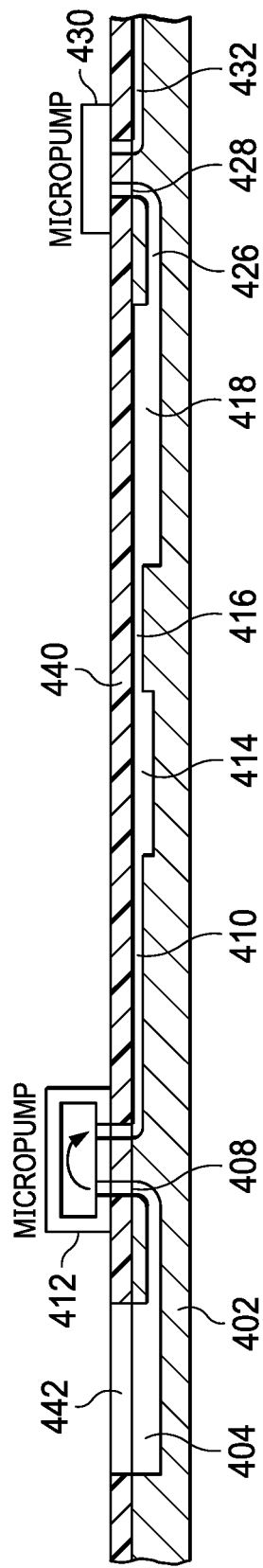

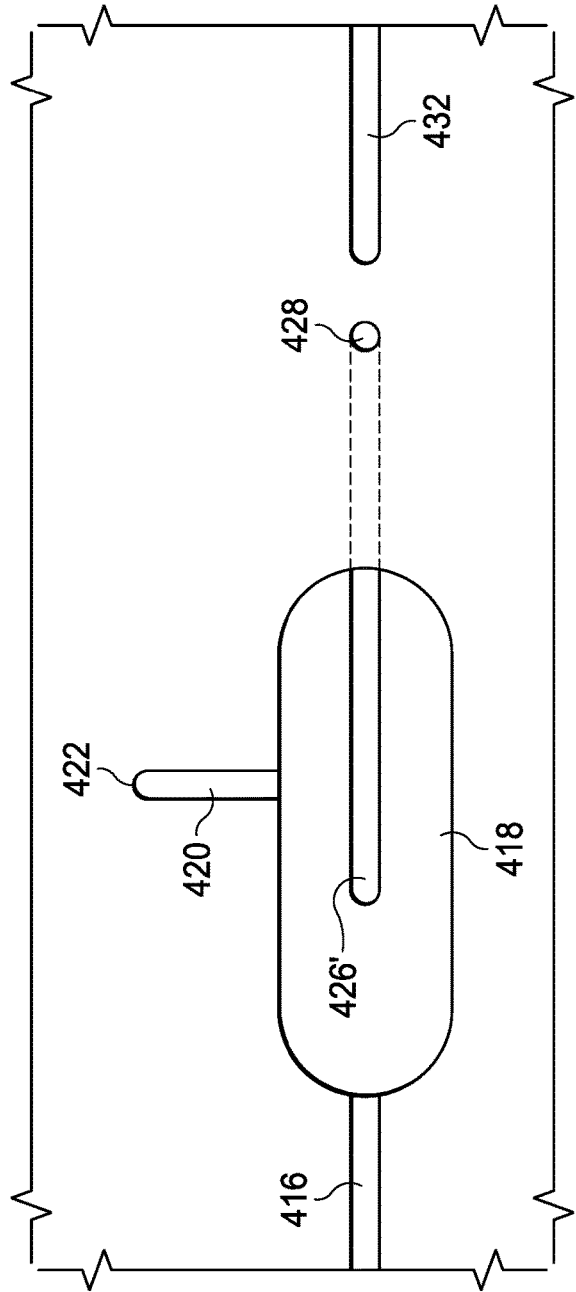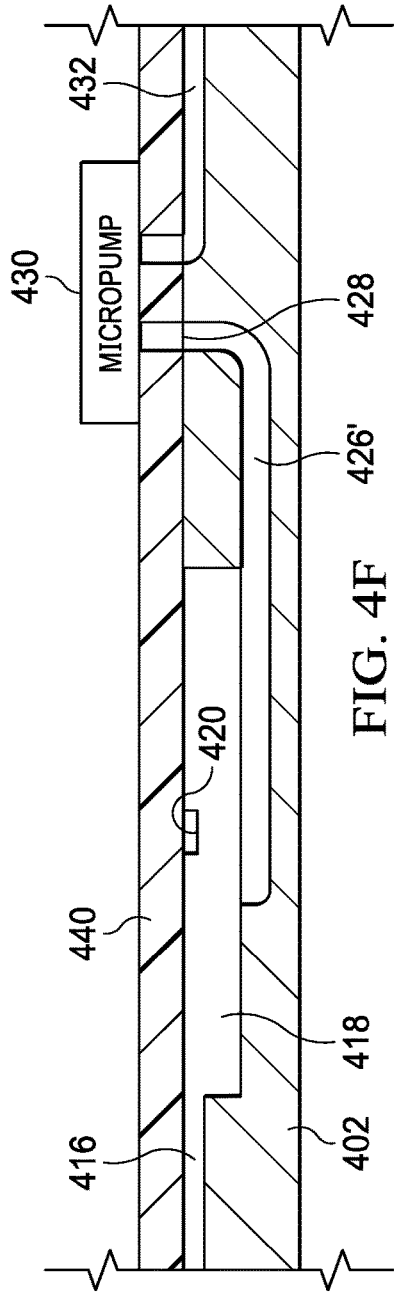

TID (TEST I.D.)

UDID (UNIQUE DEVICE I.D.)

SOID (SELF/OTHER I.D.)

| TEST RATING | HEALTH RISK | MEDICAL INTERVENTION TYPE |
|---|---|---|
| 76+ | DEADLY | EMERGENCY |
| 51-75 | DANGEROUS | URGENT |
| 26-50 | ELEVATED | NONE |
| 0-25 | NORMAL | NONE |

| UNIQUE I.D. # XXXXX | |
|---|---|
| NAME | JOHN DOE |
| BIOLOGIC | 2402 |
| BIOLOGIC | 6743 |
| DOCTOR | M. FRANKLIN |
| PHARMACY | MEDCO |

| BIOLOGIC ID # 2402 | |
|---|---|
| BIOLOGIC TYPE | BLOOD |
| PREGNANCY RATING | 99 |
| ZIKA INFECTION RATING | 75 |
| GLUCOSE RATING | 10 |

| TEST I.D. #10 ||
|---|---|
| TEST DATE | 11/5/2015 |
| BIOLOGIC TYPE | SALIVA |
| TEST TYPE | STREPTOCOCCAL |
| INFECTION STATUS | Y |
| EFFECTIVE TREATMENT | DOSE OF AMOXICILLIN |
| EFFECTIVE TREATMENT DOSAGE | 250 mg |
| TREATMENT PLAN | ADMINISTER TREATMENT AT EFFECTIVE DOSE EVERY 12 HOURS FOR 2 WEEKS |

4302

| PATIENT ID #1002 ||
|---|---|
| TEST I.D. | 10 |
| TEST I.D. | 11 |
| TEST I.D. | 12 |
| PRIMARY CARE PHYSICIAN | M. FRANKLIN |
| . | |
| . | |
| . | |
| INSURANCE INFORMATION | MEDCO |

FIG. 43

| HAPLOGROUP C | 4704 |
|---|---|
| TEST I.D. # 10 | 10720 |
| TEST I.D. # 11 | 2 |
| TEST I.D. #12 | 450 |
| . | |
| . | |
| . | |

| PATIENT ID #1002 | 4702 |
|---|---|
| TEST I.D. | 10 |
| TEST I.D. | 11 |
| TEST I.D. | 12 |
| PRIMARY CARE PHYSICIAN | M. FRANKLIN |
| HAPLOGROUP | C |
| TRENDING SUSCEPTABILITY | PROSTATE CANCER |
| . | |
| . | |

FIG. 47

ARTIFICIAL INTELLIGENCE RESPONSE SYSTEM BASED ON TESTING WITH PARALLEL/SERIAL DUAL MICROFLUIDIC CHIP

CROSS-REFERENCE TO RELATED APPLICATIONS

This applications claims priority to and the benefit of U.S. Provisional Application No. 62/584,704, filed Nov. 10, 2017, and entitled ARTIFICIAL INTELLIGENCE RESPONSE SYSTEM BASED ON TESTING WITH PARALLEL/SERIAL DUAL MICROFLUIDIC CHIP, the contents of which are incorporated by reference herein in their entirety.

TECHNICAL FIELD

The following disclosure relates to a system connecting various participants in a medical system to exchange information regarding research and test results.

BACKGROUND

The emergence and spread of antibiotic-resistant bacteria are aggravated by incorrect prescription and use of antibiotics. Courts have this problem is the fact that there is no sufficiently fast diagnostic test to guide correct antibiotic prescription at the point of care. Currently, some fluid sample is retrieved from a patient and forwarded to a lab for testing to determine a specific treatment regimen. As a safeguard, the patient is sometimes initially given large doses of a general antibiotic until a more specific antibiotic can be determined to target the specific bacteria. This can take upwards of two or three days, as the process requires growing the bacteria in some culture medium and observing its response to various antibiotics.

SUMMARY

In one aspect thereof, an artificial intelligence response system is provided. The system comprises a centralized system having associated therewith a trained database, a tends engine, and a plurality of patient records, a plurality of interconnected entities connected over a network to the centralized system, and a voice-activated assistant device connected over the network to the centralized system and to the interconnected entities, the voice-activated assistant device including a memory operatively coupled to a processor, wherein the processor is configured to receive medical information pertaining to a patient's health from the centralized system, request a treatment regimen for the patient from the centralized system, receive a voice command from a medical professional to retrieve additional medical information, request additional medical information in response to the voice command, and request one or more actions related to treating a patient.

BRIEF DESCRIPTION OF THE DRAWINGS

For a more complete understanding, reference is now made to the following description taken in conjunction with the accompanying Drawings in which:

FIGS. 4A-4G illustrates detailed views of the first viewing stage;

FIGS. 28A-28H illustrate multiple views of a diagram of the microfluidic chip in schematic form and various loading and analysis steps associated there with;

FIG. 39 illustrates an example of a unique biologic ID database table;

FIG. 43 illustrates information that may be recorded in a patient record;

FIG. 47 illustrates one embodiment of database tables showing a particular trend;

DETAILED DESCRIPTION

Figure 1:
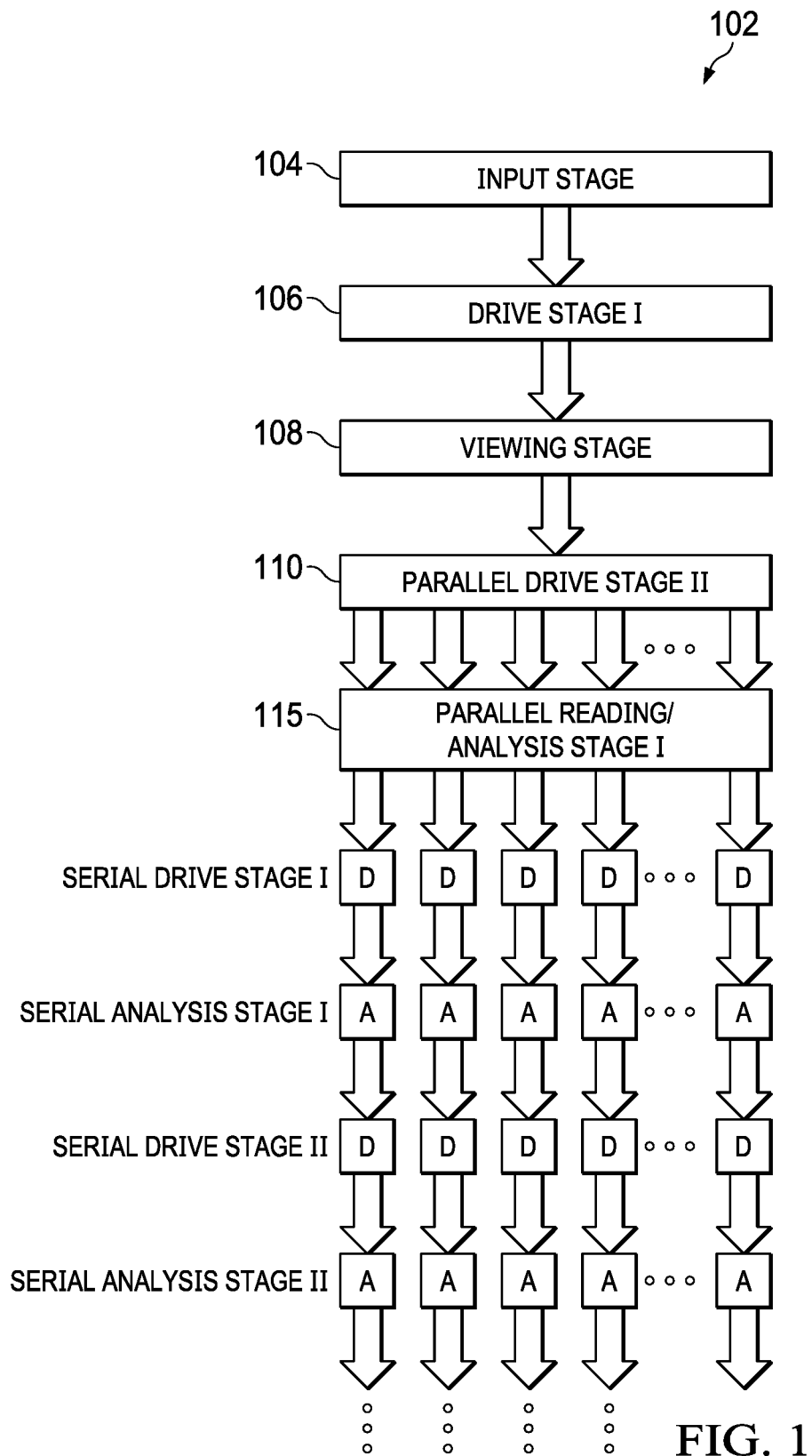
FIG. 1 illustrates a high-level view of a microfluidics chip of the present disclosure.

Referring now to the drawings, wherein like reference numbers are used herein to designate like elements throughout, the various views and embodiments of a microfluidic testing system with cell capture/analysis regions for processing a parallel and serial manner is illustrated and described, and other possible embodiments are described. The figures are not necessarily drawn to scale, and in some instances the drawings have been exaggerated and/or simplified in places for illustrative purposes only. One of ordinary skill in the art will appreciate the many possible applications and variations based on the following examples of possible embodiments.

Referring now to FIG. 1, there is illustrated a diagrammatic view of a microfluidics chip 102 at a high-level view. There is provided in the microfluidics chip 102 an input stage 104 that is operable to receive a biological specimen. As used herein, a "sample" must be capable of flowing through microfluidic channels of the system embodiments described hereinbelow. Thus, any sample consisting of a fluid suspension, or any sample that be put into the form of a fluid suspension, that can be driven through microfluidic channels can be used in the systems and methods described herein. For example, a sample can be obtained from an animal, water source, food, soil, air, etc. If a solid sample is obtained, such as a tissue sample or soil sample, the solid sample can be liquefied or solubilized prior to subsequent introduction into the system. If a gas sample is obtained, it may be liquefied or solubilized as well. The sample may also include a liquid as the particle. For example, the sample may consist of bubbles of oil or other kinds of liquids as the particles suspended in an aqueous solution.

Any number of samples can be introduced into the system for analysis and testing, and should not be limited to those samples described herein. A sample can generally include any suspensions, liquids, and/or fluids having at least one type of particle, cellular, droplet, or otherwise, disposed therein. In some embodiments, a sample can be derived from an animal such as a mammal. In a preferred embodiment, the mammal can be a human. Exemplary fluid samples derived from an animal can include, but are not limited to, whole blood, sweat, tears, ear flow, sputum, bone marrow suspension, lymph, urine, brain fluid, cerebrospinal fluid, saliva, mucous, vaginal fluid, ascites, milk, secretions of the respiratory, intestinal and genitourinary tracts, and amniotic fluid. In other embodiments, exemplary samples can include fluids that are introduced into a human body and then removed again for analysis, including all forms of lavage such as antiseptic, bronchoalveolar, gastric, peritoneal, cervical, athroscopic, ductal, nasal, and ear lavages. Exemplary particles can include any particles contained within the fluids noted herein and can be both rigid and deformable. In particular, particles can include, but are not limited to, cells, alive or fixed, such as adult red blood cells, fetal red blood cells, trophoblasts, fetal fibroblasts, white blood cells, epithelial cells, tumor cells, cancer cells, hematopoeitic stem cells, bacterial cells, mammalian cells, protists, plant cells, neutrophils, T lymphocytes, CD4+, B lymphocytes, monocytes, eosinophils, natural killers, basophils, dendritic cells, circulating endothelial, antigen specific T-cells, and fungal cells; beads; viruses; organelles; droplets; liposomes; nanoparticles; and/or molecular complexes. In some embodiments, one or more particles such as cells, may stick, group, or clump together within a sample.

In some embodiments, a fluid sample obtained from an animal is directly applied to the system described herein at the input stage, while in other embodiments, the sample is pretreated or processed prior to being delivered to a system. For example, a fluid drawn from an animal can be treated with one or more reagents prior to delivery to the system or it can be collected into a container that is preloaded with such a reagent. Exemplary reagents can include, but are not limited to, a stabilizing reagent, a preservative, a fixant, a lysing reagent, a diluent, an anti-apoptotic reagent, an anti-coagulation reagent, an anti-thrombotic reagent, magnetic or electric property regulating reagents, a size altering reagent, a buffering reagent, an osmolality regulating reagent, a pH regulating reagent, and/or a cross-linking agent.

At this point in the process, a finite amount of biofluids is disposed in the reservoir ready for transferring to subsequent stages. This amount of fluid is then transferred to another stage via a driving stage 106 in order to transfer this biofluid to another reservoir, that associated with a viewing stage 108. At this stage, a technician can examine the biofluid and determine the makeup of the biofluid, discriminate cells, etc. in order to make certain decisions as to going forward with remaining tests. The microfluidic chip then transfers the biofluid at the viewing stage 108 to a parallel analysis stage 115 through a parallel driving stage 110 wherein the biofluid is divided among a plurality of parallel path this for analysis of the reaction of the material in the biofluid with different reagents in a reading. This requires a certain amount of the biofluid to be transferred to this analysis stage. Thereafter, a decision is made as to whether to transfer the remaining biofluid from the viewing stage 108, in order to perform more testing and/or analysis on the biofluid. At this stage the process, only one of the multiple second stage or serial stage path is selected. One reason for this is that there is only a finite amount of biofluid available and there is no need for testing along paths that are associated with previous decisions indicating that the results will be negative along these paths. Each of these serial passes associated with one of the parallel paths. Thus, if there are five parallel paths, there will be five serial paths. Note that the term "serial path" is a term meaning that it is within the serial decision tree and it need not actually be a plurality of serial paths that are linked together in a serial manner, although they could be and are in some embodiments described hereinbelow. It is necessary to perform the testing/analysis along each of the five parallel paths, but a decision at this point indicates that only one of the serial paths will be required for the testing/analysis purpose. This will be described in more detail hereinbelow.

Figure 2A:
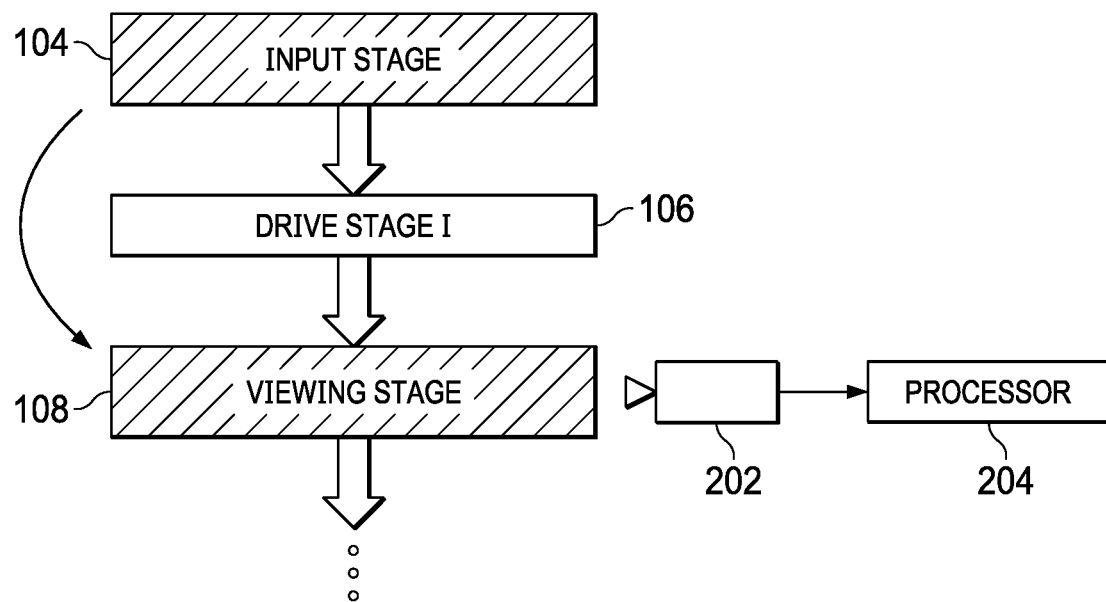
FIGS. 2A-2C illustrate detailed views of the multiple stages of analysis provided by the microfluidics chip of FIG. 1.
Figure 2B:
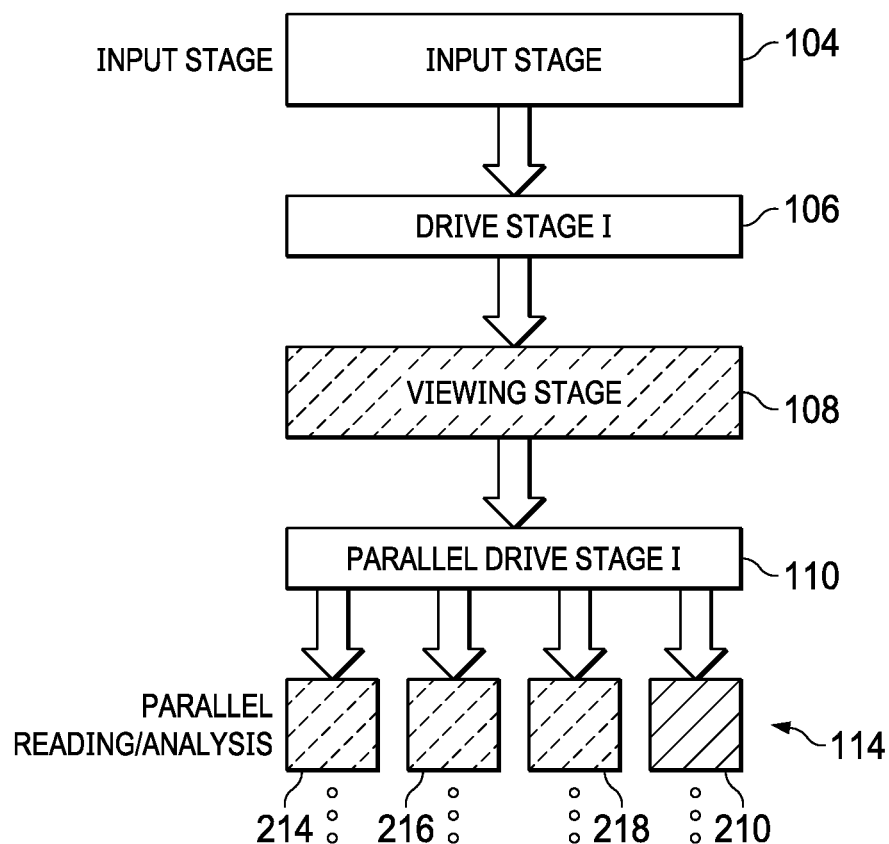
Figure 2C:
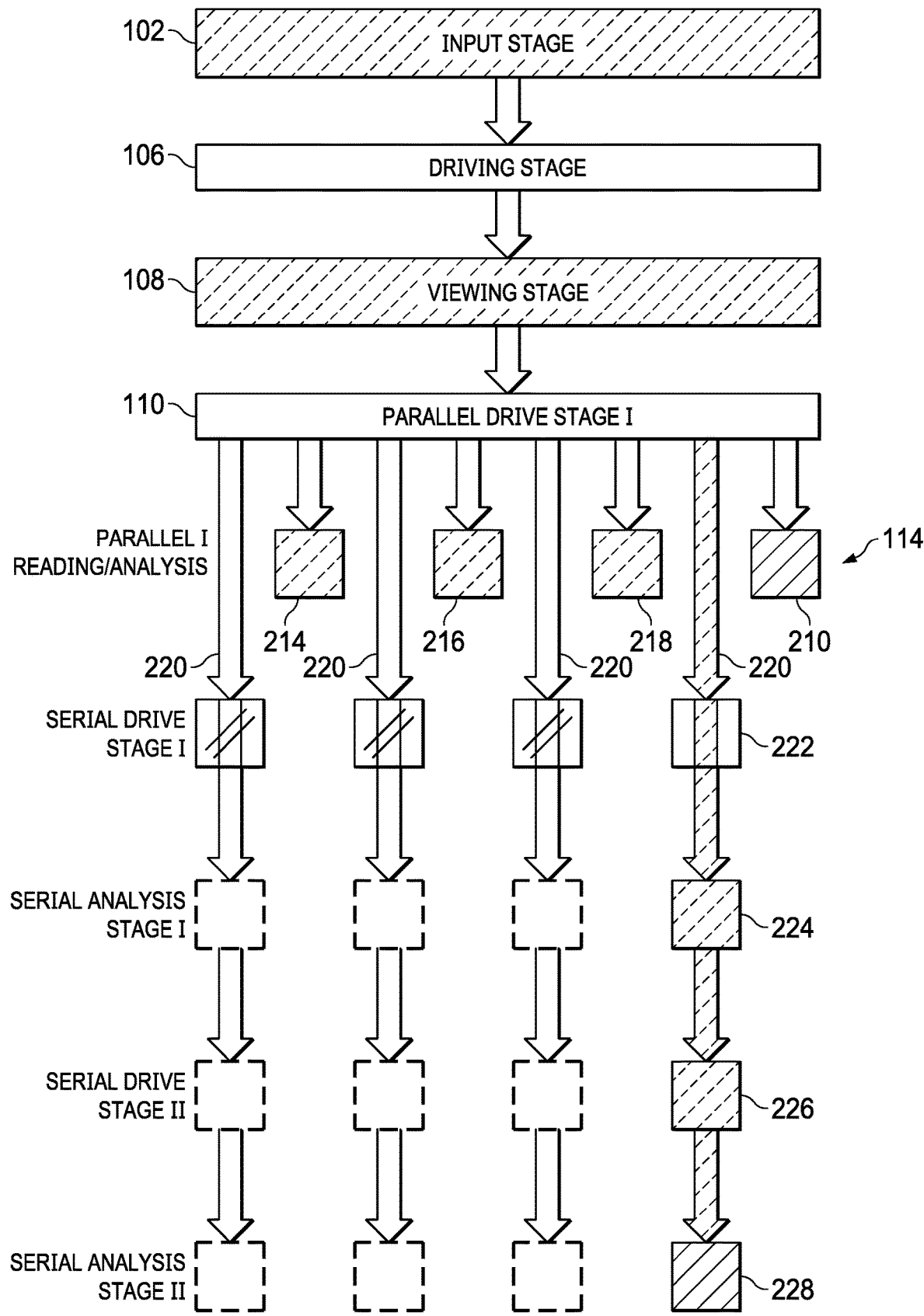

Referring now to FIGS. 2A-2C, there are illustrated diagrammatic views of the various stages of the process. With specific reference to FIG. 2A, there is illustrated a diagrammatic view of first viewing stage, wherein the amount of biofluid stored in the input stage reservoir 104 is driven to the viewing stage 108 reservoir. At this stage, optical device 202, for example, can be used to view the cells disposed within the medium. This medium could actually be the actual biofluid that was provided in the sample from the human/animal or could be some diluted version thereof. However, this biofluid will contain some cellular material or some particulate of interest. This can be viewed with the out device 202 and then passed to a processor 204, or a human could analyze the results. With utilization of the processor 204, the actual form of biofluid, and analog form, is transferred to a digital form. This could be in the form of cell counting for verification of a particular cell. As will be described hereinbelow, affinity labels can be associated with each of the cells or particulates in the biofluid and this could facilitate visual recognition of different characteristics or different types of cells, such as proteins, bacteria, etc. Each of these cellular materials can have a particular affinity label associated there with that allows it to be visually identified via some characteristics such as florescence or even magnetic properties associated with the affinity label. Again, this will be described hereinbelow. Although an optical device 202 was illustrated and described, any other type of device for analyzing the characteristics of a particular affinity labeled cell can be utilized, such as some type of magnetometer, etc.

Referring now to FIG. 2B, there is illustrated the next parallel drive stage. At this stage, a micropump is utilized in the parallel drive stage 110 to pump at least a portion of the biofluid stored in the reservoir associated with the viewing stage 108 is transferred to all of the parallel reading/analysis paths. In this step, it can be seen that a portion of the biofluid in the reservoir associated with the viewing stage 108 and is biofluid exists in each of these parallel paths for analysis. There is an indication in one of these parallel paths, associated with the reservoir 210, that shows a positive indication of a reaction of some type that is viewable. If, for example, this were bacteria, one reagent could be an antibiotic in a large dosage that would destroy the particular target bacteria and this would be recognized by an observer. The other three paths, associated with reservoirs 214, 216 and 218 (an example of 4 paths), would have no reaction and, as such, would not have affected the bacteria associated therewith. In this example, a high level of concentrated antibiotic is provided that would destroy the bacteria, but at this level of analysis, there is no indication provided as to the actual dosage of that antibiotic that would destroy the bacteria, other than the fact that a large dosage of this particular antibiotic will destroy the target bacteria. It is important to keep in mind that this particular biofluid may have multiple and different bacteria, proteins, etc. contained therein.

Referring now to FIG. 2C, there is illustrated a diagrammatic view of the final serial stage of analysis/testing. Since the first stage of testing/analysis transferred some of the biofluid from the viewing stage 108 to the parallel stages 114, there is still some biofluid remaining in the viewing stage 108. This is a selectively transferred to one of the serial paths, that associated with the testing reservoir 210. There are provided a plurality of bypass channels 220 associated with each of the serial paths and only the bypass channel 220 associated with the reservoir 210 in the parallel path 114 will be selected for transferring biofluid to this particular serial path associated with the reservoir 210 for testing. It will first be pumped to be a micropump in a serial drive stage 222 to a first serial reservoir 224 for testing/analysis. If the test is negative, it can then be passed to a subsequent serial driving stage 226 to a subsequent serial reservoir 228 for testing/analysis and so on. As will be described hereinbelow, there can be provided a single bypass path 220 which is connected to a manifold associated with each of the serial paths and each of the manifolds can be associated with each of the different reservoirs for testing, i.e., at this point the testing is parallel to all of the subsequent testing reservoirs. In the mode illustrated in this FIG. 2C, it is necessary to transfer all of the necessary biofluid, i.e., typically the remaining biofluid in the viewing stage reservoir 108, to the reservoir 224 and pass all of that biofluid to the next reservoir 228 and so on. Thus, at each stage, all of the biofluid transferred in the subsequent stages is tested at each subsequent stage. In a parallel configuration, the remaining biofluid in the viewing stage 108 would be required to be divided among the different testing reservoirs at each of the subsequent stages. This will be described in more detail hereinbelow.

Figure 3A:
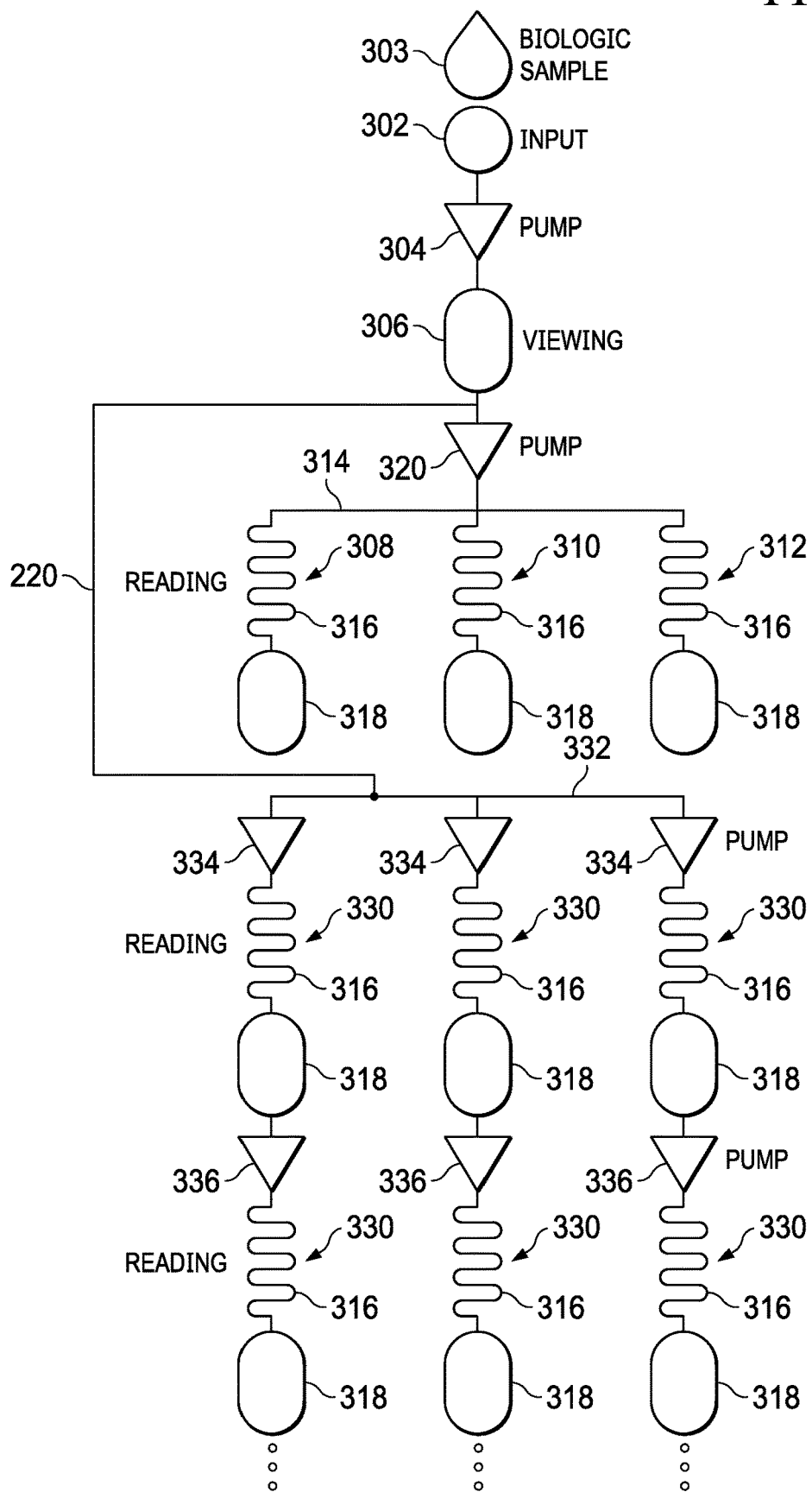
FIGS. 3A-3D illustrate diagrammatic views of the various cell capture regions and the interspersed pumps for the microfluidics chip of FIG. 1.

Referring now to FIGS. 3A-3D, there are illustrated diagrammatic views of the process and fluid flow. In FIG. 3A come there is illustrated an overall process flow for the embodiment described hereinabove. This embodiment, there is provided an input well 302 for receiving the biologic sample indicated by numeral 303. This constitutes a finite volume that must be transferred via a micropump to a viewing reservoir 306. At this point, substantially all of the biofluid is transferred from the reservoir 302 to the viewing reservoir 306. This is the first stage of the process. The second stage of the process is illustrated as providing three separate testing reservoirs 308, 310, 312, attached at one to a microchannel manifold 314. Each of the testing reservoirs 308, 310, 312, as will be described hereinbelow, is comprised of a serpentine microchannel 316 attached at one end to the manifold 314 and at the other end to a viewing reservoir 318. A micropump 320 is provided for transferring biofluid from the viewing reservoir 306 to the manifold 314. This will be divided among the three testing reservoirs 308, 310, 312 and substantially even amounts. The biofluid will traverse the serpentine microchannel 316, which is coated with a particular reagent, one example being an antibiotic. In this example, the antibiotic is at a very high concentrated level, each of the testing reservoirs 308, 310 and 312 having a different antibiotic associated there with. Only a portion of the biofluid in the viewing reservoir 306 will be transferred to these three testing reservoirs 308, 310 and 312 for testing/analysis and viewing at the associated viewing reservoir 318. The serpentine shape, when used with a medium containing cells such as in a biologic sample, facilitates and enhances mixing due to the increased interfacial contact area between the cells within the biofluid sample.

The next step of testing/analysis will be selected only upon a positive test occurring within one of the three testing reservoirs 308, 310 and 312. However, each of the testing reservoirs 308, 310 and 312 has associated there with a subsequent group of testing reservoirs. In this embodiment, each of the subsequent testing reservoirs is comprised of a plurality of sub reservoirs 330, each of the sub reservoirs 330 being configured identical to the testing reservoirs 308, 310 and 312, with a serpentine microchannel region 316 and a viewing reservoir 318. A single bypass microchannel 220 is provided to connect viewing reservoir 306 to a sub reservoir manifold 332. Each of the particular sub reservoir paths have associated there with a separate micropump 334. Only one of these micropumps 334 is selected for transferring the remaining portion of the biofluid stored in the viewing reservoir 306 to the selected path. In this embodiment, the remaining portion of the biofluid is transferred to the first reservoir 330 bypassing the biofluid through the serpentine microchannel 316 to the associated viewing reservoir 318. This particular microchannel will have coating of antibiotic, in this example above, at a relatively low dose. If the bacteria, for example, do not react accordingly with this level of antibiotic, it can be recognized as such in the viewing reservoir 318. It is noted that the antibiotic associated with the coating on the walls of the microchannel 330 at this dosage will not be picked up by the bacteria and, as such, the bacteria in the viewing reservoir 318 for the first sub reservoir 330 in the selected path will still be intact. It can then be pumped from the reservoir 318 associated with the first testing reservoir 330 in the chain to a subsequent testing reservoir 330 with a subsequent micropump 336. This subsequent sub reservoir will have a concentration of antibiotic in its serpentine microchannel 316 that is at a higher level. As the level increases, a gradient is tested for, such that the dosage can be gradually increased until the bacteria are destroyed. If, for example, the bacteria were associated with an affinity label that made it fluoresce, this would be recognized. It could also be that there are multiple bacterial types contained within the biofluid that are each associated with a different affinity label and this could be recognized. It could, in fact, the case that one type of bacteria perfected at a first dosage level of the antibiotic and a second bacteria were affected at a another dosage level of the antibiotic.

Figure 3B:
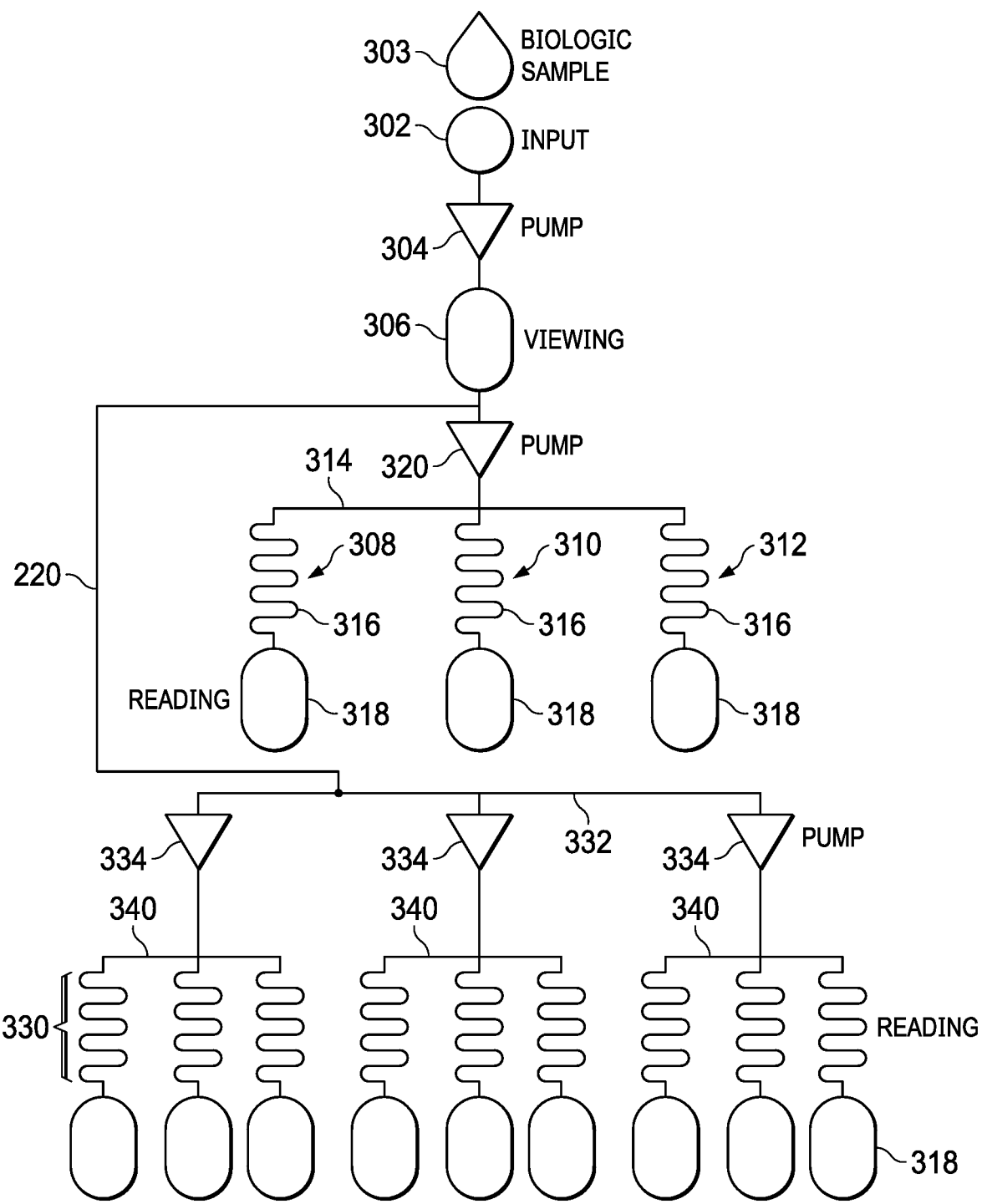

Referring now to FIG. 3B, there is illustrated a diagrammatic view of an alternate process flow. This will work substantially identical to the embodiment of FIG. 3A, come up until the operation at the manifold 332 associated with the sub reservoirs. In this embodiment, the three micropumps 334 each feed a sub reservoir manifold 340. Each of the sub reservoir manifolds 340 is connected to a plurality of the sub reservoirs 330 associated with each path. In this embodiment, there are only illustrated three sub reservoirs 330 for each of the sub reservoir manifolds 340, although each path could have a different number of sub reservoirs 330 associated therewith. The difference between these two embodiments is that, at this point, the amount of biofluid remaining in the viewing reservoir 306 now must be divided amongst all of the sub reservoirs attached on one end thereof to the associated sub reservoir manifold 340 selected by the activated one of the micropumps 334. This will result in potentially less biofluid being available for the testing/analysis step. This will also mean that each of the viewing reservoirs 318 associated there with will have a smaller volume associated therewith.

Figure 3C:
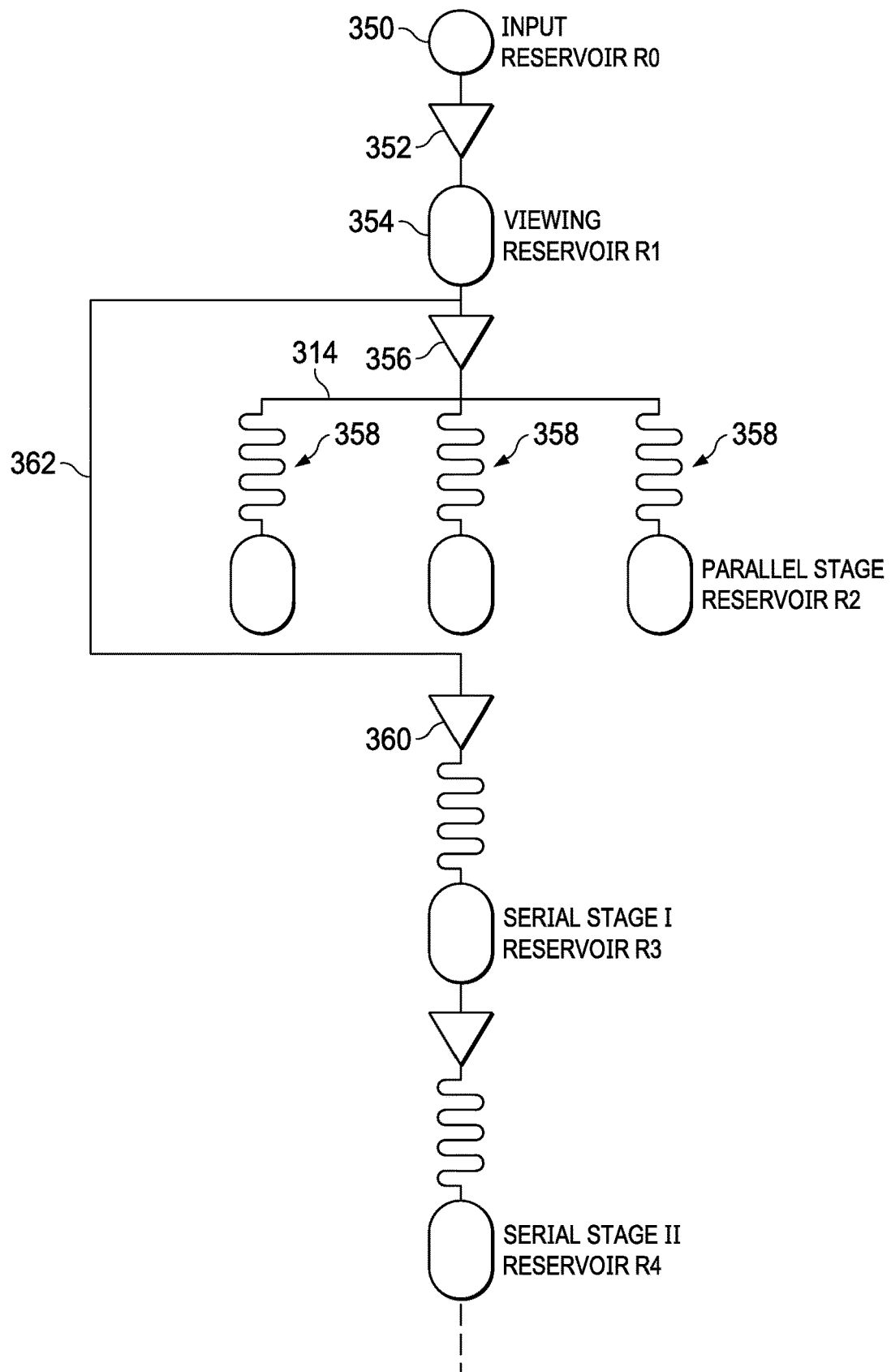
Figure 3D:
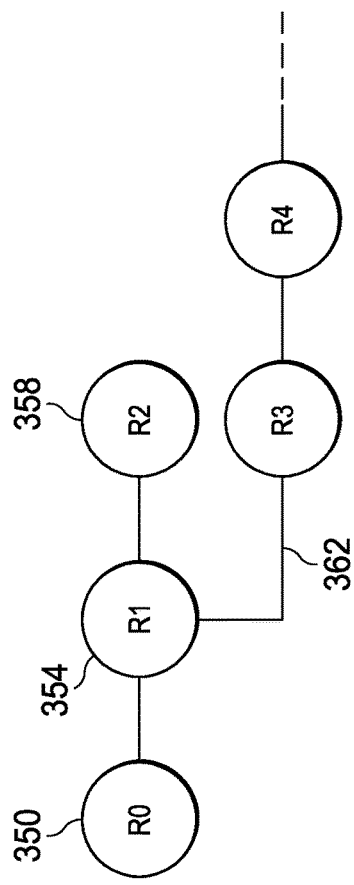

Referring now to FIG. 3C, there is illustrated a diagrammatic view that provides a simplified diagram of the transfer from reservoir to reservoir. In this illustration, the input stage is illustrated as an input reservoir 350 labeled R0. A micropump 352 is operable to transfer the contents of this input reservoir, the biofluid, to a second reservoir, a viewing reservoir 354, labeled R1. A portion of the contents of this reservoir are then transferred via a micropump 356 to a plurality of parallel stage reservoirs 358 labeled R2. This is the first testing/analysis stage. After this stage, the remaining contents of the viewing reservoir 354 are transferred to the subsequent serial stage reservoirs via a pump 360 via a bypass path and microchannel 362. The serial stage reservoirs are labeled R3, R4, etc. This illustration sets forth how the entire contents of the input reservoir R0 are transferred down the chain. This is best illustrated in FIG. 3D. In this illustration, it can be seen that entire contents of reservoir R0 are transferred to reservoir R1. At this point, only a portion of the contents are transferred to reservoir R2. The remaining contents are sequentially transferred to R3, R4, and so on. For this illustration, the entire remaining contents of the reservoir 354, R1, will be transferred down the chain entirely to reservoir R3, then to reservoir R4, and so on. In the alternate embodiment, as described hereinabove, and not illustrated in FIG. 3D, the bypass 362 could be connected to each of the reservoirs R3, R4, etc. in parallel, noting that the remaining contents of the reservoir R1 will then be divided amongst the parallel connected reservoirs R3, R4, etc.

Referring now to FIGS. 4A-4G, there are illustrated diagrammatic views of the initial processing section associated with the viewing stage 108. There is provided a substrate 402 upon the surface of which are formed a plurality of wells and microchannels. A first well 404 is provided for receiving the biofluid sample in this well has a finite volume associated there with. At the bottom of this well a microchannel 406 extends outward and up to the surface to an opening 408. The purpose of this microchannel 406 extending to the bottom of the well 404 is to ensure that the biofluid can be completely pumped from the well 404. For the formation of this microchannel 406, it might be that the microchannel is formed through the surface of the substrate 402 and then a cover plate (not shown) having a surface that extends down into the open microchannel. An adjacent channel 410 is disposed proximate the opening 408 to provide another opening therefore in order to accommodate a micropump 412 (shown in phantom) interface with the opening 408 and the one end of the microchannel 410 for transferring fluid from the well 404 to the microchannel 410. The microchannel 410 extends along the surface of substrate 402 in order to interface with a viewing well/reservoir 412. As the biofluid passes through the microchannel 410 and the viewing well 412, a desired analysis can be performed on the contents of the biofluid. As described hereinabove, in one example, various cells in the biofluid might consist of different types of bacteria, proteins, etc. and each of these may have associated there with a specific affinity label, which is optically detectable. There are, of course, other means by which affinity labels can be detected. As the cells contained within the biofluid pass through the viewing well/reservoir 414, they can be examined. The viewing well/reservoir 414 on the other side thereof is connected to one side of a microchannel 416, the other side thereof connected to a reservoir 418. Since the micropump 412 must force the biofluid through the microchannels and the viewing well/reservoir 414, there is required the necessity for a holding reservoir 418 to be present. However, initially, this reservoir 418, the microchannel 410 and the viewing well/ reservoir 414 will have air disposed therein. This air must be removed. This can be done with a negative pressure of some sort or just a waste gate output to the atmosphere. This is provided by a waste gate microchannel 420 that is connected to an opening 422 through the cover glass (not shown) or to the side of substrate 402. A valve 423 could be provided above the opening 422. As biofluid enters the reservoir 418, air will be pushed out through the microchannel 420. It is desirable for this microchannel 422 to have as low a profile as necessary such that only air exits therefrom. Depending upon the size of the cells contained within the biofluid, the microchannel 420 can be significantly smaller and have a lower profile than the microchannels 410 and 416. Is important to note that, once the micropump 412 transfers the biofluid from the well 404, the volume transferred will be spread between the two microchannels 410 and 416, the viewing well 414 and the reservoir 418. Thus, the reservoir 418 has a significantly larger volume that any of the microchannels 410 and 416 and the viewing well/reservoir 414. Additionally, it may be that the depth of the wells/reservoirs 404 and 418, as well as the viewing well reservoir 414 are also as shallow as the microchannels 410 and 416 but significantly wider to accommodate the required volume.

Figure 4A:
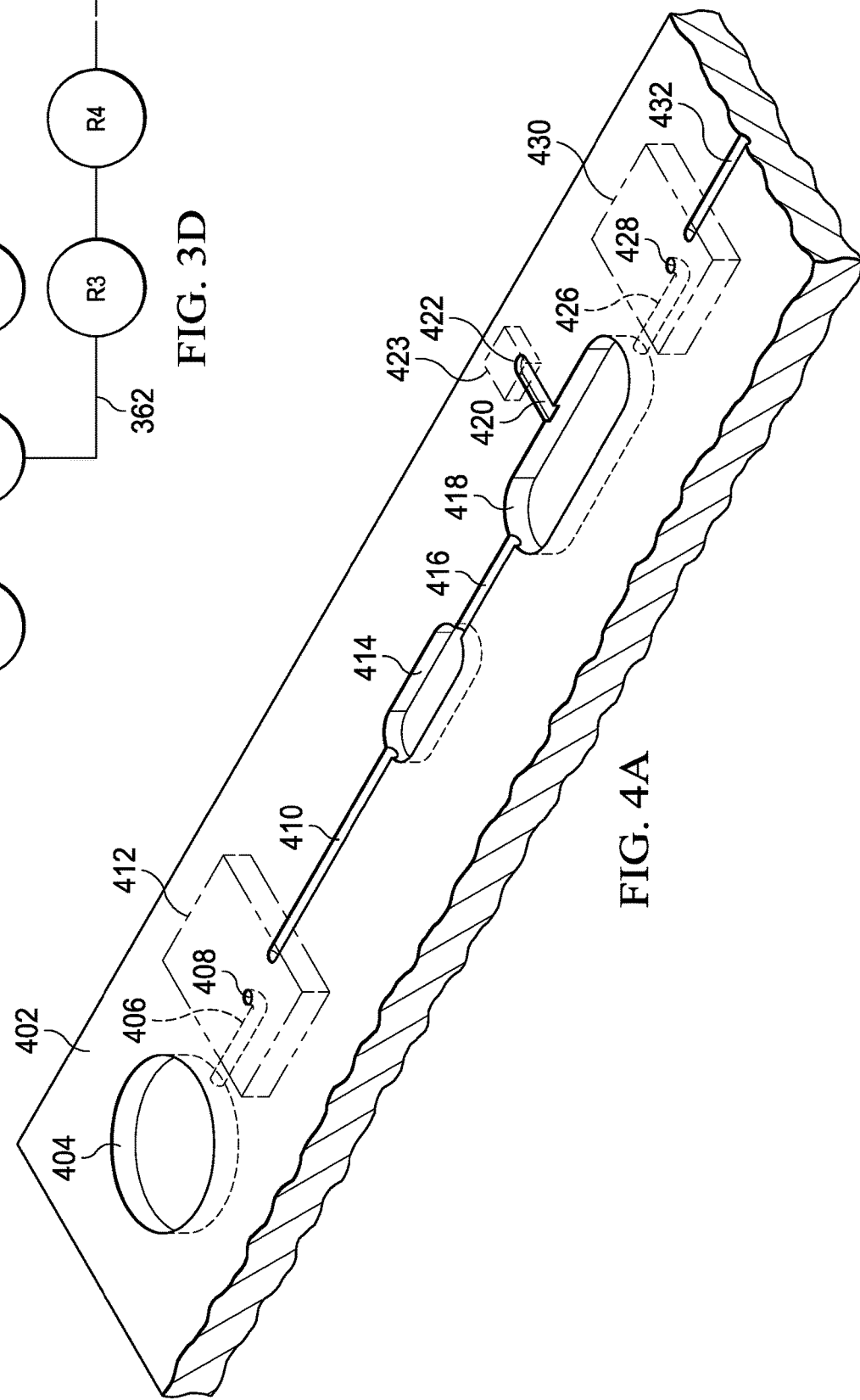

The outlet of the reservoir 418 is connected from the bottom thereof through a microchannel 426 to an opening 428 on the upper surface of the substrate 402. This is interfaced with a micropump 430 (in phantom) to an adjacent microchannel 432 for subsequent processing. These micropumps 412 and 430, although illustrated as being flush with the substrate, will typically be disposed above the cover plate (not shown) with holes disposed through the cover plate. The opening 428 will be a horizontal microchannel associated with the manifold 314 described hereinabove. This will be associated with a plurality of micropumps 430 for each of the parallel paths or the bypass path. A cross-sectional view of the embodiment of FIG. 4A is illustrated in FIG. 4B, with a cover plate 440 disposed over the substrate 402 with an opening 442 disposed above the well 404 for receiving the biofluid sample.

Figure 4C:
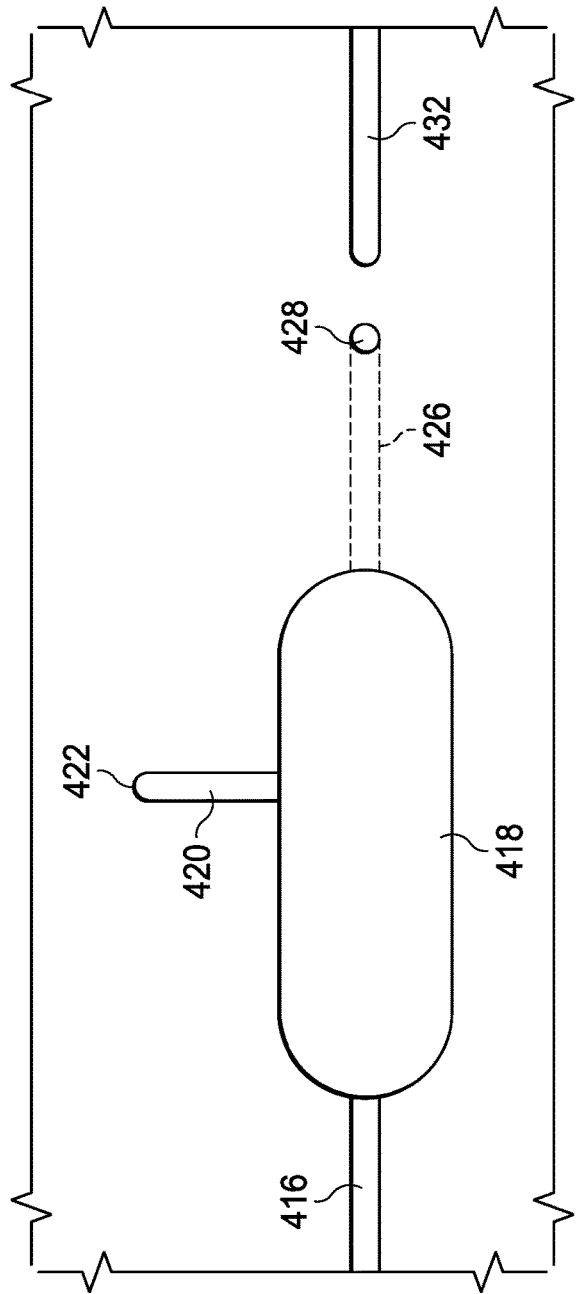
Figure 4D:
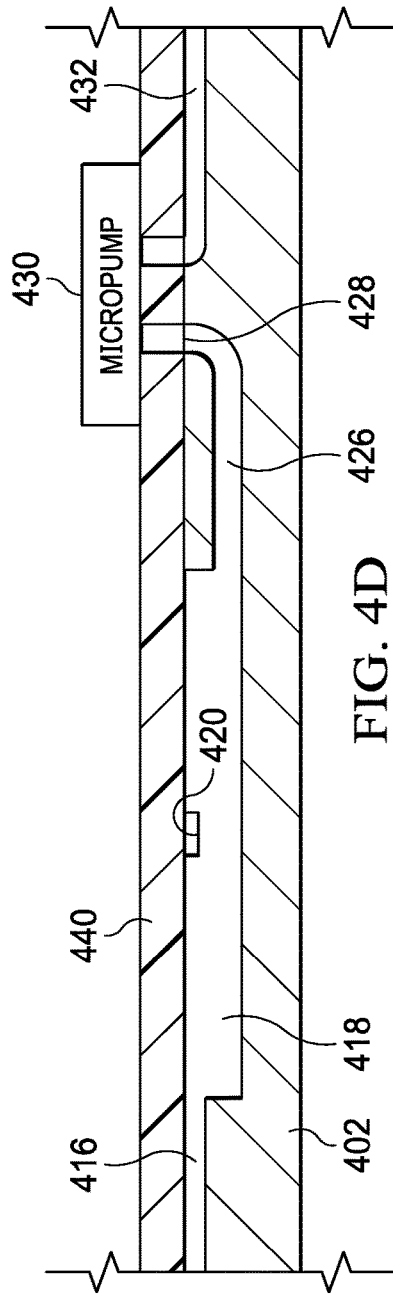

FIGS. 4C and 4D illustrate top view and cross-sectional views of the reservoir 418 illustrating how the microchannel 416 feeds biofluid into the top of the reservoir 418, and the flow path for the biofluid from the reservoir 418 through the microchannel 426 from the bottom of the reservoir 418. However, it may be that, with capillary action, the depth of the reservoir 418 could be equal to that of the microchannels 416 and 426 such that they are all at the surface of the substrate 402 for ease of manufacturing. When a negative pressure is placed upon the reservoir 418, air will be pulled into the microchannel 426 through the microchannel 420. It is possible in this mode that the micropump 412 could be operated to actually create a positive pressure in the microchannel 416 to force the biofluid in the reservoir 418 into the opening 428 through the microchannel 426. Again, the microchannel 420 would preferably have a dimension that was smaller than the smallest cell size within the biofluid.

Referring now to FIGS. 4E and 4F, there are illustrated top view and cross-sectional views of the reservoir 418 with an alternate embodiment illustrating microchannel 426' as being beneath the bottom of the reservoir 418 to allow more complete emptying of the reservoir 418.

Figure 4G:
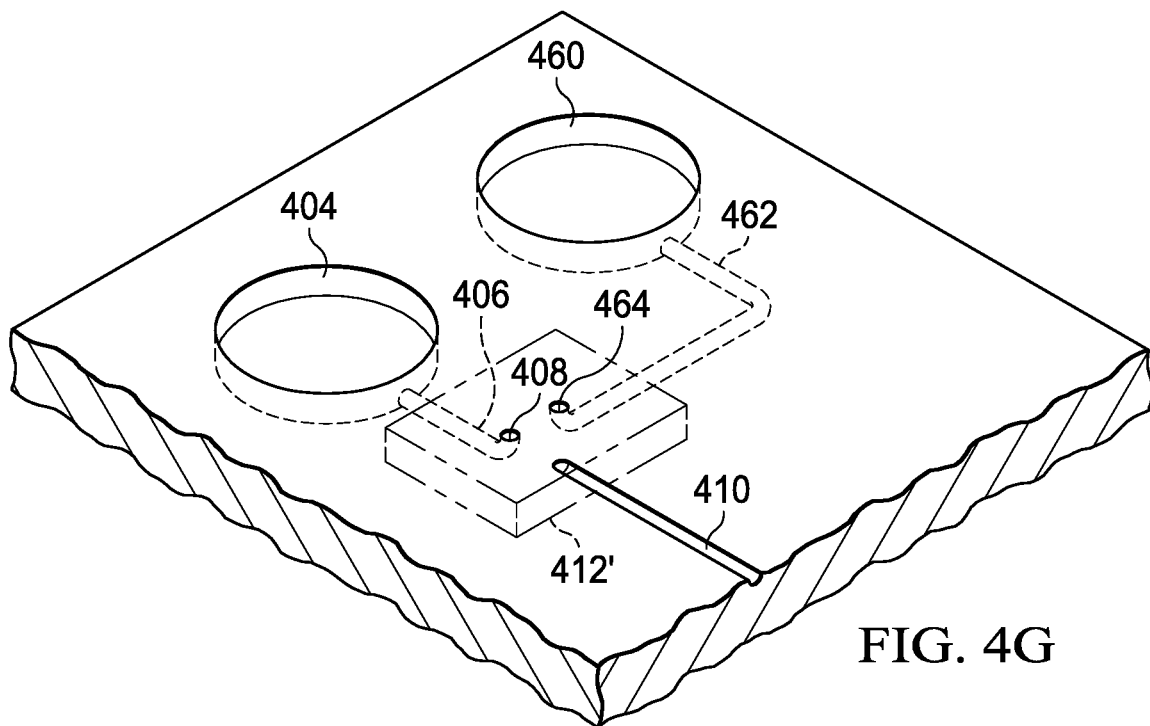

Referring now to FIG. 4G, there is illustrated an alternate embodiment of inlet wells for receiving the biofluid sample. There is provided the well 404 for receiving the biofluid sample and a second well 464 receiving an additional fluid sample. This fluid sample in well 460 could be some type of dilutant or it could be a medium containing various affinity labels. As noted hereinabove, the fluid sample could have associated there with affinity labels prior to the biofluid sample being disposed in the well 404. However, it is possible that the microfluidic chip have disposed in the well 460 a medium containing affinity labels, for example. The well 460 would be interfaced through a microchannel 462 to an opening 464 adjacent the opening 408. A two input, one output, micropump 412' that interfaces with the microchannel 410.

Figure 5A:
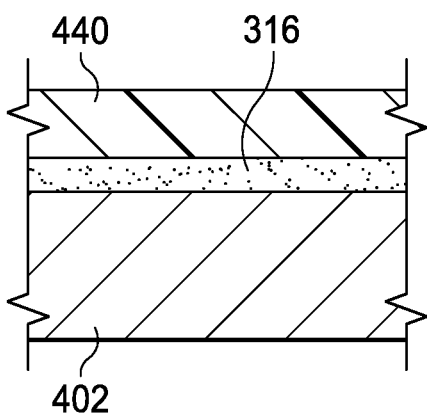
FIGS. 5A and 5B illustrate details of the coating applied to the micro channels in the first driving stage.
Figure 5B:
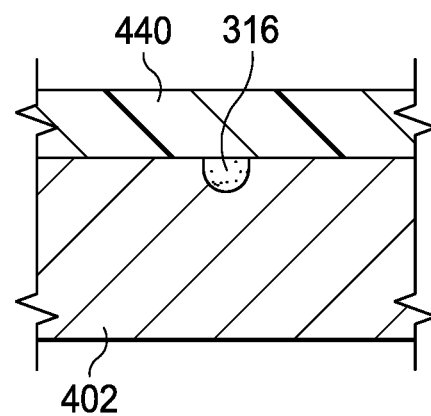
Figure 5:
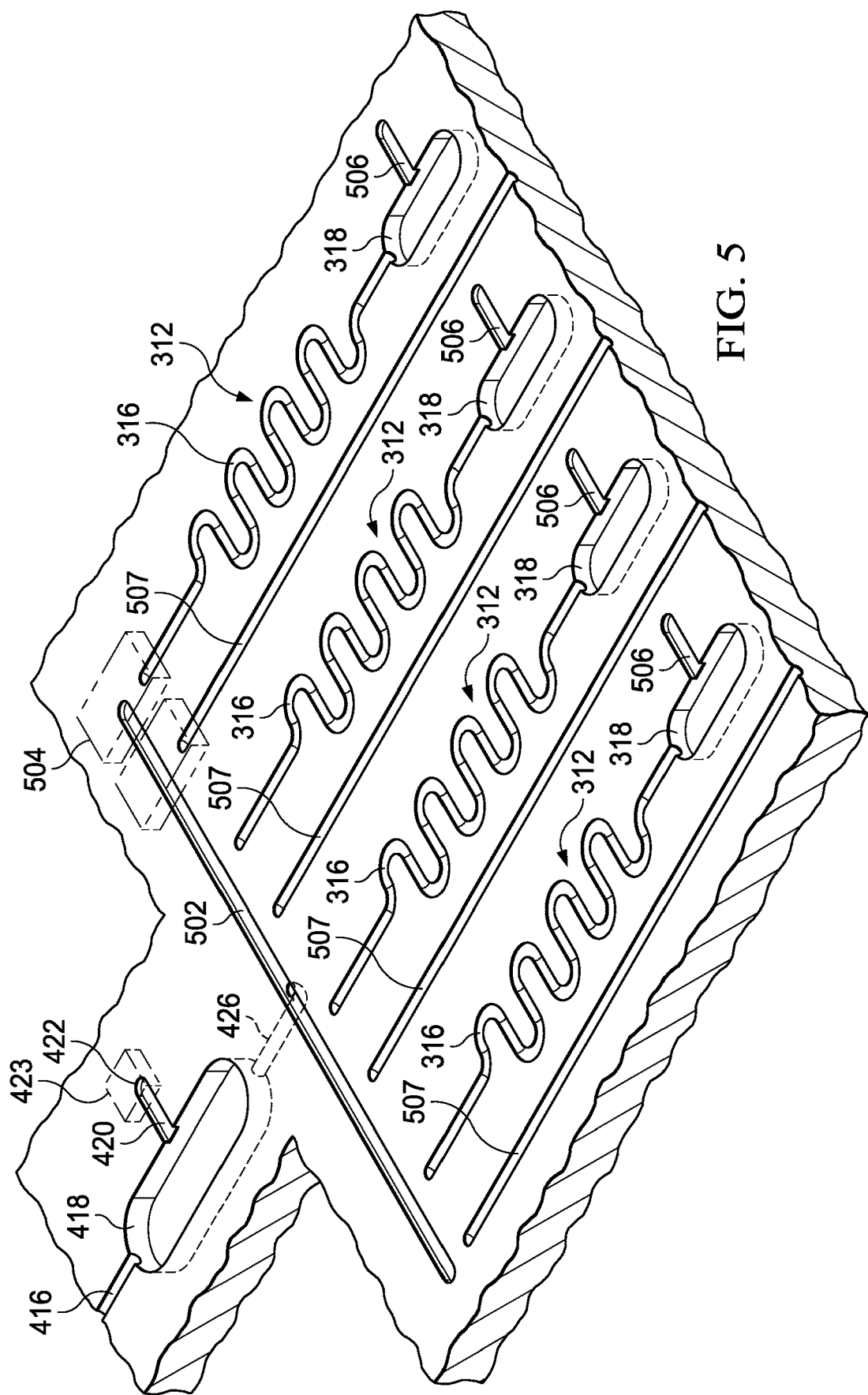
FIG. 5 illustrates a detailed view of the first parallel driving stage.

Referring now to FIG. 5, there is illustrated a diagrammatic view of the microchannel structure associated with the parallel stage of operation. The microchannel 426 is interfaced with a microchannel manifold 502 which corresponds to the opening 428. This microchannel manifold 502 is interfaced with a plurality of micropumps 504, corresponding to the micropump 430. These micropumps 504 are disposed in pairs, each pair associated with one testing reagent. As noted hereinabove, there are provided a plurality of parallel paths, each associated with a reservoir 312 having a serpentine microchannel 316 and a viewing reservoir 318. The first micropump 504 in the pair of micropumps 504 is connected to one end of the associated serpentine microchannel 316. When this micropump 504 is activated, biofluid from the reservoir 418 is passed through the manifold microchannel 502 and through the serpentine microchannel 316 to the viewing reservoir 318. As was the case above, there is provided a waste microchannel 506 for each of the reservoirs 318 to allow air to escape therefrom as biofluid is forced through the microchannel 316. The micropump 504 associated with this serpentine microchannel 316 will be operated for a sufficient amount of time to transfer sufficient biofluid from the reservoir 418 through the serpentine a channel 316 and finally into the reservoir 318 to fill the reservoir 318. The microchannel 506 can have some type of valve associated with the opening thereof to prevent the escape of any biofluid therefrom or, alternatively, the dimensions of that microchannel 506 could be small enough to prevent any appreciable amount of cells escaping therefrom. Although not illustrated, the one of the pair of micropumps 504 associated with the parallel stage of operation and associated reservoirs 312 will also be operated to fill the associated serpentine microchannel 316 and reservoir 318.

Referring now to FIGS. 5A and 5B, there are illustrated cross-sectional views of the serpentine microchannel 316. As described hereinabove, the sides of these channels 316 are coated with some type of reagent. For example, if a Urinary Tract Infection (UTI) were suspected and were being tested for in the microfluidic chip, the sensitivity for common antimicrobial agents for UTI treatment might include ampicillin (AMP), ciprofloxacin (CIP), and trimethoprim/sulfamethoxazole (SXT), these being three agents that could be tested for and three different paths. The bacteria that might exist within the urine samples from an individual could be any of uropathogenic *E. coli* strains (EC132, EC136, EC137, and EC462). Some prior research has shown that, through antimicrobial resistance profiles of these pathogens that EC132 is resistant to AMP and CIP but not SXT. EC136 is resistant to AMP only. EC137 is sensitive to all the antibiotics tested. EC462 is resistant to AMP and SXT but not CIP. In order to coat sides of the serpentine microchannels 316, one technique would to have a certain amount of the antibiotic dissolved in sterile water to the serpentine microchannels 316 at different levels. Subsequently, the diluted antibiotic is dried by incubation at a desired temperature and desired time. The original diluted antibiotic has a starting concentration of a predetermined µg/ml concentration. The surface area is sufficiently covered such that, when the biofluid passes thereover, it will interact with reagent.

Figure 6:
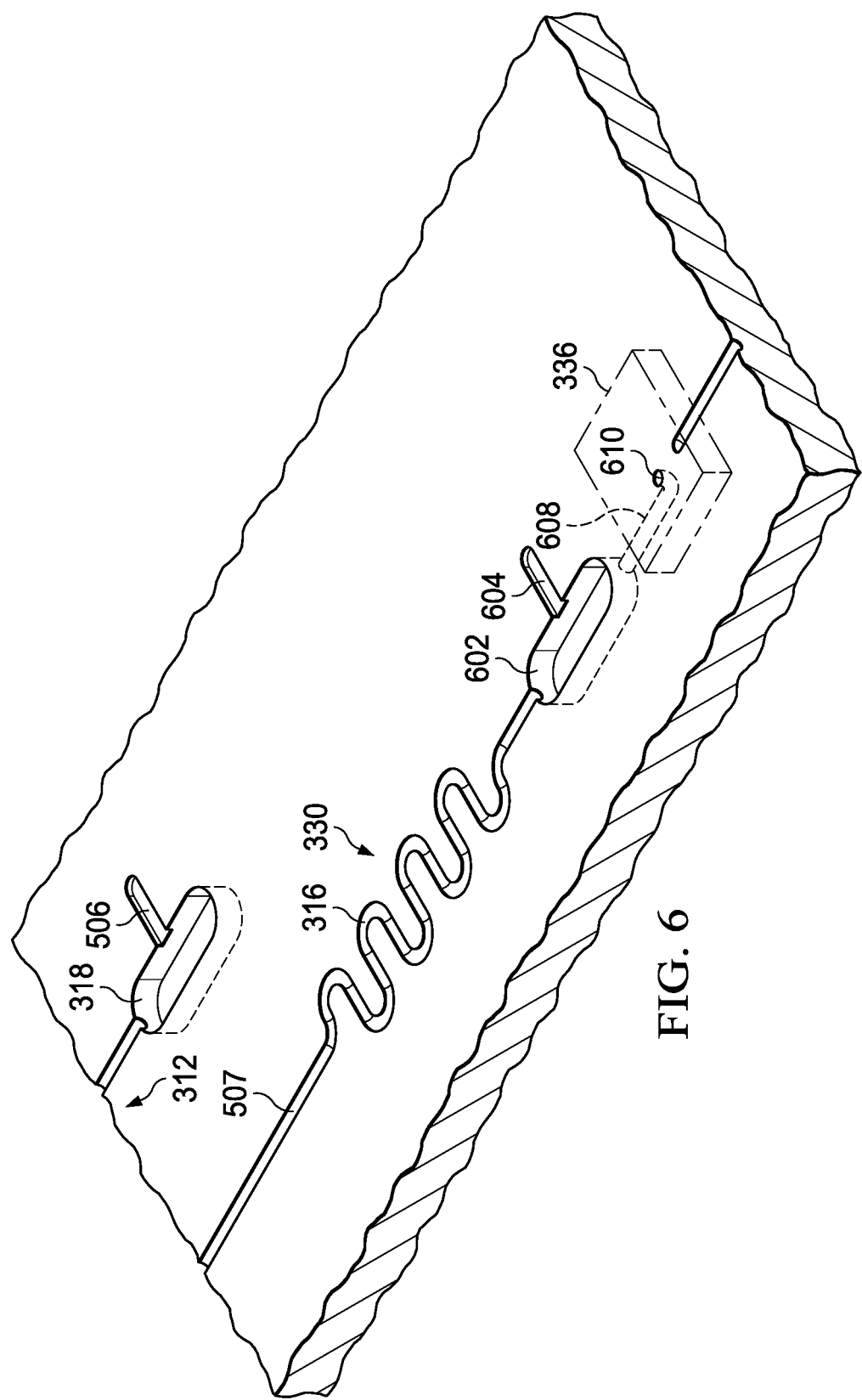
FIG. 6 illustrates a detail of the serial driving stage.

Referring now to FIG. 6, there is illustrated a microchannel diagram of the reservoir 330 on the surface of the chip 402. This is connected by the microchannel 507 from the associated one of the micropumps 504. After the results in the viewing reservoir 318 have been determined to yield a positive result, for that particular path in the parallel analysis/testing operation, the other of the pair of micropumps 504 is activated and the remaining amount of micro-fluid from the reservoir 418 is transferred to the reservoir 330. This will be passed through the serpentine microchannel 316 and stored in the reservoir 318, labeled 602 in FIG. 6. This is substantially larger than the reservoir 318 associated with the reservoir 312. Thus, for this embodiment, the remaining portion of the biofluid from the reservoir 418 will be substantially stored in the reservoir 602. This will have associated there with a waste microchannel 604 and an outlet microchannel 608 that extends outward from the bottom of the reservoir 602 and up to an opening 610 in the surface of the substrate for interface with the micropump 336. The micropump 336 is operable, at the next stage of the testing/analysis, to move the contents of the reservoir 602 over to the next reservoir 330 for testing at that next concentration level associated with the next reservoir 330 in the sequence.

Referring now to FIGS. 7A-7D, there is illustrated an example of a valveless MEMS micropump. The micropump includes a body 702 with two pumping chambers 704 and 706. At the inlet side of each of the chamber 704 and 706 is disposed a conical inlet 710 and 712, respectively. The conical inlets 710 and 712 are wider at the pump chamber side and narrower at the inlet side thereof. The inlet sides of conical inlet 710 and 712 are connected to respective inlet channel 714 and 716. The outlet side of the chambers 704 and 706 are interfaced with conical outlets 718 and 720, respectively, the conical outlets 718 and 720 having a narrower portion at the outlet of the respective pump chamber 704 and 706 and a wider portion at the respective outlet thereof interfacing with respective outlet channels 722 and 724. The conical inlets 710 and 712 and outlets 718 and 720 are frustro conical in shape. A piezoelectric membrane and actuator 726 is dispose between the two pumping chambers 704 and 706 and is operable to be extended up into one of the chambers 704 and 706 at one time to increase the pressure therein and at the same time extend away from the other of the chambers 704 and 706 to decrease the pressure therein. The operation is then reversed.

The piezoelectric membrane and actuator 726 is comprised of a piezoelectric disc 740 on one side of a membrane 742 and a piezoelectric disc 744 on the other side thereof. Each of the piezoelectric discs 740 and 744 are formed by stratifying a layer of use electric material 748 between two layers of conducting material 750. Piezoelectric material 748 can be made with Piezo Material Lead Zirconate Titanate (PZT-SA), although other piezoelectric materials can be used. The conducting material 60 may be composed of an epoxy such as commercially available EPO-TEK H31 epoxy. The epoxy serves as a glue and a conductor to transmit power to the piezoelectric discs 750. The piezoelectric discs 750 are secured to the surface of the intermediate layer 748, so that when a voltage is applied to the membrane 742, a moment is formed to cause the membrane 742 to deform.

Figure 7A:
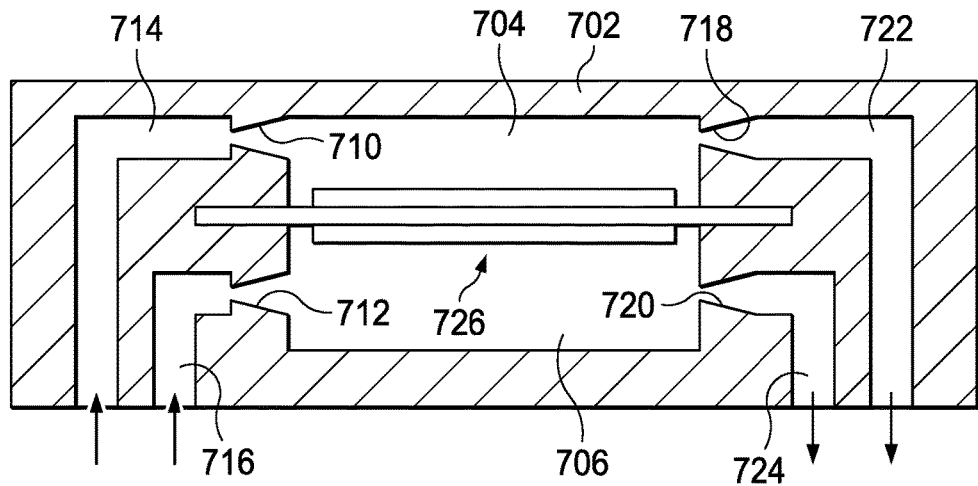
FIGS. 7A-7D illustrate detailed views of a valveless nozzle/diffuser micropump.
Figure 7B:
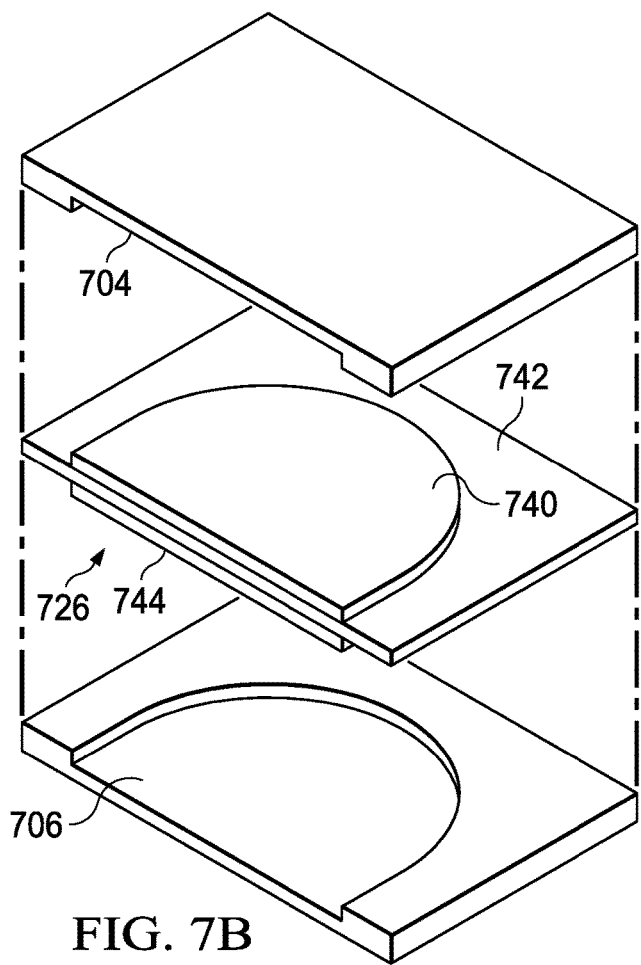
Figure 7C:
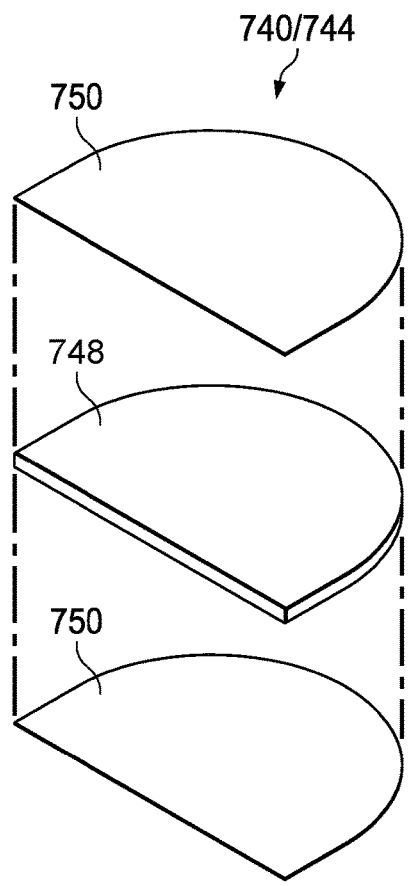
Figure 7D:
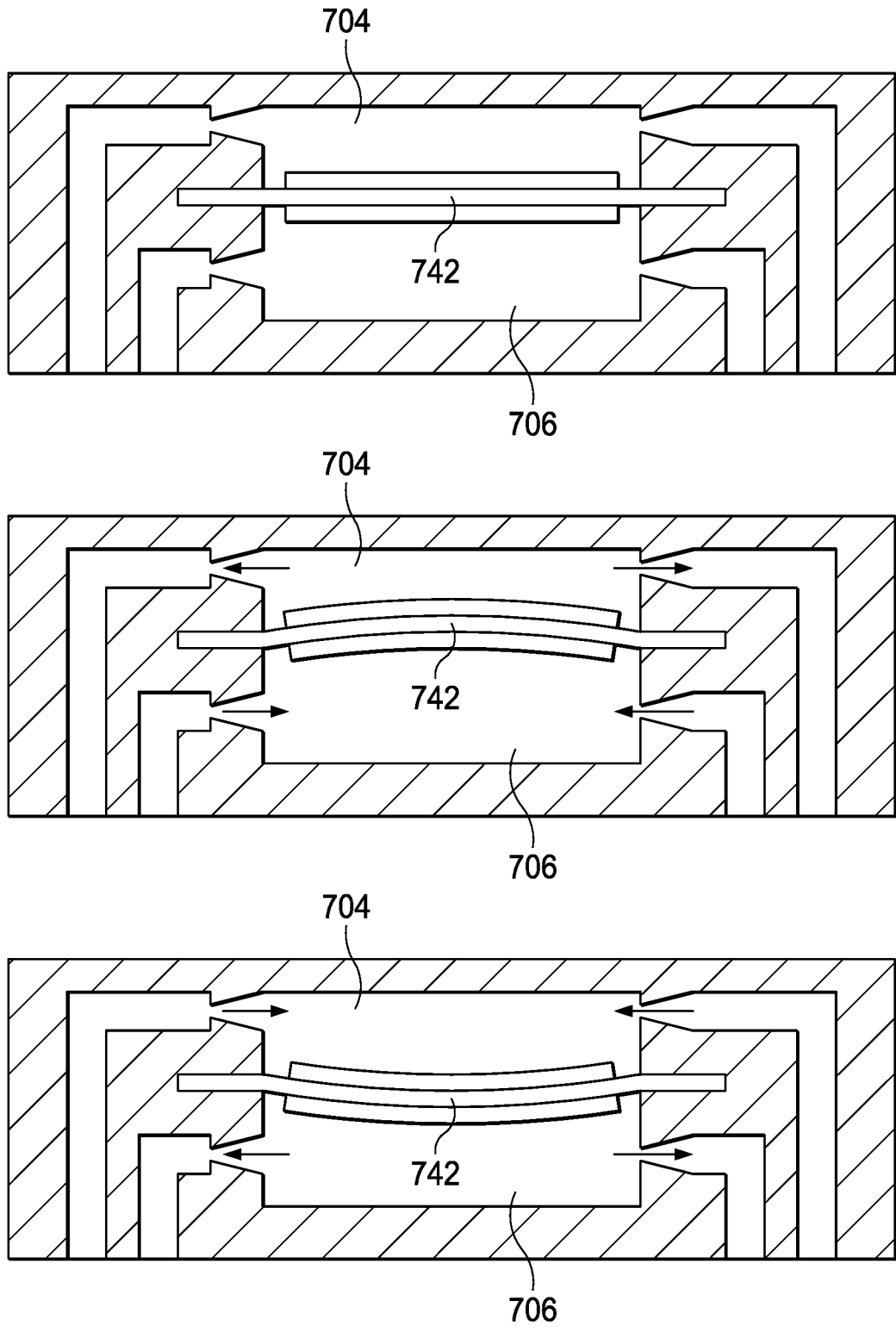

The operation of the micropump will be described with reference to FIG. 7D. At rest, the upper chamber 704 and the lower chamber 706 are separated by a diaphragm pump membrane 742. The diffuser elements 710, 712, 718 and 720 are in fluid communication with each respective chamber. Diffuser elements are oriented so that the larger cross-sectional area end of one diffuser element is opposite the smaller cross-sectional area end of the diffuser element on the other side of the chamber. This permits a net pumping action across the chamber when the membrane is deformed.

The piezoelectric discs are attached to both the bottom and the top of the membrane. Piezoelectric deformation of the plates is varied by varying the applied voltage so as to excite the membrane with different frequency modes. Piezoelectric deformation of the cooperating plates puts the membrane into motion. Adjustments are made to the applied voltage and, if necessary, the choice of piezoelectric material, so as to optimize the rate of membrane actuation as well as the flow rate. Application of an electrical voltage induces a mechanical stress within the piezoelectric material in the pump membrane 742 in a known manner. The deformation of the pump membrane 742 changes the internal volume of upper chamber 704 and lower chamber 706. As the volume of the upper chamber 704 decreases, pressure increases in the upper chamber 706 relative to the rest state. During this contraction mode, the overpressure in the chamber causes fluid to flow out the upper chamber 704 through diffuser elements on both sides of the chamber. However, owing to the geometry of the tapered diffuser elements, specifically the smaller cross-sectional area in the chamber end of the left diffuser element relative to the larger cross-sectional area of the right diffuser element, fluid flow out of the left diffuser element is greater than the fluid flow out the right diffuser element. This disparity results in a net pumping of fluid flowing out of the chamber to the left.

At the same time, the volume of the lower chamber 706 increases with the deformation of the pump member 742, resulting in an under pressure in the lower chamber 706 relative to the rest state. During this expansion mode, fluid enters the lower chamber 706 from both the left and the right diffuser elements. Again owing to the relative cross-sectional geometry of the tapered diffuser elements, fluid flow into the lower chamber 706 through the right diffuser element is greater than the fluid drawn into the lower chamber 706 through the left diffuser element. This results in a net fluid flow through the right diffuser element into the chamber, priming the chamber for the pump cycle.

Deflection of the membrane 742 in the opposite direction produces the opposite response for each chamber. The volume of the upper chamber 704 is increased. Now in expansion mode, fluid flows into the chamber from both the left and right sides, but the fluid flow from the right diffuser element is greater than the fluid flow from the left diffuser element. This results in a net intake of fluid from the right diffuser element, priming the upper chamber 704 for the pump cycle. Conversely, the lower chamber 706 is now in contraction mode, expelling a greater fluid flow from the lower chamber 706 through the left diffuser element than the right diffuser element. The result is a net fluid flow out of the lower chamber 706 to the left.

Figure 8:
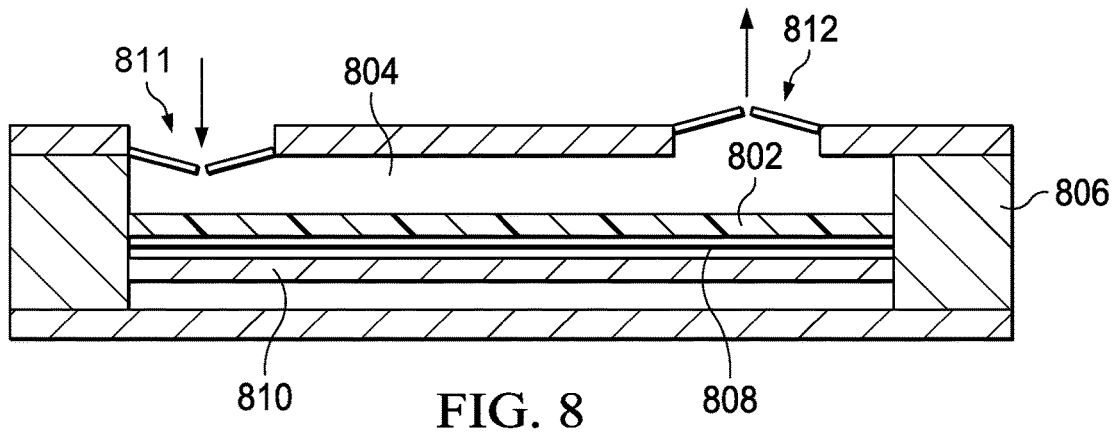
FIG. 8 illustrates a detailed view of a piezoelectric micropump.

Referring now to FIG. 8, there is illustrated a cross-sectional view of a piezoelectric micropump with check valves. Membrane 802 is disposed within a pump chamber 804 and secured to a body 806. A piezoelectric disc 808 is disposed beneath the membrane 802 and electrode 810 is disposed below the piezoelectric disc 808. Deformation of the membrane 802 with the piezoelectric disc at the appropriate frequency will cause a volume of the pumping chamber 804 to change. An inlet valve 811 allows fluid to flow into the chamber 804 and an outlet valve 812 allows fluid to flow out of the chamber 804.

Figure 9:
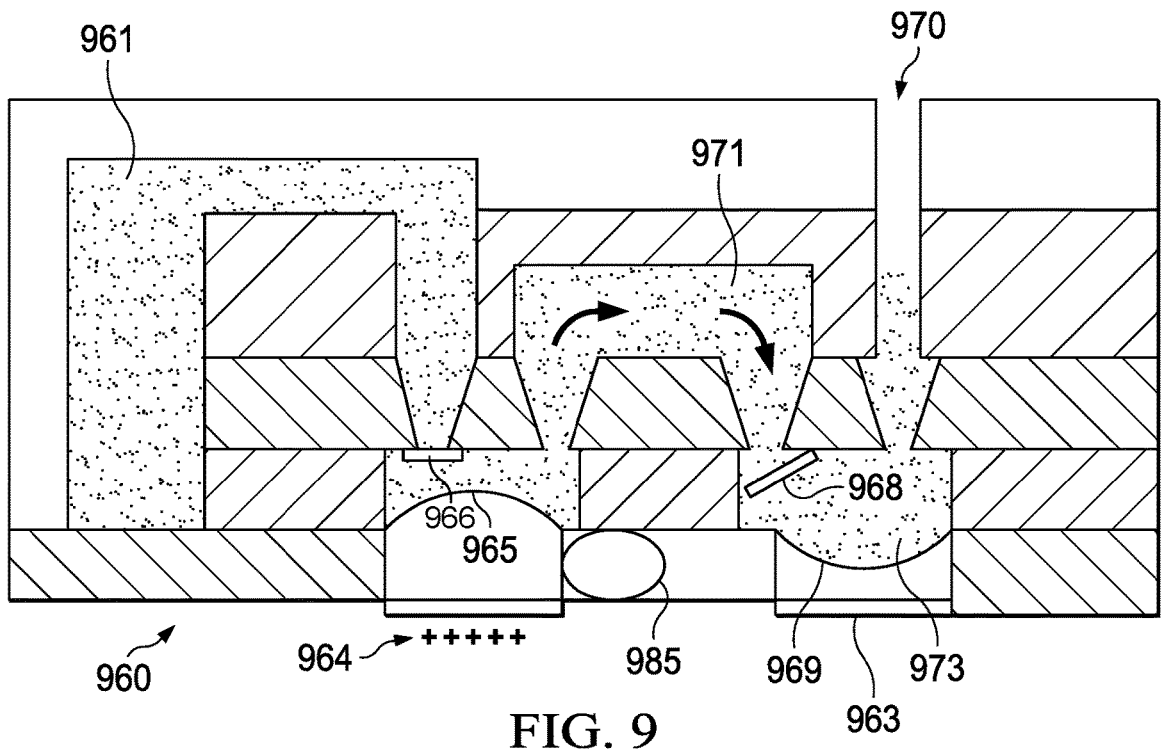
FIG. 9 illustrates a detailed view of a multi-chamber micropump with check valves.

Referring now to FIG. 9, there is illustrated a micropump 960 in which a nanofabricated or microfabricated fluid flow pathway is formed between structures. A first reservoir 961 terminates with a first gate valve 966 which permits or restricts fluid flow between the first reservoir 961 and a second reservoir 971. An electrolytic pump 985 drives a first diaphragm 965 which is communication with the second reservoir 971, to close the first gate valve 966, and pulls a second diaphragm 969, which opens a second gate valve 968 to drive fluid from the second reservoir 971 to a third reservoir 973. The electrolytic pump 985 is driven by electrowetting of a first membrane 964 on the first gate valve 966 side of the pump. By switching to electrowetting of a second membrane 963 fluid within the third reservoir 973 is emitted from an exit opening 970 by actuation of the second diaphragm 969.

Figure 10:
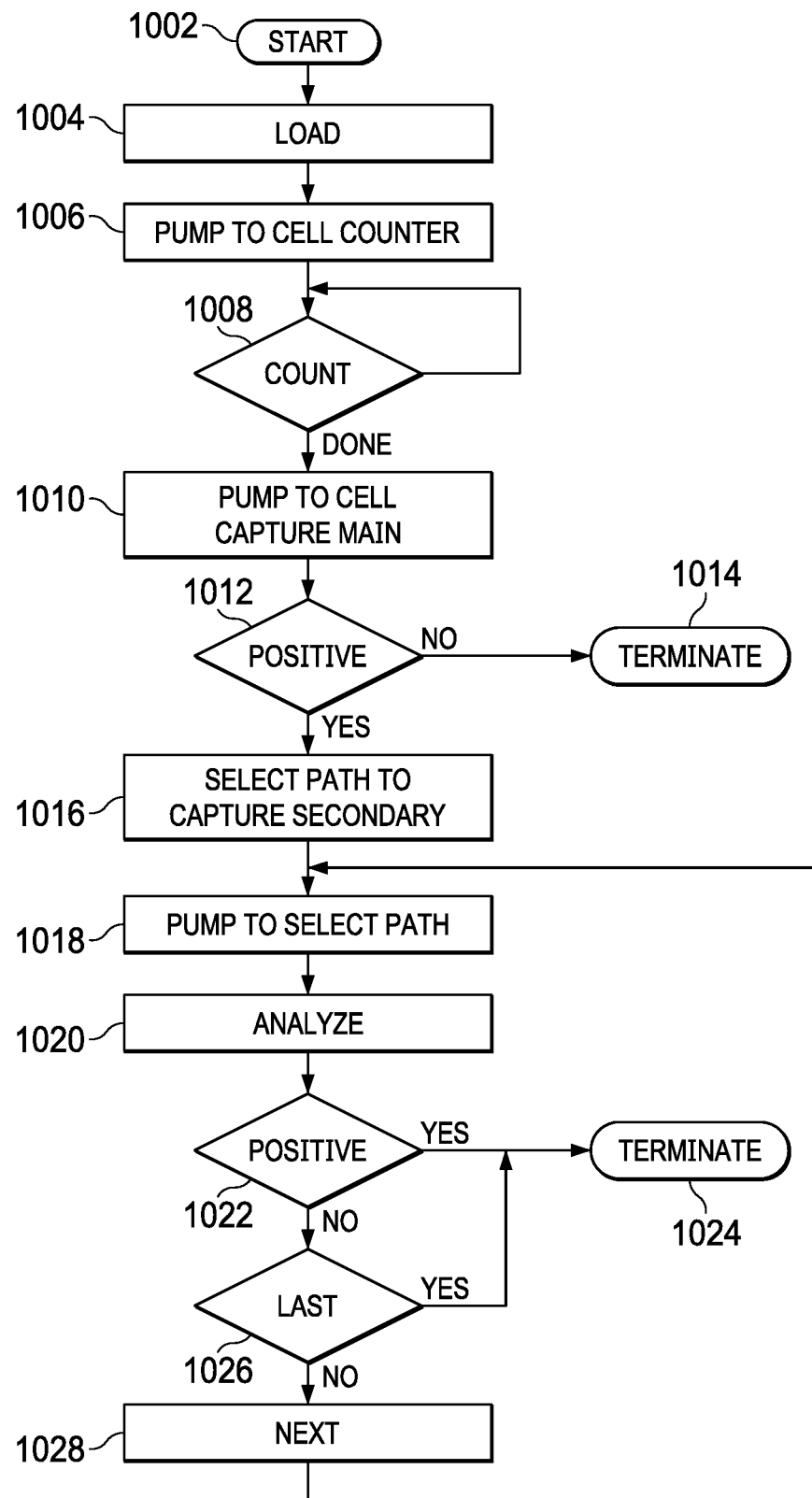
FIG. 10 illustrates a flowchart for the high-level operation of the microfluidics chip.

Referring now to FIG. 10, there is illustrated a flowchart depicting the overall operation of the system. The process is initiated at a Start block 1002 and then proceeds to a block 1004, wherein the biofluid sample is loaded. The process enclosed a block 1006, wherein the biofluid is transferred to the viewing window or the cell counter. The process then flows to a decision block 1008 to determine when the counting operation is done, i.e., when the cells have been discriminated. As noted hereinabove, each of these cells could be associated with, depending on upon the type, a particular affinity label to allow them to be discriminated between within the viewing window. The process then flows to a block 1010 in order to pump the biofluid material to the next phase, that associated with the parallel testing/analysis step. A decision is then made at a block 1012 as to whether this is a positive state, i.e., has any of the biofluid material interacted with a particular reagent to give a positive result. If not, the process is terminated at a block 1014 and, if so, the process flows to a block 1016 in order to capture the biofluid material in a secondary reservoir. Once the path is selected, the appropriate micropump is activated and the biofluid material is pumped to the next reservoir along the secondary path, as indicated by a block 1018. The process then flows to a block 1020 in order to analyze the results at each secondary reservoir and, if there is a positive result, as indicated by block 1022, the process is terminated at a block 1024. If the result is not positive, the process then flows to a block 1026 to determine if that is the last testing reservoir and, if so, the process flows to the terminate block 1024. If there are more testing/analysis blocks through which to process the biofluid material, the process then flows to block 1028 and back to the input of a block 1018 to pump the biofluid serial to the next testing reservoir.

Figure 11:
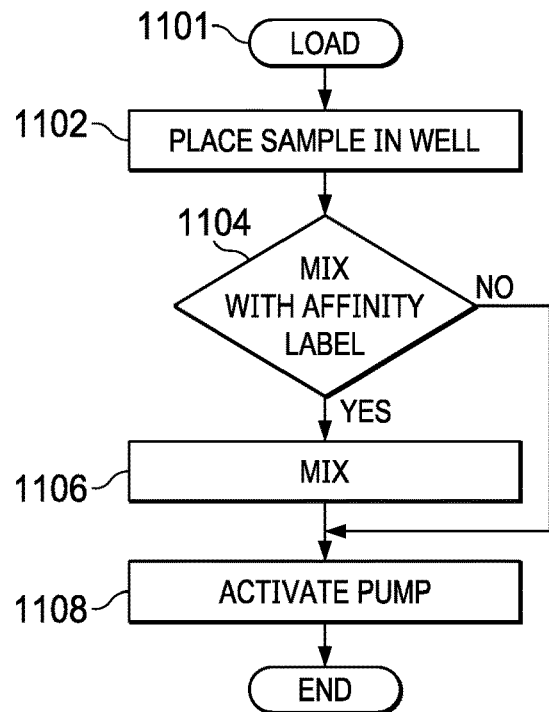
FIG. 11 illustrates a flowchart for the initial loading operation of the fluid sample.

Referring now to FIG. 11, there is illustrated a flowchart for the loading operation, which is initiated at a block 1101 and then flows to a block 1102 wherein the sample is placed in the well and then to a decision block 1104 to determine if this is a process wherein the biofluid sample is to be mixed with some other diluted product or an affinity label. If it is to be mixed, the process flows to a block 1106 to mix the biofluid sample and, if not, the process bypasses this step. The process then flows to a block 1108 in order to activate the pump and transferred the biofluid material after mixing to the next reservoir in the process.

Figure 12:
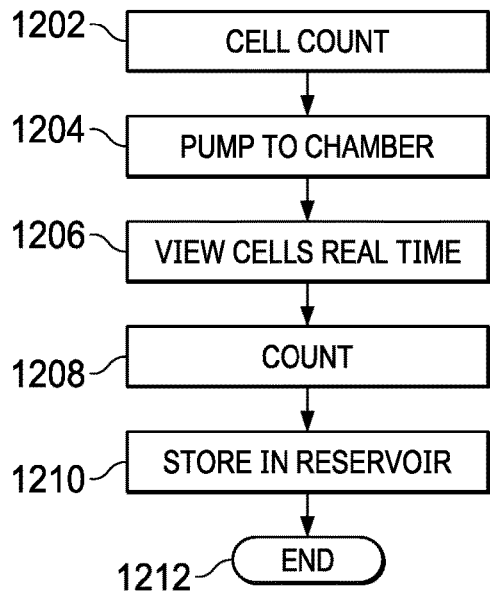
FIG. 12 illustrates a flowchart for the viewing or cell counter stage of analysis.

Referring now to FIG. 12, there is illustrated a flowchart for the process of the cell counting operation, i.e., the operation at the viewing reservoir. This is initiated at a block 1202 proceeds to a block 1204 in order to transfer the biofluid material to the viewing chamber. The process enclosed a block 1206 in order to view the cells in real time as they pass through the various microchannels and viewing window. The process then flows to a block 1208 in order to count the cells. At this stage, the cells can have various affinity labels associated there with such that the target cells can be viewed and discriminated between based upon the affinity labels associated therewith. If, for example, there were multiple types of bacteria contained within the biofluid sample and each of these types of bacteria had associated therewith different affinity label that clips arrest at a different color, they killed be discriminated between. Additionally, proteins would have a different affinity label than a bacteria and this would also allow discrimination between the two types of cells. The process then flows to a block 1210 to store the transferred biofluid in the reservoir and into a block 1212 to terminate.

Figure 13A:
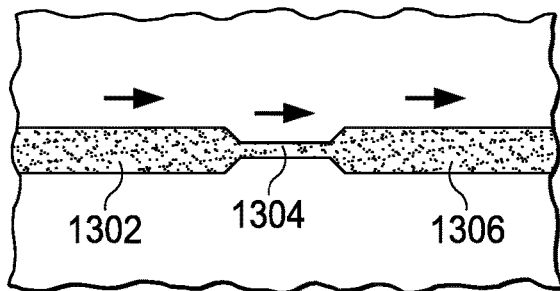
FIGS. 13A-13C illustrate diagrammatic use for the cell counter.
Figure 13B:
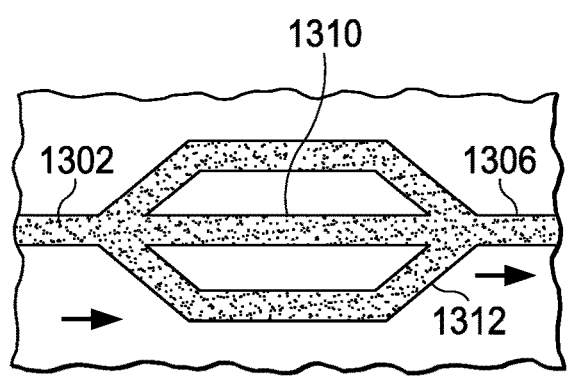
Figure 13C:
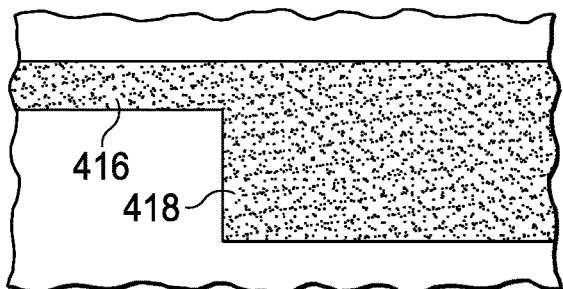

Referring now to FIGS. 13A-13C from their illustrated various configurations for the cell counting operation. In the first embodiment of FIG. 13A, there are provided a three-part microchannel 1302, a middle section microchannel 1304 and an outlet microchannel section 1306 the middle section 1304 has a diameter that is slightly larger than the largest cell that could be contained within the biofluid. This allows the cells to be transferred in a more orderly manner. The cell viewing would be performed at this middle section microchannel 1304. In the embodiment of FIG. 13B, there are provided three varying diameter middle microchannel sections 1308, 1310 and 1312, each with different diameters to allow different size cells to flow therethrough. This type of embodiment may facilitate some selection in the cells for viewing. In the embodiment of FIG. 13C, there is illustrated the above disclose embodiment wherein the microchannel 416 empties into the reservoir 418 and the viewing is basically performed upon the cells within the reservoir 418.

Figure 14:
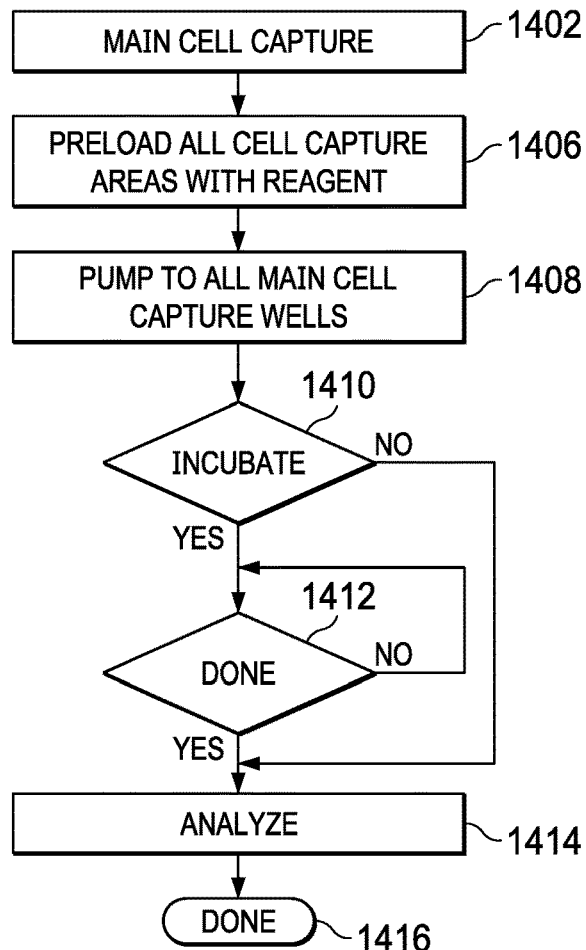
FIG. 14 illustrates a flowchart for the main parallel stage of analysis.

Referring now to FIG. 14 come there is illustrated a flowchart for the parallel cell capture in the first testing/analysis stage. This is initiated at a block 1402 and a process and proceeds to a block 1406 in order to preload all of the cell capture areas having reagent associated there with, such that the portion of the biofluid stored in the reservoir 418 is transferred to the reservoirs associated with the parallel cell capture areas. The process enclosed a block 1408 wherein the pump is activated to fill all of the cell capture wells associated with this stage of testing/analysis. The process then flows to a block 1410 to possibly allow the cells to slowly go through the microchannels in order to interact with the reagent. If so, this requires a certain amount of time and this would result in the micropumps operating at a lower rate to allow sufficient time for the cells to flow through the serpentine microchannels 316 to interface with the particular coating on the surfaces thereof. This basically is the amount of time required for the micropumps to fill up the reservoir 318 associated there with. The length of the serpentine microchannel 316 would determine the amount of time required to fill up the reservoir 318. Once the reservoir has been filled, as indicated by a block 1412, then the viewing window in the reservoir 318 is analyzed, as indicated by a block 1414. The path from the block 1410 to the input of the block 1414 indicates a path by which the micropumps can be run at a higher rate. The process then is terminated at a block 1416.

Figure 15:
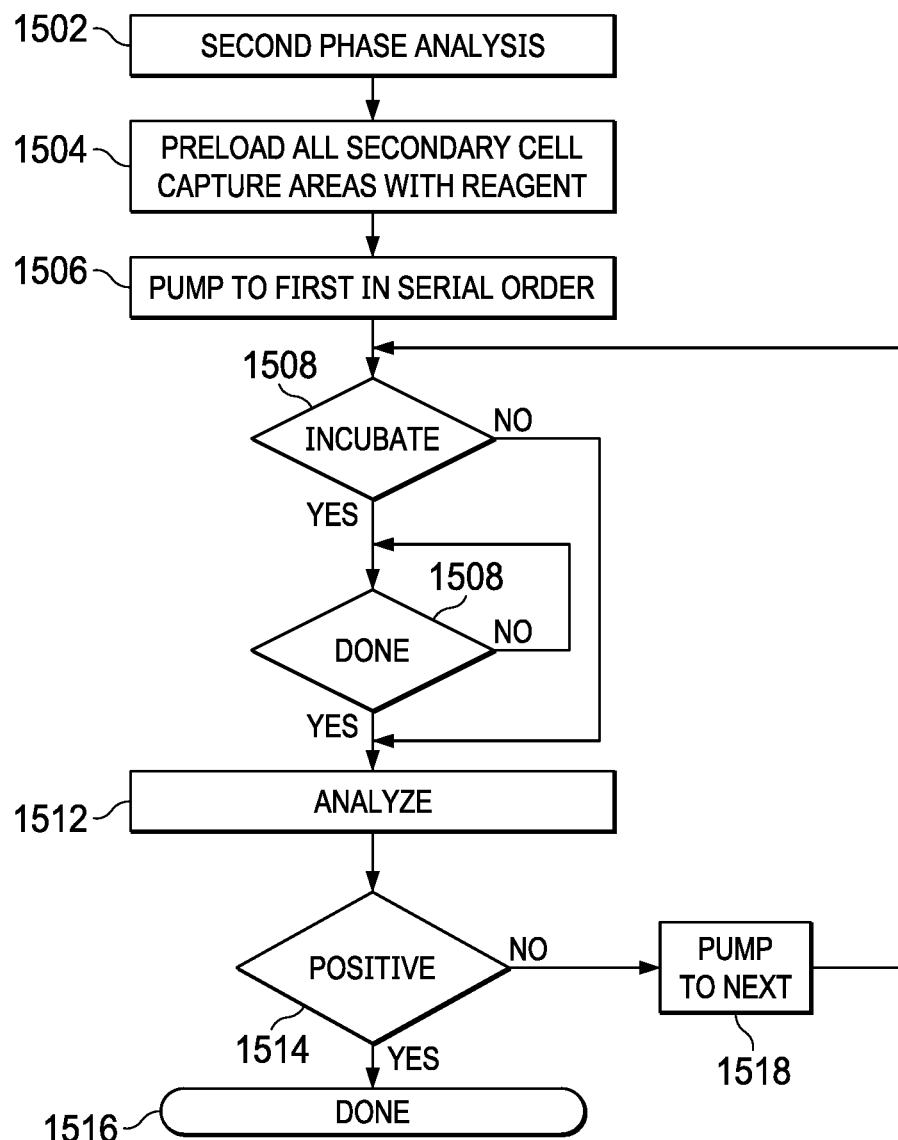
FIG. 15 illustrates the serial stage of analysis.

Referring now to FIG. 15, there is illustrated flowchart for the second phase of the analysis, provided that the first phase indicated a positive result for one of the cell capture areas and the associated reagent. This is initiated a block 1502 and then proceeds to a block 1504 to preload all of the secondary cell capture areas with reagent and into a function block 1506 to pump all of the remaining biofluid material from the reservoir 418 into the first reservoir in the secondary reservoirs 330. This also goes through and incubate step to allow the micropumps to pump at a slower rate to allow the biofluid material to go through the serpentine microchannel 316 at a slower rate before it enters the associated reservoir 318. When the reservoir 318 is filled, as indicate a by block 1510, the contents of the reservoir 318 are analyzed at a block 1512. If the pump can be run at a faster rate, this is provided by a path around the block 1510. If the result is positive, as indicated by a block 1514, then the process is terminated at a block 1516. If not, the process flows from the block 1514 to a block 1518 in order to the next reservoir 330 in the back to the input of the serpentine microchannel 316 and then float the input of the block 1508.

Figure 16:
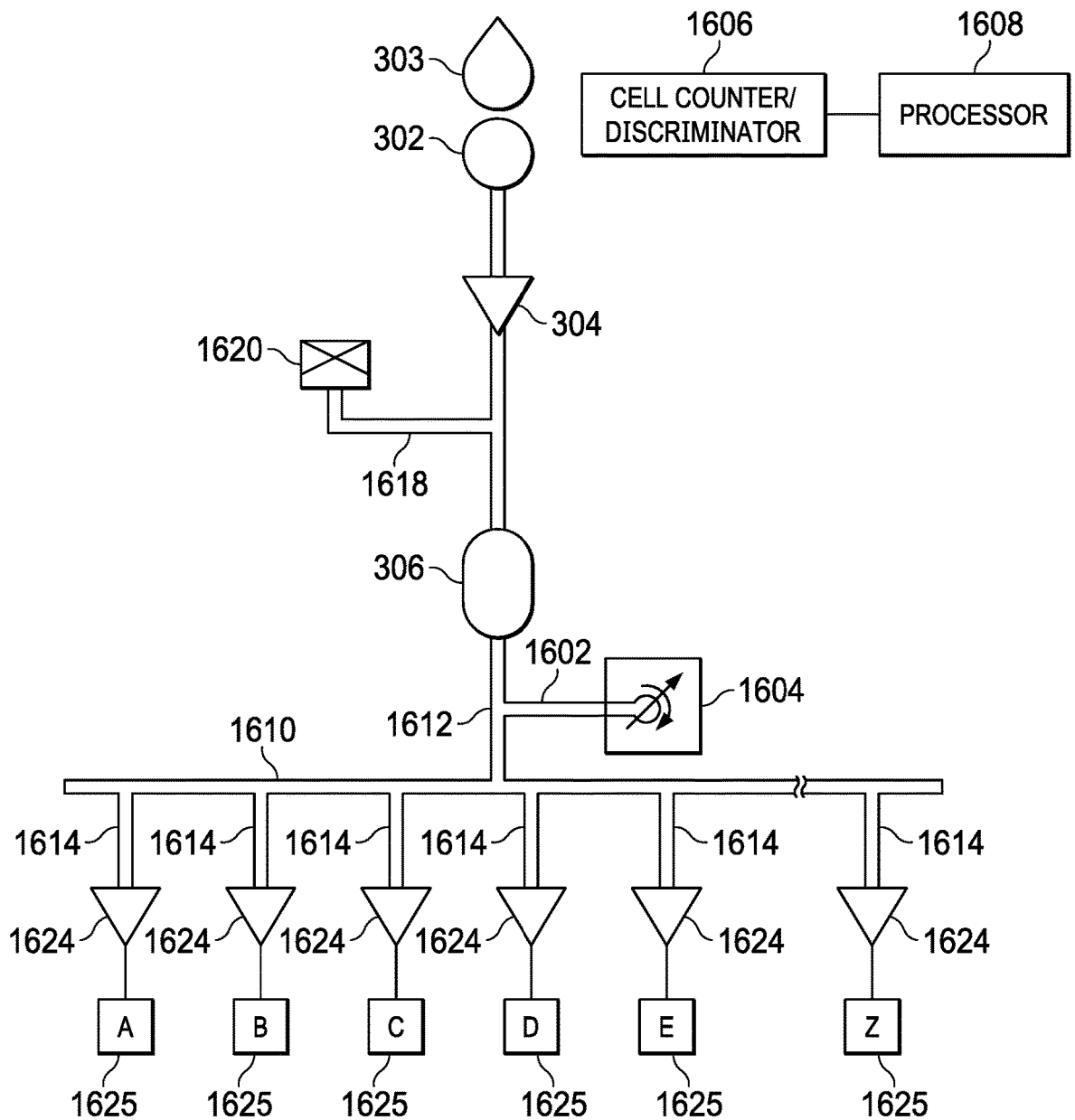
FIG. 16 illustrates a simple fight diagrammatic view of the microfluidics chip.

Referring now to FIG. 16, there is illustrated a simplified diagrammatic view of the microfluidics chip for processing a plurality of modules. The sample 303 is input to the well 302 and then pumped into the viewing window 306. A waste microchannel 1602 is provided an interface to the viewing window 306 that is interfaced with a micro valve 1604 to allow air to escape, or any bubbles that may be present, from the viewing window 306. Additionally, the waste microchannel 1602 could interface with an external vacuum source aid in fluid flow. A cell counter/discriminator 1606 is provided for optically viewing the contents of the viewing window 306, the output thereof processed via a processor 1608. The outlet of the viewing window 306 is interfaced with a manifold microchannel 1610 through a connecting channel 1612. At this point, the micro valve 1604 is closed such that the biofluid contained within the viewing window 306 and the interfaced with microchannel manifold 1610 to allow fluid to be pump therefrom to a plurality of distribution paths along distribution microchannels 1614. It may be that pump 304 would need to be activated in order to reduce the pressure at the upper end of the viewing channel 306 or, alternately, a microchannel 1618 interfaced with a micro valve 1620 could be provided to, when open, relieve the pressure in the upper end of the viewing window 306 to allow biofluid to be pumped therefrom to the microchannel manifold 1610.

Each of the distribution microchannels 1614 is interfaced with a separate module via an associated distribution pump 1624 to interface with and associated one of modules 1625, labeled A-Z, for example. There can be any number of modules provided. However, each module 1625 has associated there with a finite capacity and, therefore, the number of modules 1625 that can be interfaced to the viewing window 306 is a function of the volume of biofluid contained therein and the capacity of the reservoirs of each of the individual modules 1625, each of the individual modules 1625 potentially having a different capacity, depending upon the configuration thereof. However, selecting among the various distribution pump 1624 can allow desired tests to be done with the available biofluid contained within the viewing window 306.

Figure 17:
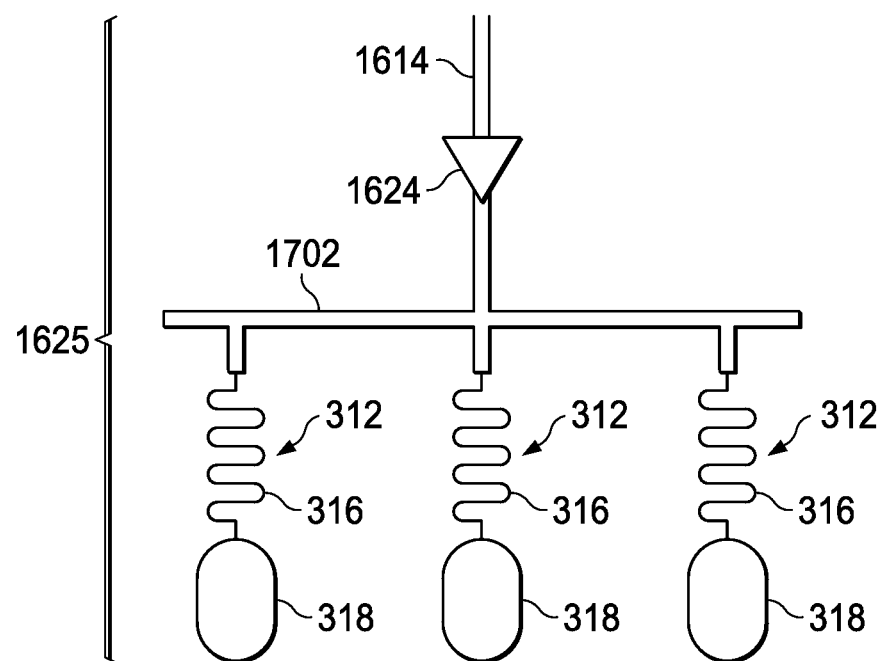
FIG. 17 illustrates a simplified diagrammatic view of a parallel module.

Referring now to FIG. 17 there is illustrated a diagrammatic view of one of the modules 1625 associated with the parallel testing configuration, wherein biofluid is loaded into a plurality of testing reservoirs. The distribution pump 1624 associated there with transfers fluid from the distribution microchannels 1614 to an intermediate microchannel manifold 1702 which is then interface with a plurality of testing reservoirs 312, as described hereinabove. Each of these testing reservoirs has a serpentine microchannel 316 and a viewing window 318 associated there with. As described hereinabove, each of these testing reservoirs can have a different volume and a different configuration mechanically and can be associated with a different test. They can each have a particular coating of reagent, such as an antibiotic, to interact with the biofluid for testing purposes to determine if there is any reaction of the biofluid in the cells contained therein to the material coated on the sides of the serpentine microchannels 316. In the operation of this particular module 1625, all of these testing reservoirs 312 are associated with different reagents and will be loaded in parallel. For this embodiment, will be desirable for each of the reservoir 312 to have the same volume. If, however, they had different volumetric capacities, it would be necessary to have some type of waste gate with a micro valve to allow all of the viewing windows 318 to achieve full capacity.

Figure 18:
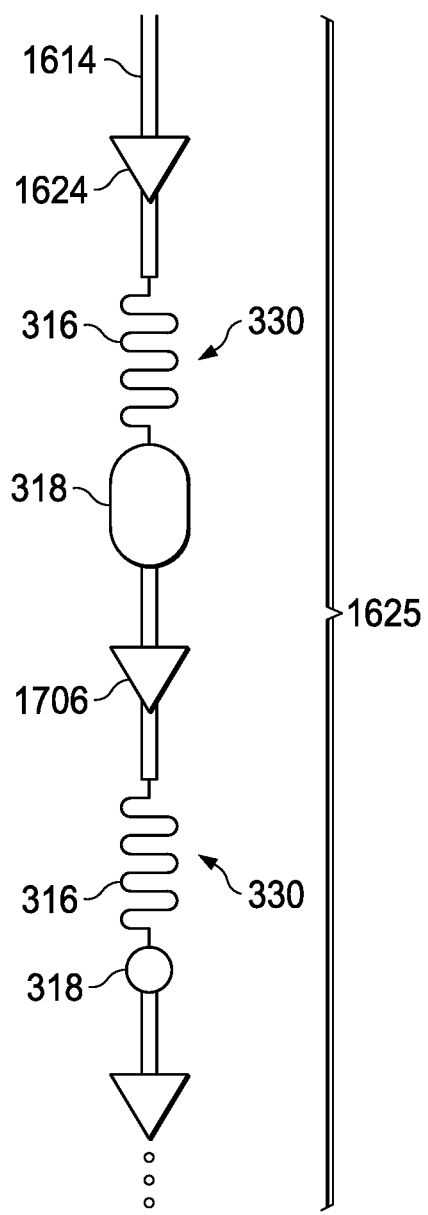
FIG. 18 illustrates simplified diagrammatic view of a serial module.

Referring now to FIG. 18, there is illustrated a diagrammatic view of the serial wherein a plurality of testing reservoirs 330 is arranged in a series configuration. In this configuration, the associated distribution pump 1624 will transfer biofluid from the microchannel manifold 1610 through the distribution microchannels 1614 to the first of the testing reservoirs 330. The biofluid will be contained within the viewing chamber 318 and, as noted hereinabove, there will be possible he some type of waste microchannel associated micro valve to allow air/bubbles to escape during filling of the viewing window 318. Thereafter, a second serial pump 1706 is activated to transfer the contents of the viewing window 318 to a second testing reservoir 330 in the associated serpentine microchannel 316 and viewing window three eight teen. In this transfer, there may be required a relief microchannel (not shown) at the inlet end thereof to reduce the pressure therein during the pumping operation. This will continue until all of the tests have been done. Each of the serpentine microchannels 316 associated with each of the testing reservoirs 330 will have a graduated increase in the particular reagent to determine the dosage, in this example. It may be that, upon being exposed to the dosage of the reagent in the first testing reservoir 330 that cellular material in the biofluid is somewhat affected by the reagent, i.e., the antibiotic, for example. By moving to a higher concentration of the reagent in the next sequential testing reservoir 330, this could be accounted for in the overall analysis. It may be that the actual concentration in the next sequential testing chamber 330 is not an exact incremental increase in the reagent. For example, if it was desired to expose the biofluid to reagent increments of 10%, 20%, 30%, etc. in 10% increments, it may be that the first testing chamber 330 has a concentration of 10% and then the second testing chamber has a concentration of possibly 16%, accounting for the fact that the accumulated effect of passing through the 10% testing chamber 330 and the 16% testing chamber 330 effectively provides a 20% accumulated exposure in the second testing chamber 330 and so on.

Figure 19:
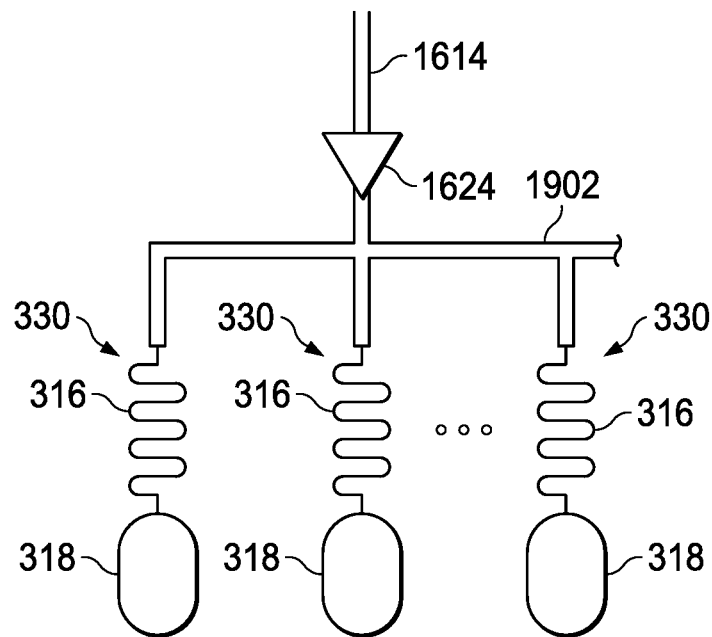
FIG. 19 illustrates a simplified diagrammatic view of a serial module arranged in parallel.

Referring now to FIG. 19, there is illustrated a diagrammatic view of a configuration for providing parallel loading of the serial configuration for the incremental testing. This is similar to the embodiment of FIG. 17, except that the testing chambers 330 are all interfaced with the associated distribution pump 1624 through a microchannel manifold 1902 in a parallel configuration, such that they are all loaded at the same time, with each having a different concentration of reagent associated therewith. In this configuration, however, since all of the testing chambers 330 will be loaded in parallel, there are required to be a sufficient volume of biofluid contained within the viewing window 306 initially to facilitate complete filling of each of the associated viewing windows 318.

Figure 20A:
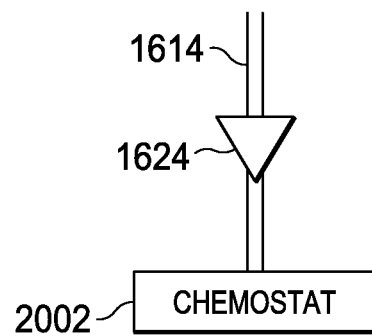
FIGS. 20A and 20B illustrated a diagrammatic view of an embodiment utilizing a chemostat.
Figure 20B:
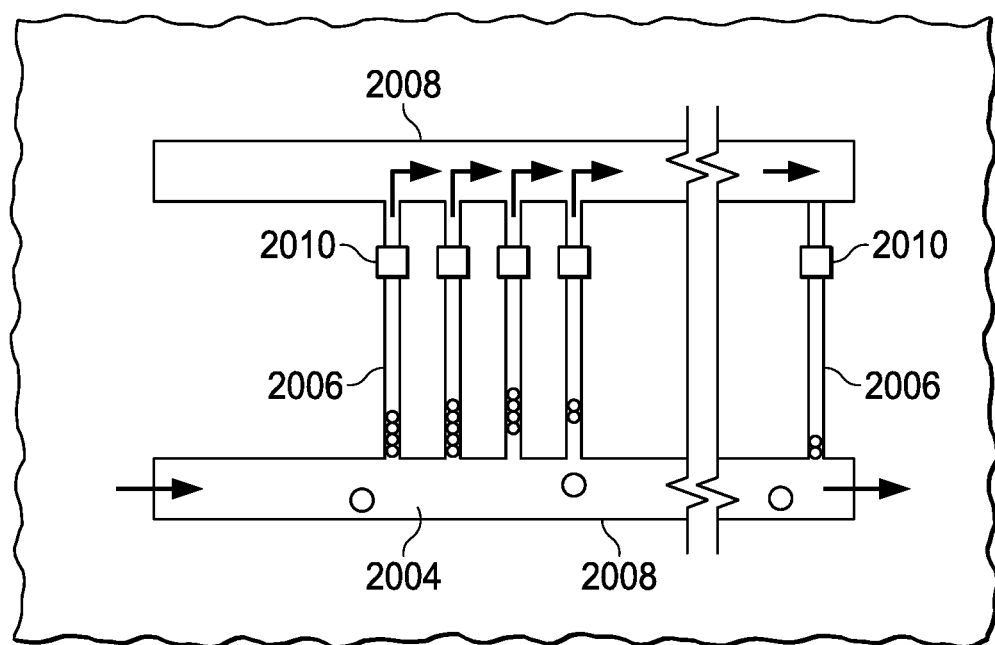

Referring now to FIGS. 20A-20B come there is illustrated a diagrammatic view of chemostat, wherein the associated distribution pump 1624 transfers biofluid from the distribution microchannel 1614 two eight chemostat 2002. The details of the chemostat 2002 are illustrated in FIG. 20B. A main microchannel 2004 is interfaced on one and thereof with the output of the distribution pump 1624 associated there with, with the other end of the microchannel 2004 interfaced with a waste gate via a micro valve (not shown). There are a plurality of cell storage microchannels 2006 connected between one surface of the main microchannel 2004 and a waste microchannel 2008. Each of these cell storage microchannels 2006 associated there with a filter 2010 disposed at the end thereof proximate to the waste microchannel 2008. Each of the cell storage microchannels 2006 has a size that will receive a particular target cell having a particular dimension, such that the target cell will flow into the cell storage microchannel and cells of smaller size will pass through the associated filter 2010, which filter 2010 is a microchannel with a diameter that is smaller than that of the target cell. This waste material will flow out through the waste gate or micro valve (not shown) associated with the waste microchannel 2008. By maintaining a pressure differential between the main microchannel 2004 and the waste microchannel 2008, the target cells will be stored within the cell storage channels 2006. Larger cells than the target cells in the main microchannel 2004 will bypass the cell storage microchannels 2006 and pass out of the waste gate associated with the main microchannel 2004, keeping in mind that there is required to be a lower pressure within the waste microchannel 2008 as compared to the main microchannel 2004.

Figure 21:
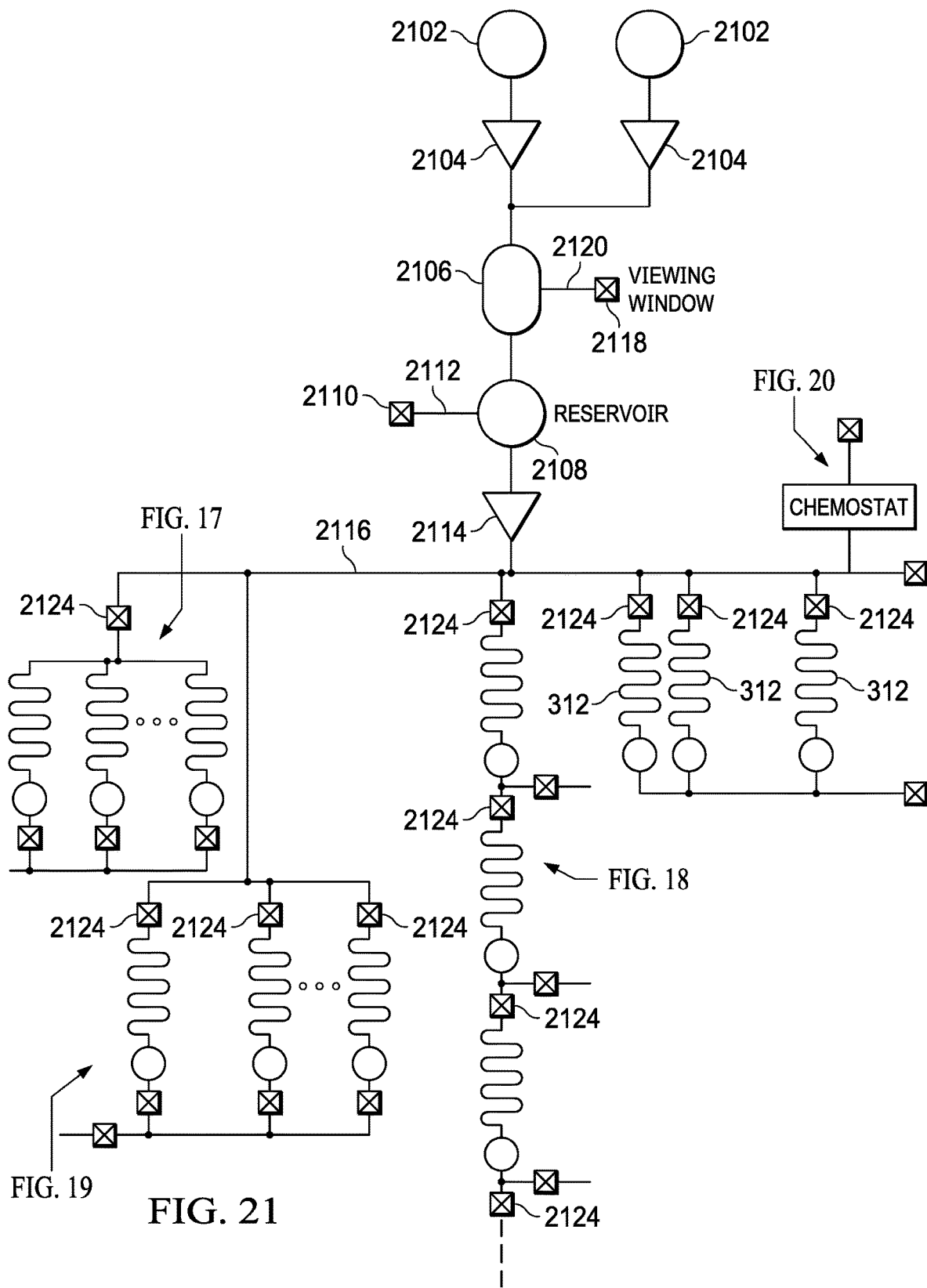
FIG. 21 illustrates a diagrammatic you have the microfluidics chip utilizing valves.

Referring now to FIG. 21, there is illustrated an embodiment of the microfluidic chip utilizing micro valves as opposed to intermediate micropumps. In this embodiment, there are illustrated a plurality of input wells 2102 for interfacing with an initial micropump 2104 to pump fluid through a viewing window 2106 to a first reservoir 2108. Having multiple wells 2102 allows multiple samples to be input through the viewing window 2106 or to actually mix two different materials together for flowing through the viewing window 2106 to the reservoir 2108. The waste gate 2110 can be provided at the reservoir connected thereto via a waste microchannel 2112 to allow air/bubbles to escape. A micropump 2114 is operable to pump fluid from the reservoir 2108 to a main microchannel manifold 2116. During this pumping operation, some type of pressure relief is required which can either be provided via one of the pumps 2104 being activated or a relief micro valve 2118 Interface with the input end of the viewing window 2106 through a relief microchannel 2120.

Interfaced with the main microchannel manifold 2116 is a plurality of distribution micro valves 2124. These distribution micro valves 2124 can be interfaced with various modules, as described above herein with respect to FIGS. 17-20A/b. The only difference is that the associated distribution pump 1624 has been replaced by a distribution valve 2124. Additionally, each of the parallel loaded testing reservoirs 312 can be individually associated with one of the distribution valves 2124 to selectively certain ones thereof for testing. Since each one of these testing reservoirs 312, after selection, is required to be completely filled, by allowing individual selection of the testing reservoirs 312, certain ones thereof can be eliminated. It may be that, in pre-analyzing the biofluid sample, it can be predetermined that certain ones of the associated reagents in the reservoir 312 are not required the testing/analysis step and can therefore be eliminated from the step of filling. This is opposed to the embodiment of FIG. 17, wherein all of the testing reservoirs 312 are complete the filled.

Figure 22A:
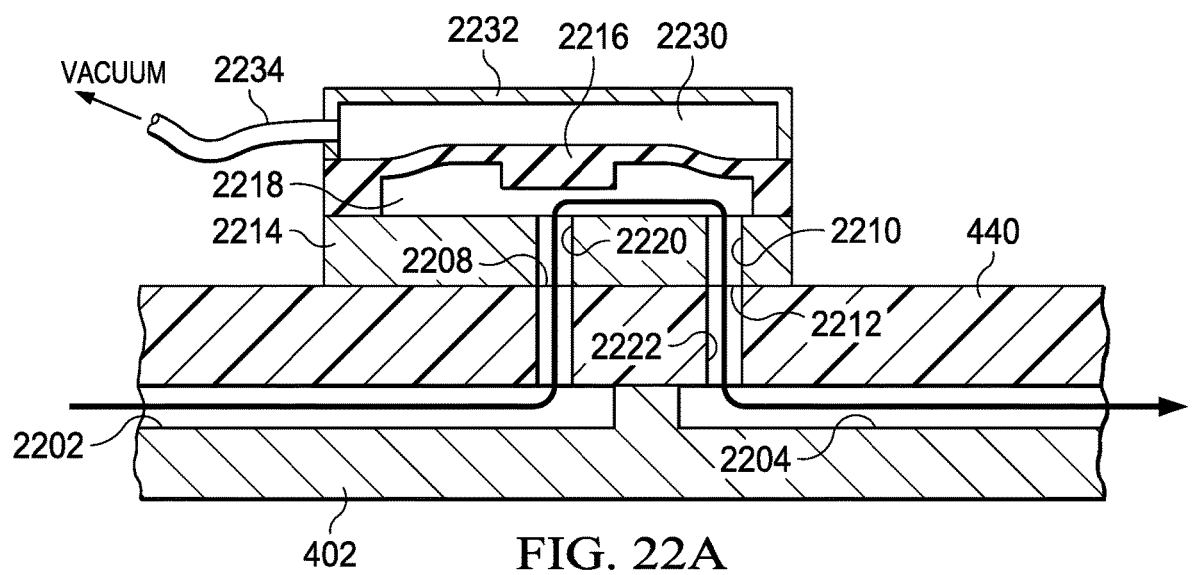
FIGS. 22A and 22B illustrate cross-sectional views of a micro valve.
Figure 22B:
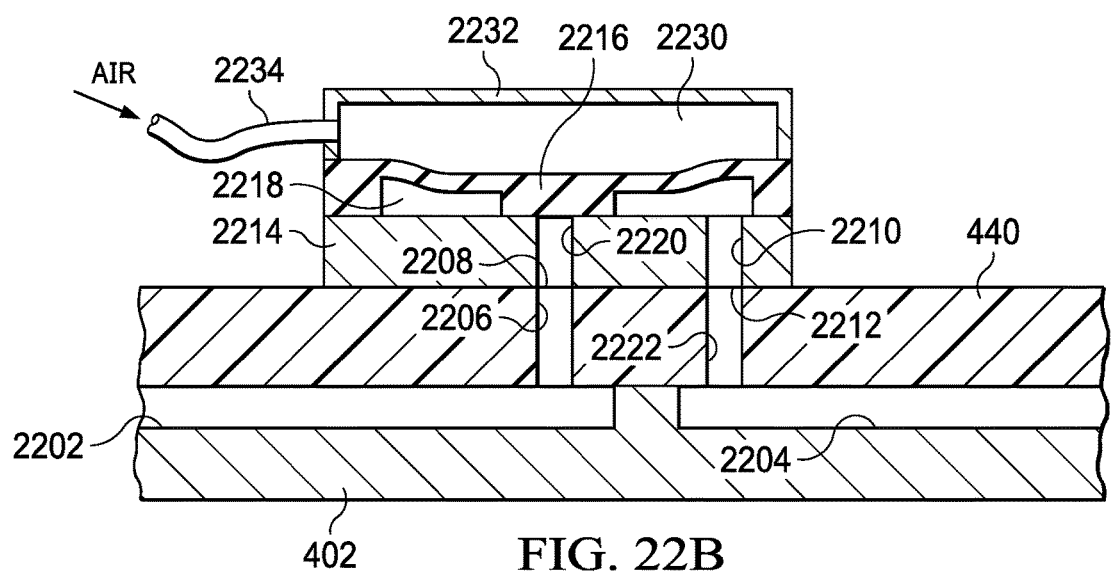

Referring now to FIGS. 22A-22B, there is illustrated cross-sectional views of a micro valve in an open and a closed position. The substrate 402 has cover plate 440 disposed on top thereof. There are provided to microchannels 2202 and 2204 that are to be connected together with the micro valve. The microchannel 2202 is interfaced with a hole 2006 to the surface of the cover plate 440 to an opening 2208. The microchannel 2204 is interfaced to a hole 2210 to an opening 2212 in the cover plate 440. The micro valve has a fixed body 2214 with a membrane 2216 disposed on the surface there above to define a pumping chamber 2218. The pumping chamber 2218 has a hole 2220 interfacing the pumping chamber 2218 with the opening 2208 on the cover plate 440. Similarly, the hole 2212 is interfaced to the pumping chamber 2218 through a hole 2222. The membrane 2216 is operable to reciprocate away from the surface of the fixed body 2214 exposing the top of the hole 2220 in the pumping chamber 2218 to allow fluid to flow through the pumping chamber 2218 and down through the opening 2222 through the cover plate 440 and through to the microchannel 2204. In the closed position, the membrane 2216 is forced down against the upper end of the hole 2220. A pneumatic cavity 2230 is disposed above the membrane 2216 in a housing 2232 and interfaces with a pneumatic source through a hose 2234. Thus, by drawing a vacuum in the pneumatic cavity 2230, the membrane 2216 will be pulled away from the hole 2220 to allow fluid to flow and, when pressurized air is forced into the pneumatic cavity 2230, and the membrane 2216 is forced down to the surface of the fixed body 2214 to seal the opening 2224 in a closed position.

Figure 23:
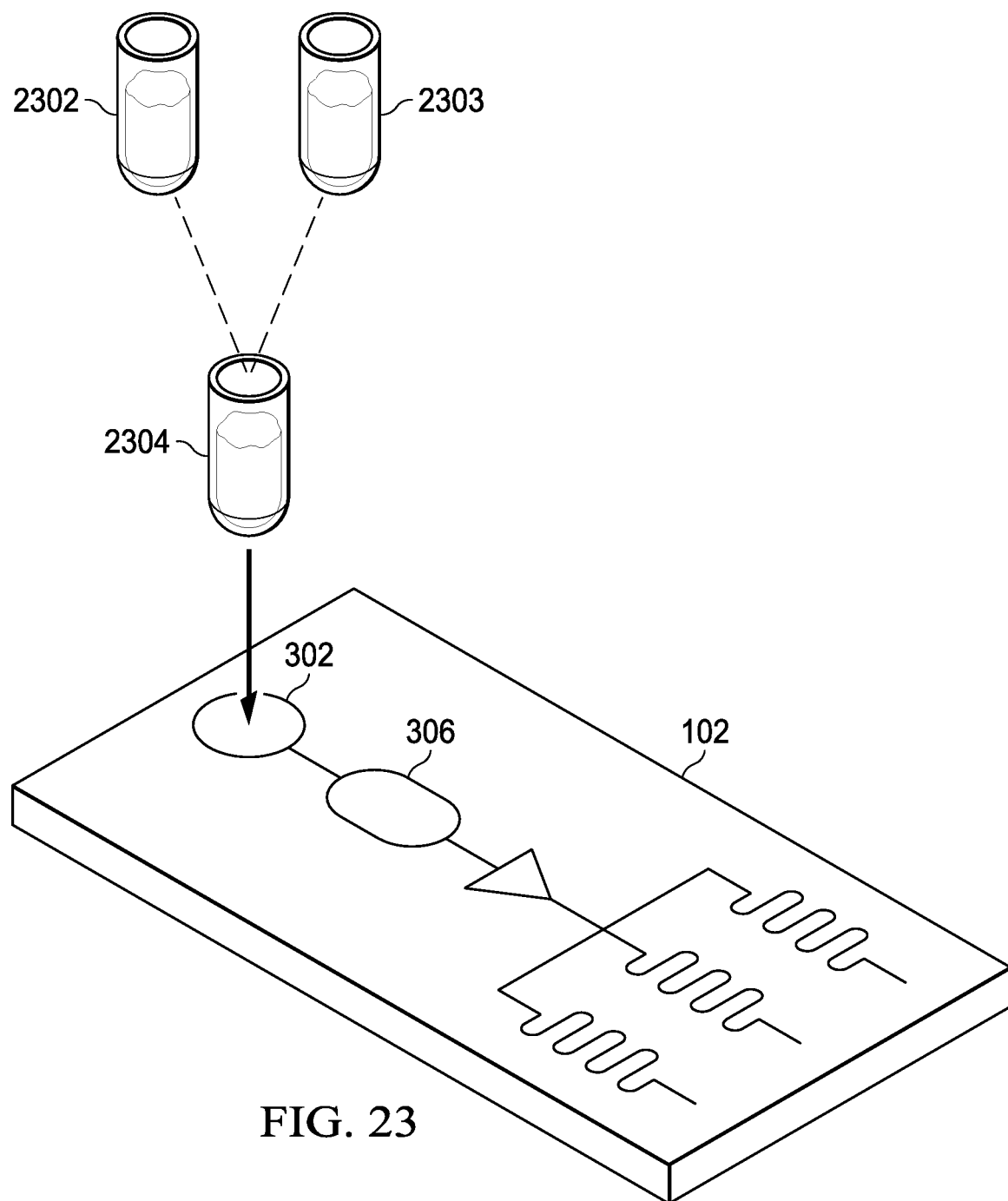
FIG. 23 illustrates a diagrammatic view of preparing a biologic sample and disposing it in the well on the microfluidic chip.

Referring now to FIG. 23, there is illustrated a process flow for preparing the biologic sample for the microfluidic chip 102. The preparation of the biologic sample can take many forms. In this example, the raw biologic sample can be preprocessed, depending upon the type of sample that is being considered. For example, if blood is being tested, the Complete Blood Count (CBC) can be determined, as well as the White Blood Cell Count (WBC), the liver functions and the kidney functions. For urinalysis, the sample can be prepared for testing for WBC's and nitrates, as well as proteins and Bilirubin. There are many well-known processes for preparing biologic samples prior to testing. Once the biologic sample has been prepared a, affinity labels are attached thereto. Typically, there will be a vial 2302 provided with the biologic sample that is mixed with affinity labels in a vial 2303 resulting in the vial 2304 containing a labeled sample. These labels are sometimes referred to as "affinity labels" or "microspheres." These functional polymeric microspheres typically have a diameter of less than 5 µm and have been developed for use with immunological methods. The reagents were initially used as visual markers to identify specific cell types and analyze the distribution of cell surface antigens by scanning electron microscopy. They have also been used, due to their inherent properties, two separate labeled from unlabeled cells by techniques such as centrifugation, a electrophoresis, magnetic chromatography and fluorescence cell sorting. The cells contained within the biologic sample are basically cells bearing defined antigens or receptors, ligands which bind with a high degree of selectivity an affinity to these cell surface sites. The microspheres interact with the specific ligand, which can allow for separation based upon the characteristic properties of the microspheres. This allows for displaying of these labeled cells with the target receptor or antigen with antibiotics or other ligands directly or indirectly bound to the microspheres. Specific types of microspheres or affinity labels can be the type that will fluoresce at a particular wavelength. Thus, specific cells can be identified the optical techniques to identify target cells or differentiate between various types of, for example, bacterial cells and proteins, etc. This labeled sample is then disposed within the well 302 on the microfluidic chip 102 for later processing.

Figure 24:
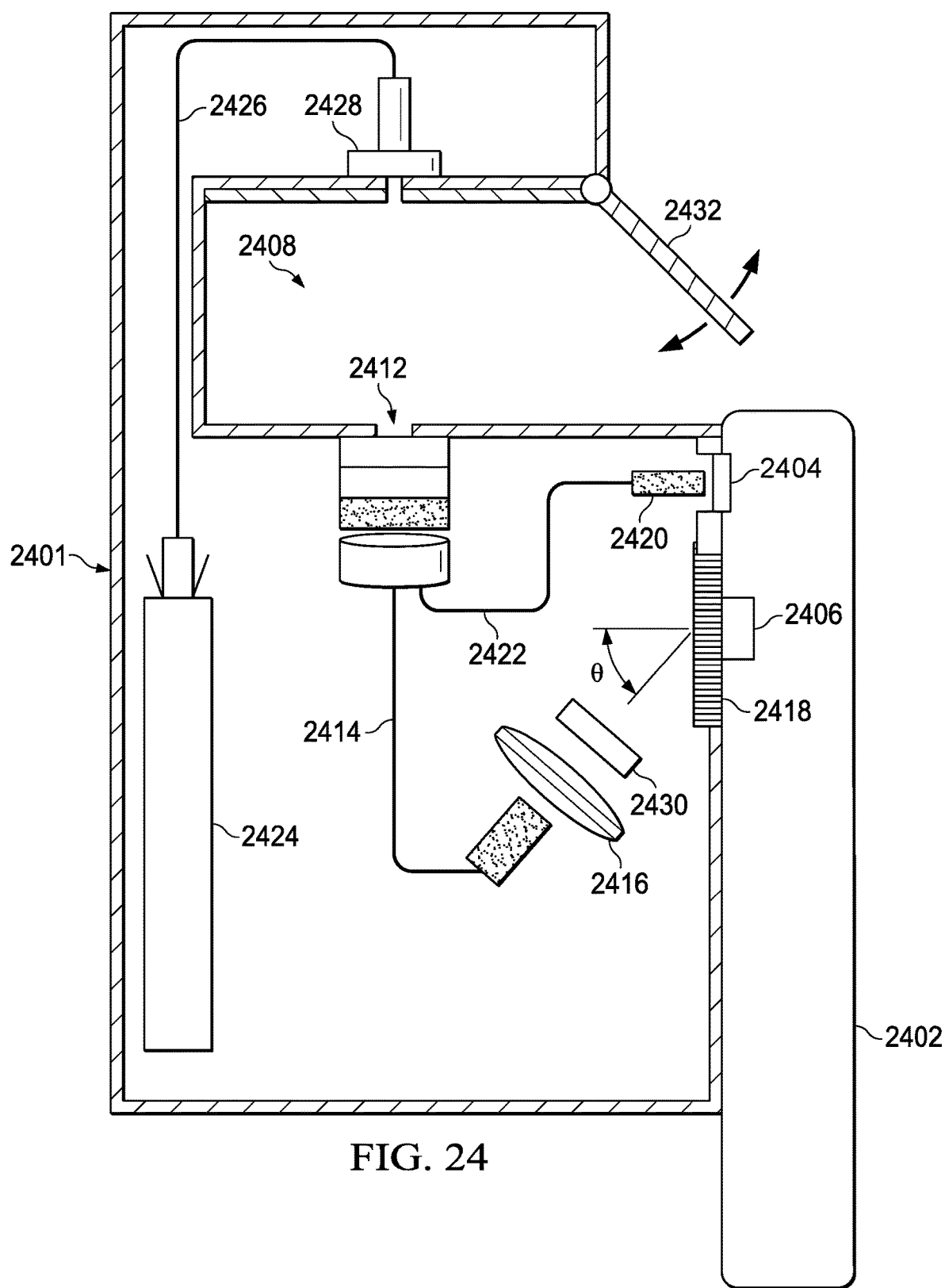
FIG. 24 illustrates a cross-sectional view of an RT-lamp interfaced with a cell phone.

Referring now to FIG. 24, there is illustrated a side cross-sectional view of an RT-lamp. The RT-lamp is a Reverse Transcription Loop-mediated isothermal Amplification device, which is a technique for the amplification of RNA. This combines the advantages of the reverse transcription without of the LAMP technique. The LAMP technique is a single to technique for the application of DNA. This technique is an isothermal nucleic acid application technique, in which a chain reaction is carried out at a constant temperature and does not require a thermal cycler. The target sequences animal five at a constant temperature using either two or three sets of primers and polymerase with high strand displacement activity in addition to a replication activity. The addition of the reverse transcription phase allows for the detection of RNA and provides a one-step nucleic acid amplification method that is used to diagnose infectious diseases caused by bacteria or viruses.

FIG. 24 illustrates an example in which a multimode instrument 2401 is coupled to a smartphone 2402. The smartphone 2402 includes an LED 2404 and a camera 2406. The camera 2406 includes an image sensor, such as a CCD. The instrument 2401 includes a sample chamber 2408 for receiving an optical assay medium. The optical assay medium comprises the labeled biologic sample disposed within the viewing window 306 on the microfluidic chip 102. The sample chamber 2408 may include a door 2432 that prevents stray light from entering.

The optical assay medium is positioned over a detection head 2412 in the sample chamber 2408. The instrument 2401 includes an optical output path for receiving an optical output from the optical assay medium in the sample chamber 2408 via the detection head 2412. The optical output path may include a multimode fiber 2414 that directs light from the detection head 2412 to a cylindrical lens 2416. The optical output path may further include a wavelength-dispersive element, such as a diffraction grating 2418, that is configured to disperse the optical output into spatially-separated wavelength components. The optical output path may also include other optical components, such as collimating lenses, filters, and polarizers.

The instrument 2401 can include a mount for removably mounting the smartphone 2402 in a working position such that the camera 2406 is optically coupled to the optical path, for example, in a predetermined position relative to the diffraction grating 2418. In this working position, the camera 2406 can receive at least a portion of the dispersed optical output such that different locations are received at different locations on the image sensor.

The instrument 2401 may also include an input optical path for directing light from a light source to the optical assay medium in the sample chamber 2408, for example, through the detection head 2412. In some instances, the LED 2404 on the smartphone 2402 could be used as the light source. To use the LED 2404 as the light source, the input optical path may include a collimating lens 2420 that receives light from the LED 2404 when the smartphone 2402 is mounted to the instrument 2401 in the working position. The input optical path may further include a multimode fiber 2422 that directs the light from the collimating lens 2420 to the detection head 2412. The input optical path may also include other optical components, such as collimating lenses, filters, and polarizers.

The instrument 2401 may also include an additional input optical path that directs light form an internal light source, such as a laser 2424, to the optical assay medium in the sample chamber 2408. The additional input optical path may include a multimode optical fiber 2426, as well as collimating lenses, filters, polarizers, or other optical components 2428.

Figure 25:
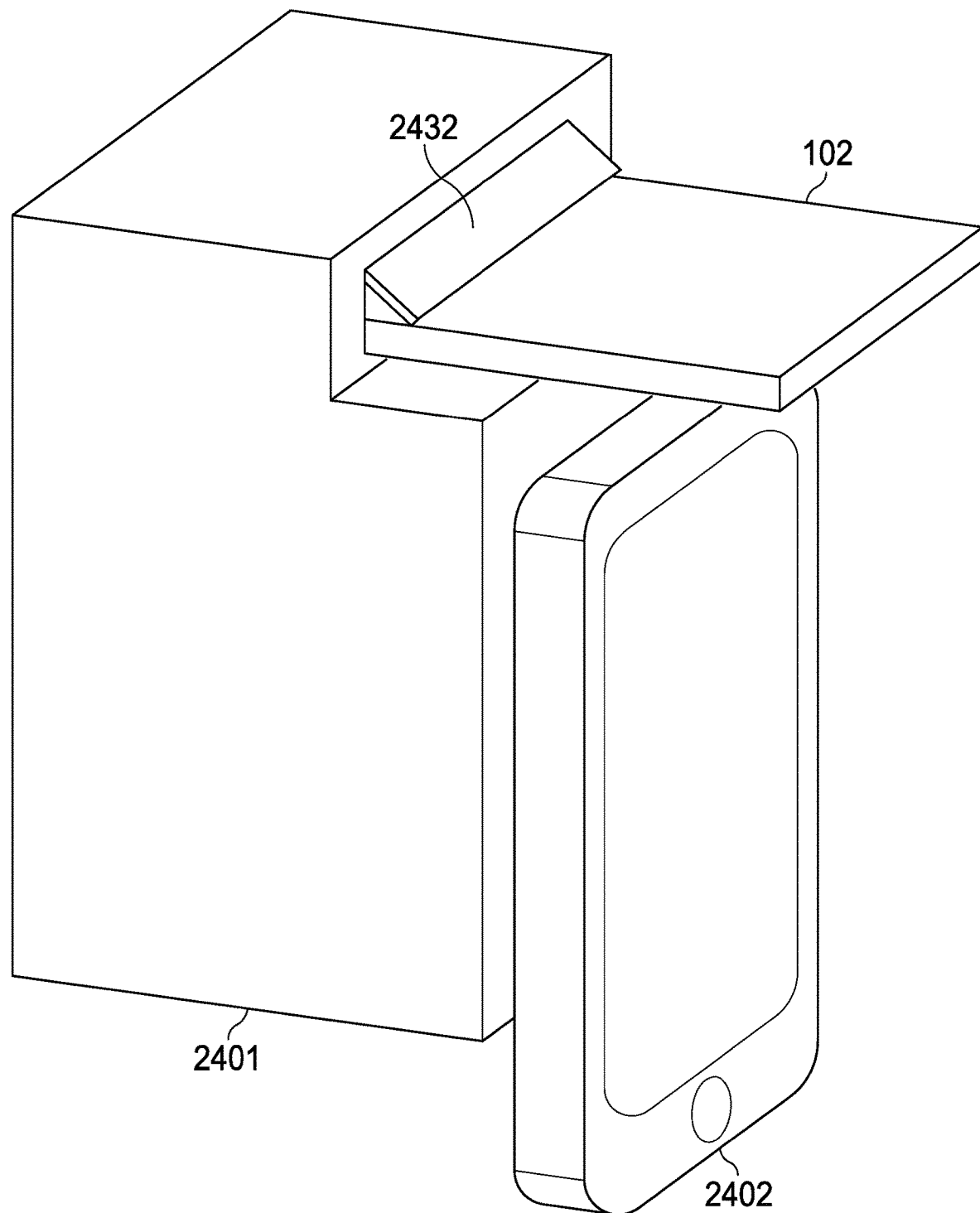
FIG. 25 illustrates a perspective view of the RT lamp interfaced with a microfluidic chip and a cell phone.

Referring now to FIG. 25, there is illustrated the view of the RT-lamp 2401 with a microfluidics chip 102 disposed within the sample chamber 2408.

Figure 26:
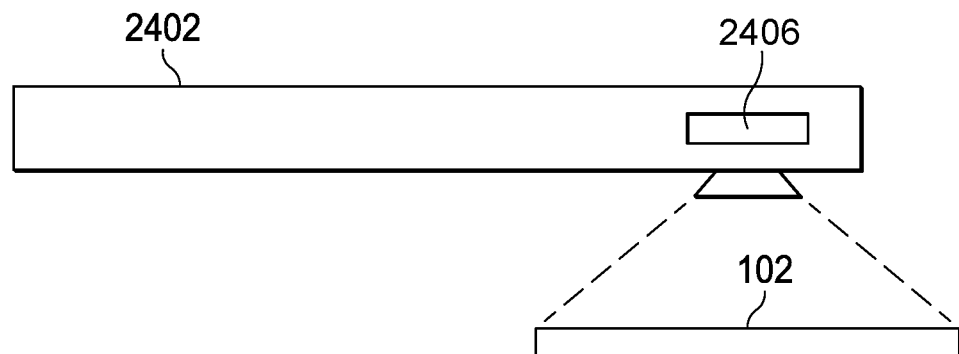
FIG. 26 illustrates a side view of a cell phone interfacing with the micro fluidic chip.
Figure 27:
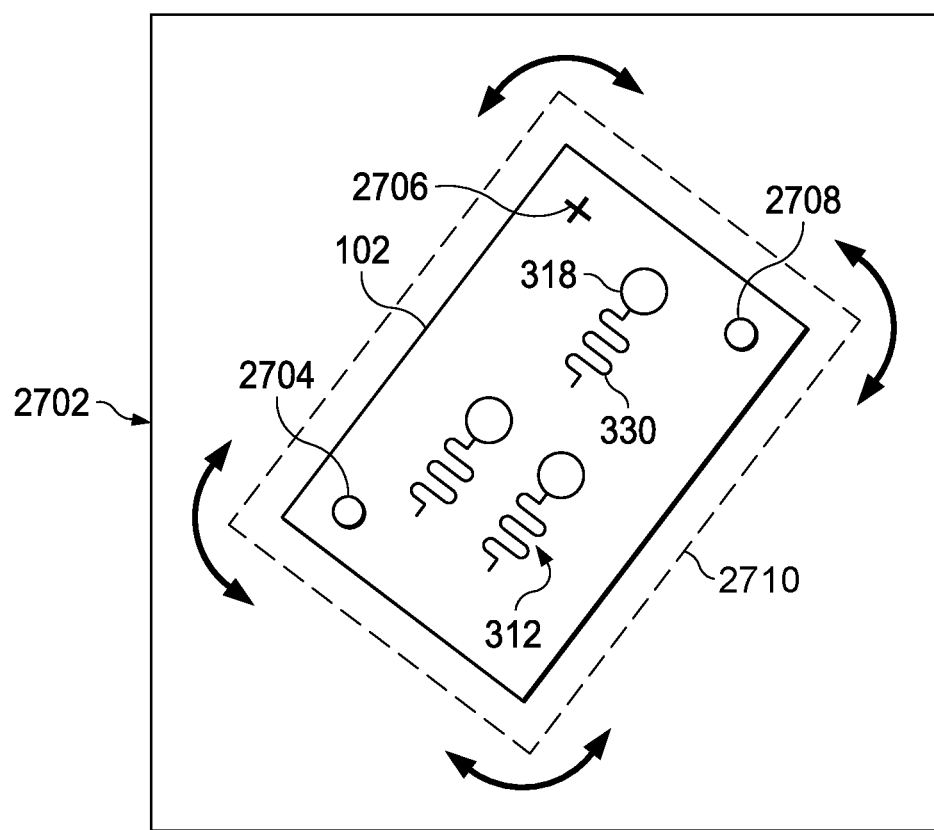
FIG. 27 illustrates a window view of the camera and the alignment process.

Referring now to FIG. 26, there is illustrated a side view of the smart phone 2402 interfaced with the microfluidic chip 102 four imaging the surface thereof, which is illustrated in a window view in FIG. 27. This window view illustrates the viewing window as a box 2702 in which the image of the microfluidic chip 102 is displayed. The application automatic the recognizes various markers 2704, 2706 and 2708 one three corners thereof. This will allow orientation of the window with respect to the application. A box 2710 in phantom dashes will be oriented by the application running on the smart phone 2402. Once the box has been oriented visually about the image of the microfluidic chip 102, then processing can proceed. The processing is basically focusing upon the chip to gain the best optical image of the target sites. The target sites are storage reservoirs 312 and 330, for example. Each of these will have a viewing well 318 associated there with an these viewing wells 318 will have, and one example, a process biologic sample having affinity labels associated there with that fluoresce. By recognizing the florescence, the presence of the cell can be determined. The lack of florescence indicates that the cell, a bacteria for example, has been destroyed. This can be a positive test. By examining at each stage of the testing process the chip, a determination can be made as to results in essentially real time. This will be described in more detail hereinbelow. Once the image is believed to be in focus, then the user can actually take the picture or the application cell can automatically determine that the focus is adequate and take that. This is very similar to character recognition techniques that are utilized in recognizing faces in camera images received by the phone.

Referring now to FIGS. 28A-28H, there are illustrated various images of the microfluidic chip 102 at different stages, this view being a diagrammatic view for simplicity. In this view, there is provided the sample well 2802 which then feeds into the viewing well 2804. As described hereinabove, there are multiple pumps that allow fluid to be moved from the sample well 2802 over to the viewing well 2804 and these are not shown force simplicity purposes. There is provided a multiplexer 2806 which represents the micropumps/valves described hereinabove. The multiplexer 2806 may be associated with one bank 2808 of reservoirs 2802 for the parallel processing stage. These reservoirs 2012 correspond to the reservoirs 312. This requires that the multiplexer 2806 distribute fluid to a microchannel manifold 2810 and one testing phase. The multiplexer 2806 also is connected via a plurality of microchannels to a bank of reservoirs 2814 associated with the serial processing stage to selectively distribute fluid to one of the strings in a second testing phase. This bank of reservoirs includes the reservoirs 330 described hereinabove. Each of these reservoirs 330 is arranged in series such that each has a valve or pump 2816 disposed there between. The multiplexer 2806 also interfaces with a bank 2820 of reservoirs, these, in this example, associated with the serial testing/analysis stage and having reservoirs 330 associated there with. In this example, there are provided five test reservoirs in the bank 2808, wherein each of these test reservoirs has associated there with one serial string of test reservoirs 330 in the bank 2814 and one parallel loaded string of reservoirs 330 in the bank 2820. Additionally, there is a separate testing reservoir 2824 which could correspond to the cell storage area utilizing a chemostat described hereinabove, which is interfaced with multiplexer 2806 through a microchannel 2826.

Figure 28A:
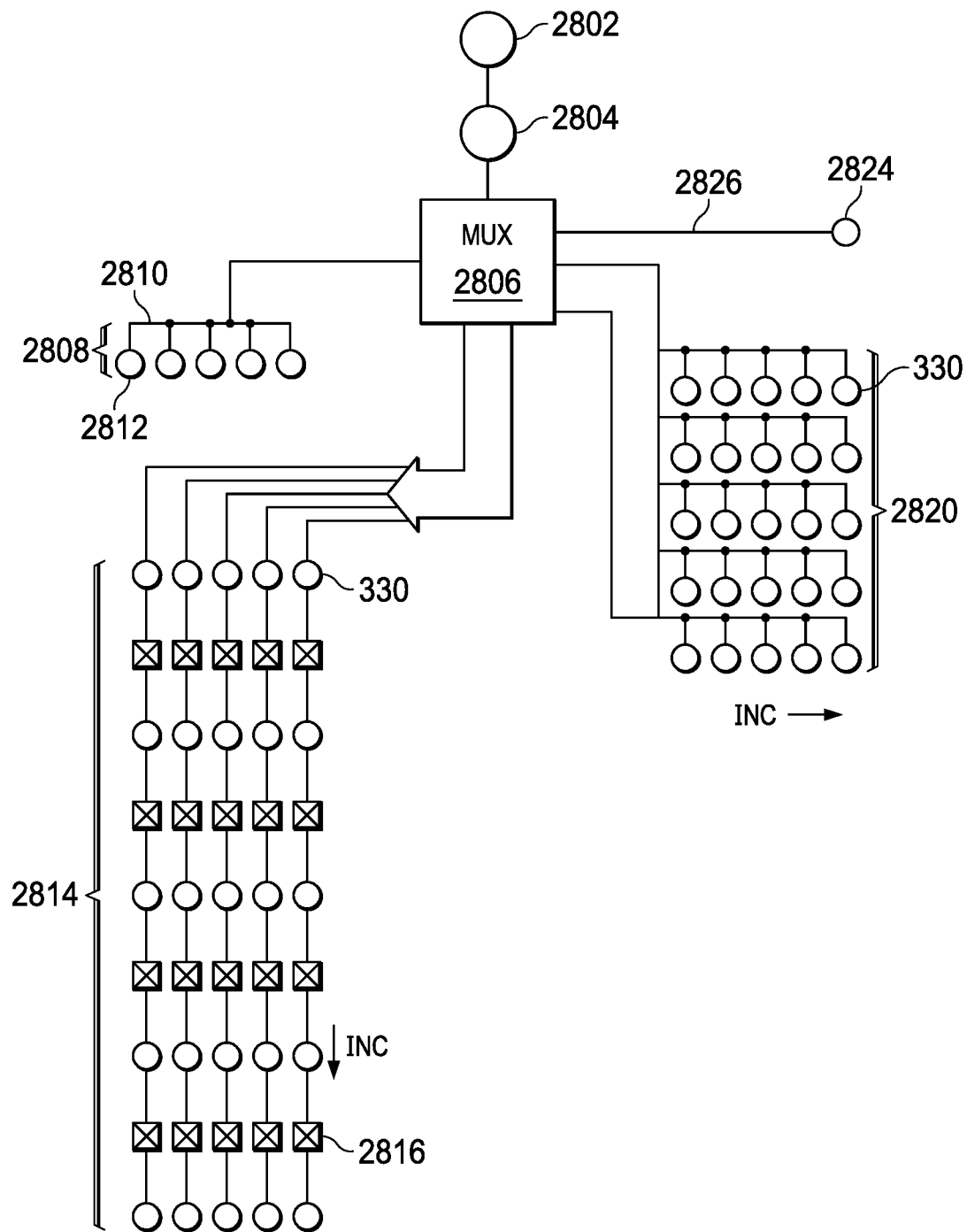
Figure 28B:
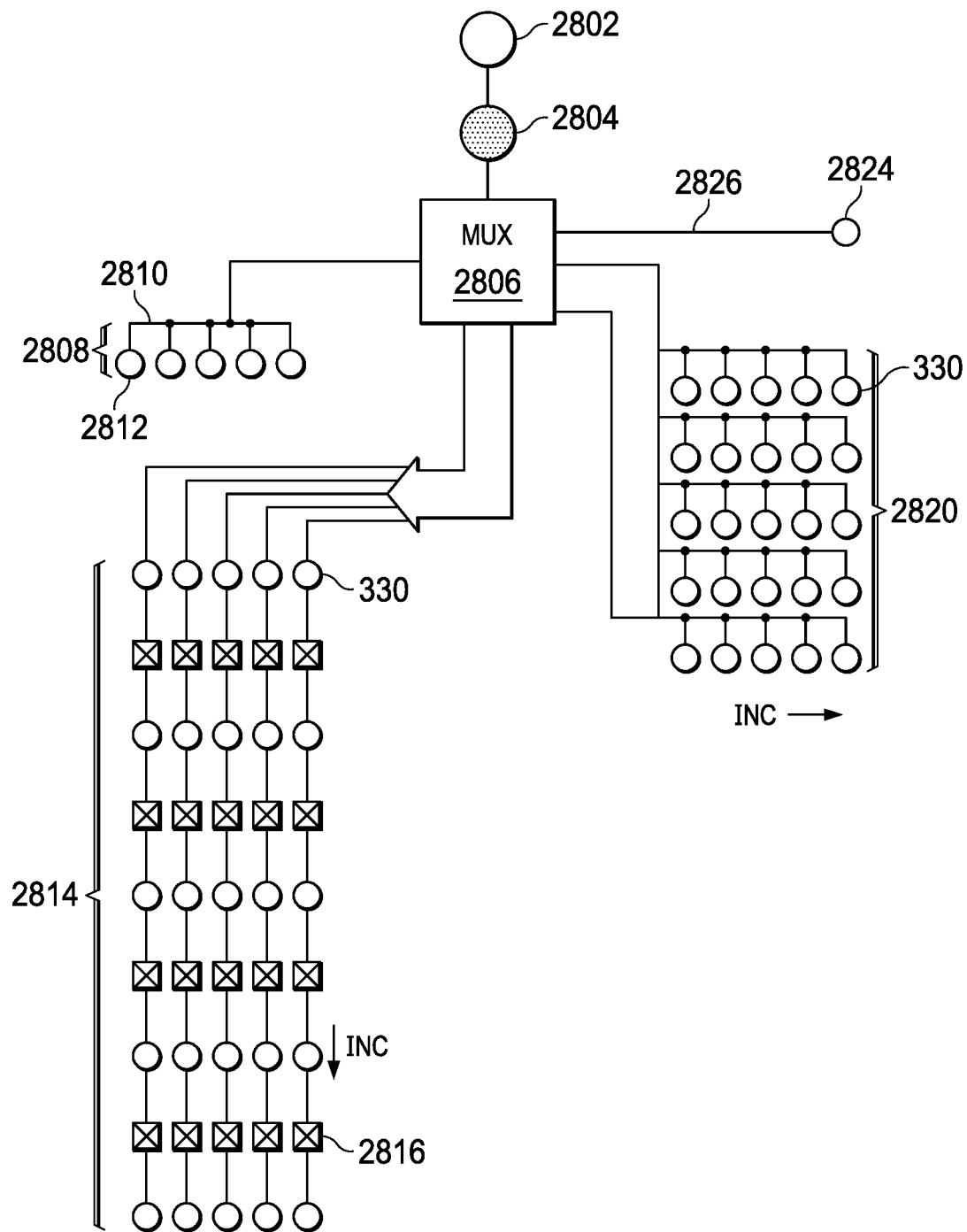

Referring now to FIGS. 28B-28H, there are illustrated various stages of the loading and analysis. FIG. 28B illustrates the first step in the process wherein the biologic sample is loaded into the viewing window 2004. That the step in the process, the microfluidic chip is disposed within the RT lamp 2401 and analyzed to determine the number of cells and the type of cells. If, for example, a certain bacteria were being tested for on this particular microfluidic chip 102, the lack of bacteria cells, as indicated by the particular affinity labels that would be attached to these particular bacteria cells, would indicate that further testing is not required. However, if the correct cells are labeled and the number of cells is at an appropriate level for testing, then the next step of the process is taken.

Figure 28C:
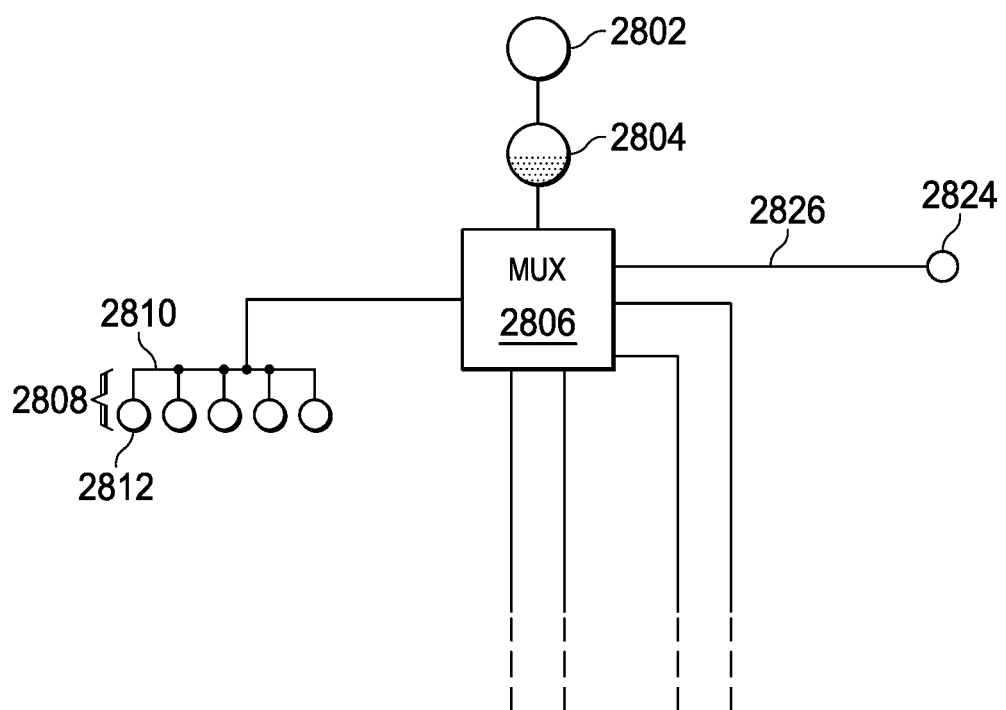

FIG. 28C illustrates a next step of the process wherein a portion of the contents of the viewing well 2804 are transferred to all of the reservoirs 28 one two in the bank 2808, there being five reservoirs 2812 disposed therein, the indirect dies that there could be more reservoirs 2012 provided on the microfluidic chip 102. There will be a certain amount of time required for the pump associated with the multiplexer 2806 to actually move the desire portion of the biologic sample through the manifold 2810 to the reservoirs 2812. As noted hereinabove, each of the reservoirs 2812 corresponds to the reservoirs 312, each having a serpentine microchannel 316 and a viewing reservoir 318 associated there with. The micro pumps associated with the multiplexer 2806 and, nation with the very small widths of the microchannels can require this process to take upwards of 10 or 20 minutes. After this period of time, the microfluidic chip 102 can be imaged to determine if the cells have been destroyed by the coating on the surfaces of the serpentine channel 316. (It should be noted that the viewing well 318 could also be coated). If the cells are destroyed, this indicates that the reagent that coats the walls of the microchannel associated with the reservoirs 312 reacted in a manner indicating self-destruction. However, any visual indication in the viewing wells that can be a vehicle for discrimination between interaction with the particular reagent coating the walls of the serpentine microchannels 316 will provide the ability for a decision to be made as to which reagent is required for further testing.

Figure 28D:
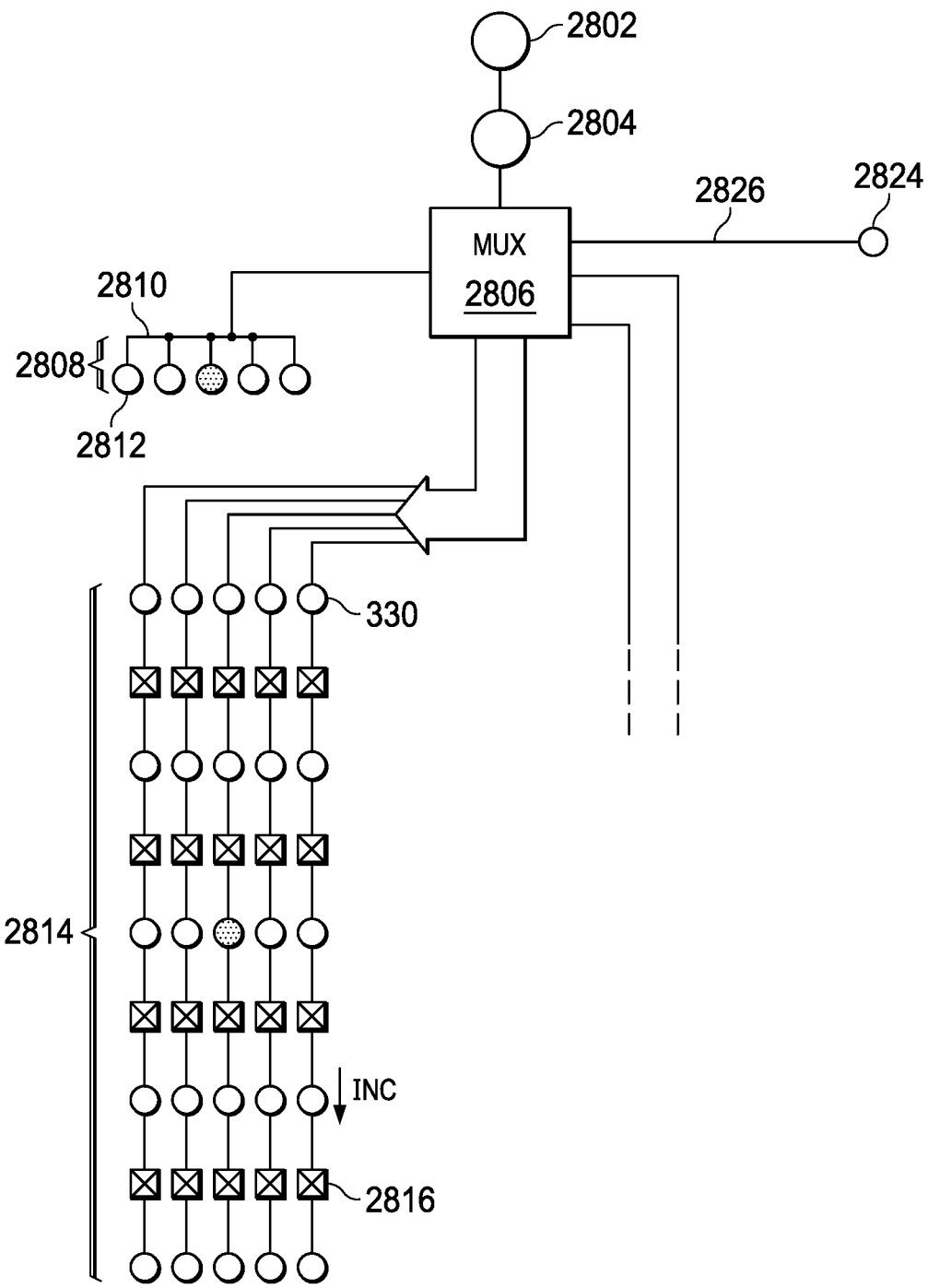

FIG. 28D illustrates the next phase of operation, which is the phase in which the dosage level is term and. In the example above, the middle reservoir in the bank 2808 provided a trigger indication that triggered a decision to then test for dosage in the middle string within the bank 2814. This will require a multiplexer 2806 two only transfer the remaining portion of the biologic sample from the viewing reservoir 2804 into this particular string. As described hereinabove, this process will involve first passing of fluid to the first reservoir 330, which will take a certain amount of time to actually pump the biologic sample through the microchannels into the viewing window 318. This can be a multiphase process, which requires viewing at each stage. In this particular example, the third stage of testing in this middle string in the bank of reservoirs 2814 resulted in a perceivable result, i.e., a lack of florescence, for example. At this point, the image will actually show the perceivable result in both the bank 2808 and in the bank 2814. Thus, in the three phases of testing, the particular cells have been a defined, an indication has been provided as to which of multiple reagents that could possibly provide the desired therapeutic results would be the best choice for the patient and then the third phase of testing provides the actual dosage of that determine reagent. It may be that for ten individuals that had exactly the same symptoms and processed a similarly processed biologic sample for testing in the same way with the microfluidic chip and the RT-lamp 2401 came up with different results. Each individual's particular physiology can vary and, as such, the results could differ. In a typical medical environment, the particular reagent of choice or drug of choice is determined by an individual based upon various criteria. Since the medical professional does not have the test directly in front of them, they might just prescribe, for example, a broad based antibiotic. They might follow that up with testing of a biologic sample in a lab, which could take a number of days just to determine exactly what bacteria is present and what would be the best antibiotic to use in order to attack this particular bacteria. Of course, the broad-spectrum antibiotic might have worked by the time the test results come back. If not, these results might be useful to the medical professional. However, these tests seldom if ever actually focus in on the dosage that would be preferable for a particular individual. If even the particular antibiotic could be identified which was specific to that particular bacteria tested for and found be present in the biologic sample, the dosage prescribed is typically a medium or high dosage, depending upon the criteria that the medical professional utilizes. However, the medical professional typically generalizes the physiology of any individual and maybe filters that based upon age, gender, etc. However, the individual physiology is not taken into account.

With use of the present microfluidic chip 102, the entire testing process can be performed at the Point of Care (POC) in a relatively short amount of time. The result is not only the identification of the best reagent to use but also the dosage. This is all accomplished with a very small amount of biologic sample.

Figure 28E:
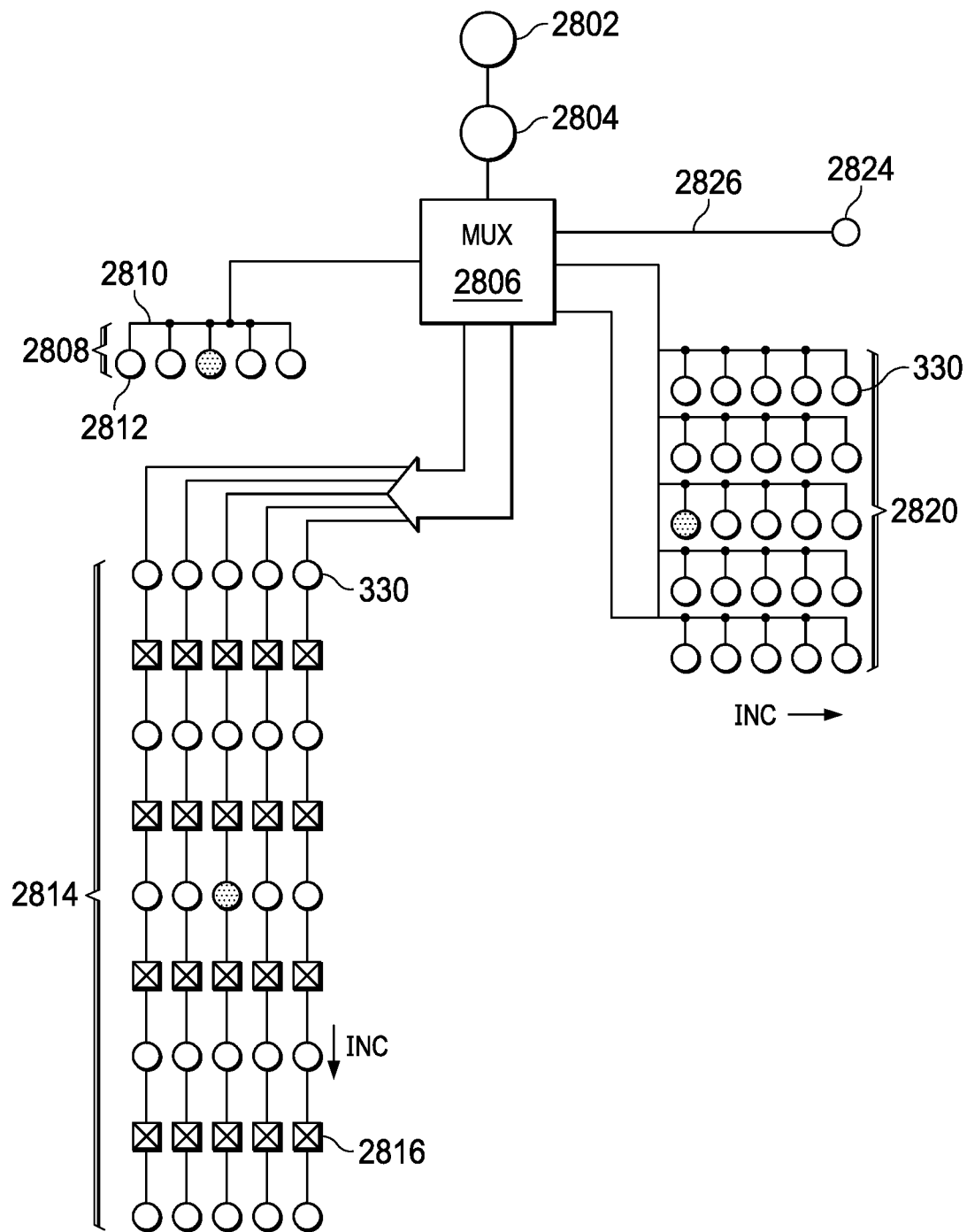

FIG. 28E, there is illustrated a potential further processing that can be provided. In this embodiment, the bank 2820 can have a different modification of the antibiotic that was determined from the test associated with the bank 2808. This modification could be associated with the pH of the antibiotic, wherein it has been determined with respect to some antibiotics that the pH of the antibiotic can affect the efficacy thereof. In this example, it can be seen that the third reservoir with respect to dosage is the one that is selected in the bank 2814 but in the bank 2820, is the lowest dosage. Thus, the multiplexer 2806 needs to first test the bank 2814 and then test the bank 2820. However, it should be understood that both the bank 2814 and the bank 2020 could be identical, either serially loaded or parallel loaded, the commonality being that they have a gradually increasing dose of antibiotics that can be tested for.

Figure 28F:
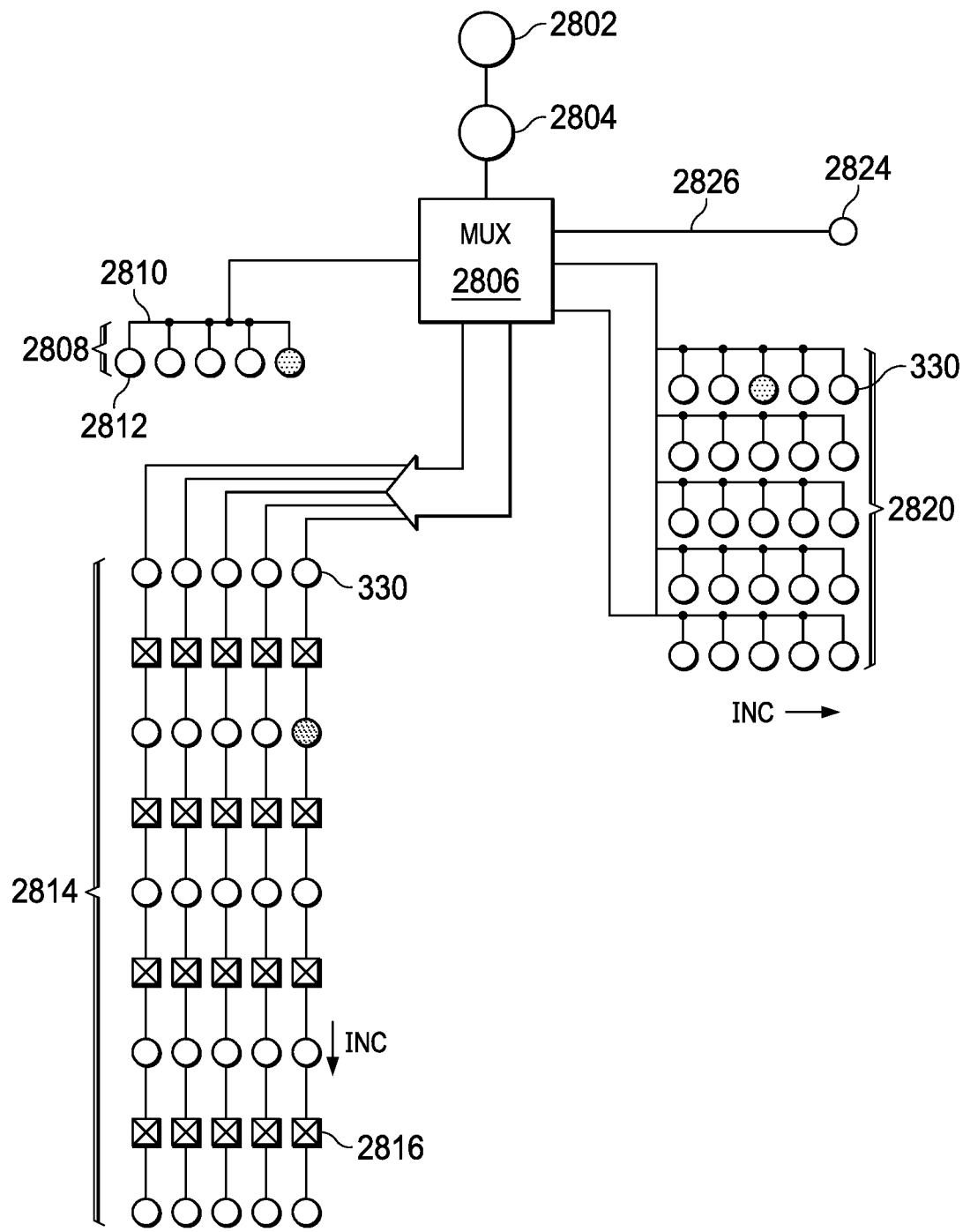
Figure 28G:
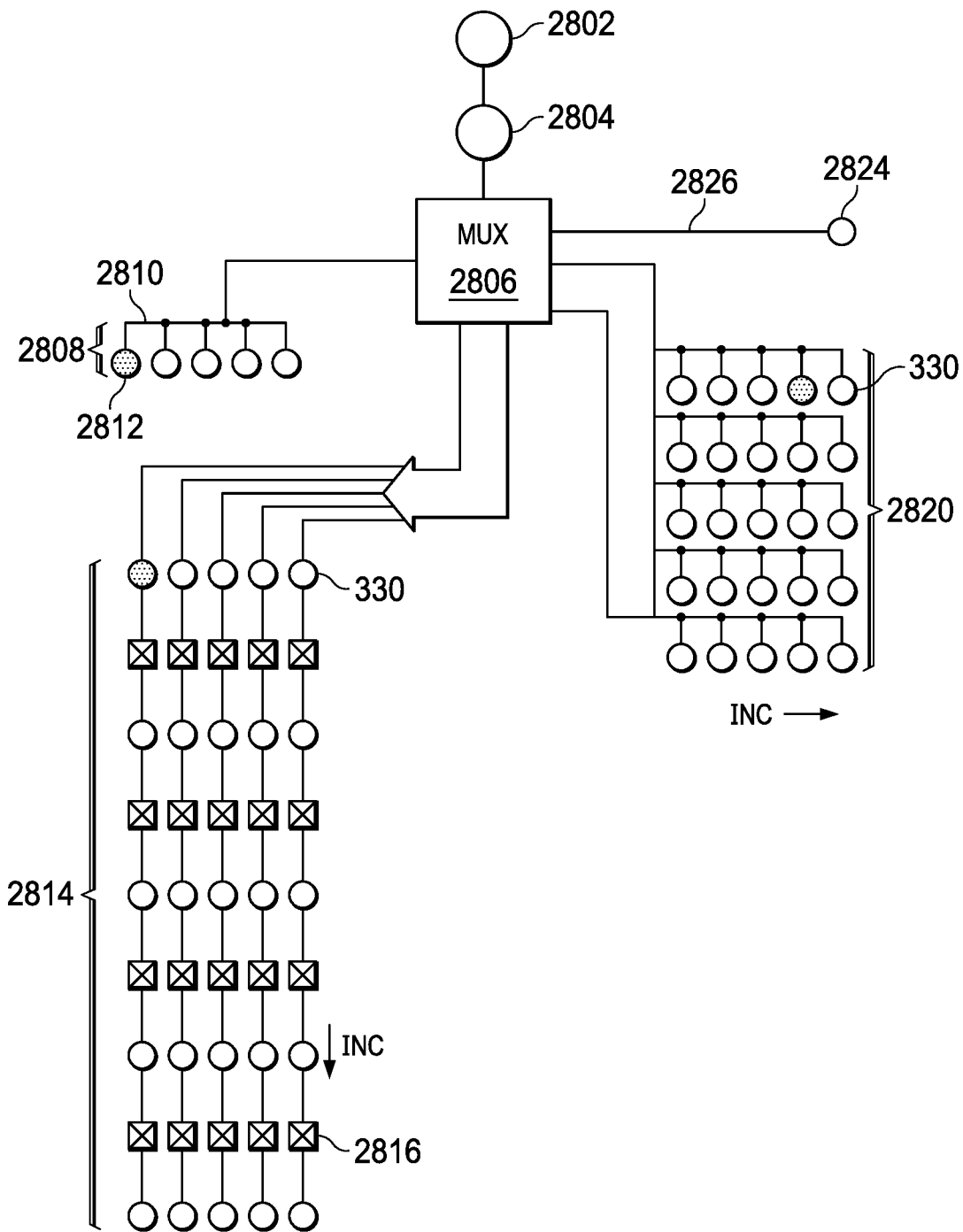

FIGS. 28F-28G, there are illustrated two additional examples of two different patients with substantially the same symptoms and utilizing substantially the same process for preparing the biologic sample. With respect to FIG. 28F, the fifth reservoir and the antibiotic associated there with exhibited the highest efficacy at the highest dose as to destroying the particular bacteria, in the example of the bacteria. The associated dosage determined from testing the biologic sample in the bank 2814 was considered to be the second level of dosage. In the bank 2020, the third level of dosage was considered to be the lowest dose. With respect to FIG. 28G, the first reservoir and the antibiotic associated there with was considered to have the highest efficacy with respect to dealing with the particular bacteria and it was the lowest dose in that case when tested in the bank 2814, as compared to the fourth level dosage in the bank 2820. It can be seen thus that different patients will have different "fingerprints" associated with the testing of the same biologic sample repaired and substantially same way.

Figure 28H:
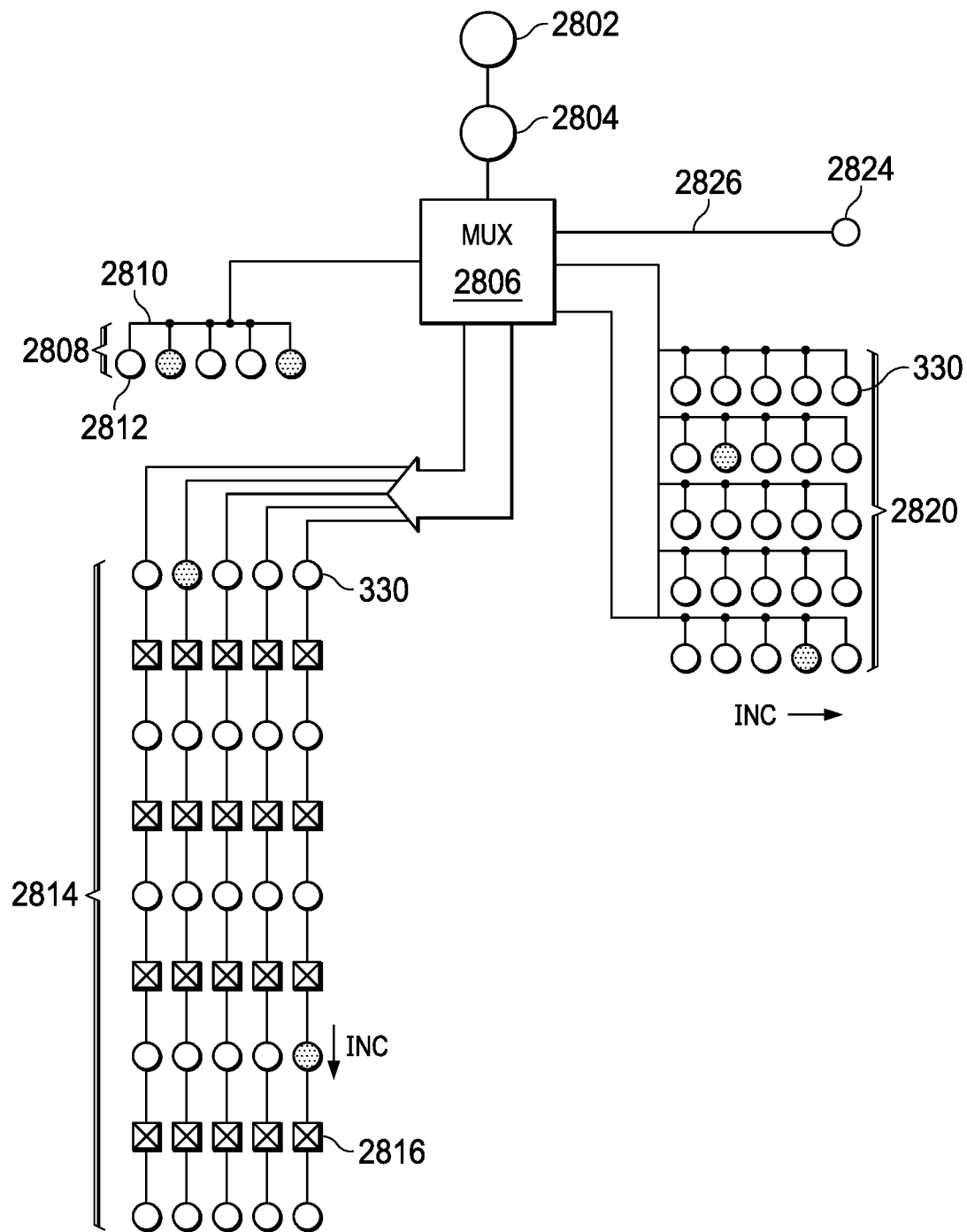

FIG. 28H, there is illustrated an alternate embodiment wherein the test performed at the bank 2808 resulted in a slight ambiguity in that the bacteria were killed in two other reservoirs. In this case, the indication would be that either of these antibiotics would work against this particular strain of bacteria. Thus, the next phase the test would require the multiplexer 2806 to distribute the contents of the reservoir 2804 through the microchannels to actually two different strings. Thus, for this type of test to be carried out, it is important that there be sufficient volume in the viewing window 2804, i.e., sufficient amount of biofluid introduced to the well 2802, in order to fill both of these reservoirs and allow the testing to progress down to the highest dosage level in either or both of the banks 2814 and 2820. The results of this test show that, for the rightmost reservoir in the bank 2808 having been determined to be effective at the highest dose, the next of the last dosage was required in order to achieve the desired results, whereas the next to the left reservoir in the bank 2808 having been determined to be effective at the highest dose required only the smallest dose to achieve the results. Therefore, this test shows that, although two antibiotics would work, one would actually work with the lower dose.

It should also be understood that, in addition to the test being different for the same strain of bacteria in a biologic prepared men substantially the same way, it should also be understood that this particular set of results could be different for different strains of the same bacteria. It may be that, for one strain, one antibiotic would work at a particular dose and, for another strain of the same bacteria, a different antibiotic work or just a different dose of the same antibiotic. The microfluidic chip described and disclosed in the present disclosure allows this determination to be made utilizing a single sample in a parallel/serial testing method at the POC wherein the first step or phase of selection is made among a plurality of potential antibiotics that could arguably target different bacteria and, once a determination is made at the first phase, then the next and serial decision is made to determine dosage at a second phase.

Figure 29:
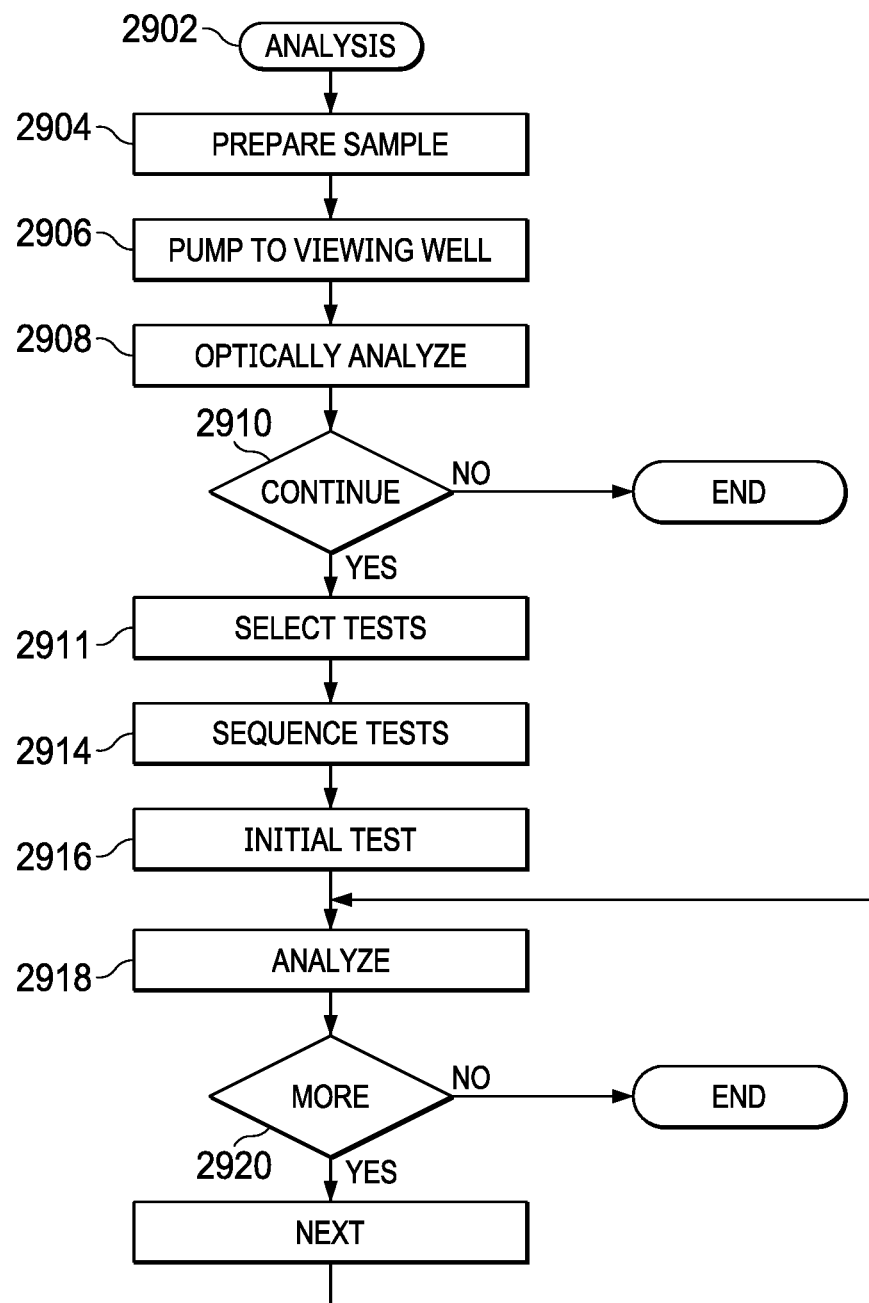
FIG. 29 illustrates a flowchart for the overall analysis process utilizing the microfluidic chip.

Referring now to FIG. 29, there is illustrated a flowchart depicting the overall analysis process. The process is initiated at a block 2902 and then proceeds to a block 2904 wherein the biologic sample is prepared. As described hereinabove, this preparation involves labeling the cells within the biologic sample so that they can be discriminated between or identified. It may be that there are a number of different types of cells such as bacteria of different strains and types, proteins, etc. Different affinity labels can be applied such that multiple cells of different types can be identified. The process then flows to a block 2906 wherein the biologic sample is placed into the sample well and then passed on to the viewing well. At this point, the microfluidic chip is placed into the RT-lamp and optically analyzed, as indicated by process block 2908. It is at this point in the testing phase that the identification process will identify the potential target cells. Since each of the microfluidic chips has a finite number of reservoirs associated there with for the purpose of testing, the coating is applied to these particular reservoirs for the specific antibiotics or reagents to be tested may not be useful for testing the particular cellular structures that have been identified at this step in the process. However, it should be understood that the number of different banks of testing reservoirs that can be provided on a particular microfluidic chip can be expandable and the could actually be provided for multiple different types of reagents. For example, one set of testing banks may be associated with UTI and another associated with streptococcal bacteria.

Recognizing these at this step in utilizing them with a microfluidic chip that can test for both types of bacteria will allow the particular biologic sample, which is quite small, to be routed to the appropriate reservoirs for testing for that specific identify bacteria.

The decision to proceed is determined at a decision block 2910 and, if testing can proceed with the current microfluidic chip, the process proceeds to a block 2911 to select the particular test that are to be performed. The process then proceeds to sequence through the tests, as indicated by a block 2914. This sequencing sequences through the various phases, with the initial test being selected first, as indicated by block 2916. In the above examples, this is the first parallel phase to determine which among several reagents is most effective against the particular cellular structure of interest. The process and proceeds to a block 29 eight teen in order to analyze the results of this initial test and then to a decision block 2920 to determine if more tests are required or if this is the only test. If the test is negative at this stage and none of the reagents provides any effectiveness indication, the process is terminated or, if this is the last test, the process is terminated. The process, if continued, then selects the next test in the sequence and proceeds back to the input of the block 2918 to continue sequencing through the tests.

Figure 30:
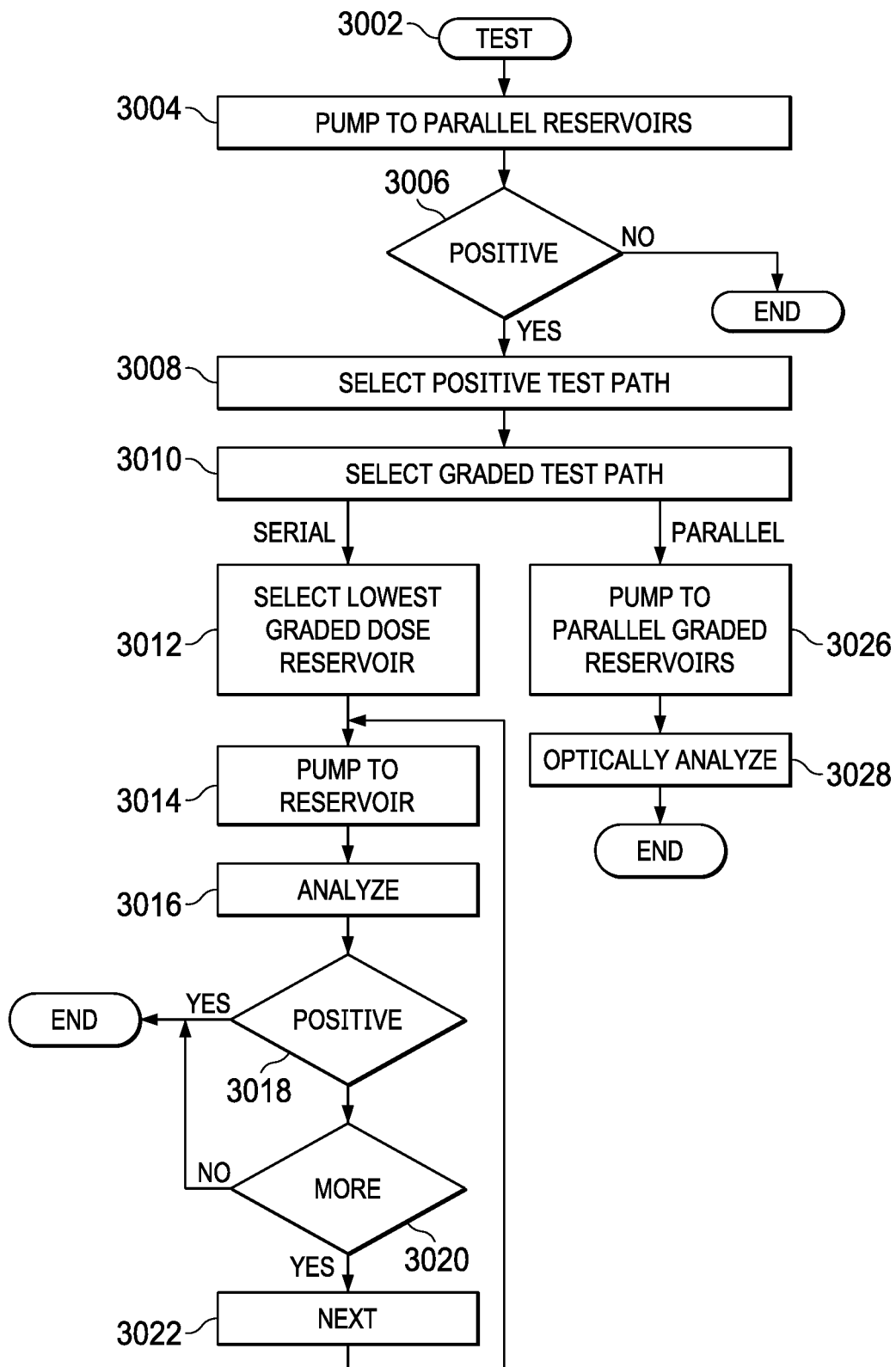
FIG. 30 illustrates a flowchart to pick in the details of the test path.

Referring now to FIG. 30 come there is illustrated a flowchart for the testing process. This is initiated at a block 3002 and then proceeds to a block 3004 two first pump a portion of the biologic sample stored in the viewing window through to the parallel reservoirs and load all of the parallel reservoirs for testing/analysis. This may take upwards of 10 or 20 minutes, due to the fact that the micropumps utilized are relatively slow and the diameter of the microchannels is small, thus restricting high flow rates. The process then flows to decision block 3006 to determine if there is been any positive result, i.e., is there any indication that any of the reagents provide an effectiveness indication, either through some color change or the lack of color indicating the destruction of the cells. If there is no result, then the process is terminated in the process flows to a function block 3008 two select the next test path that is associated with the antibiotic having been tested as being effective in the first phase of operation/testing. A process block 3010 and indicates that a graded dosage test path is selected, either the one for loading parallel or the one or loading serially. It should be understood that the parallel loaded graded dosage test path requires all of the reservoirs to be completely filled from the reservoir associated with the viewing window. The serial path, by comparison, allows all of the contents of the viewing window in the reservoir associated there with to be disposed in each reservoir and then sequentially transferred to the next reservoir down the chain and at the higher dosage. However, it should be understood that the system can be configured such that the first reservoir at the lowest dosage is loaded with only a portion of the contents of the viewing window and the reservoir associated there with, analyzed and then a micro valve gate opened to allow the micropumps for pumping fluid to the serial path to operate to continue pushing more biofluid through the first reservoir, thus filling the second and reservoir and so on. In this process, sufficient biofluid must be contained within the viewing window and the reservoir associated there with in order to allow for filling of all of the reservoirs down to the highest dosage rate associated with that serial string.

In the process, the serial string will first select the lowest graded dose reservoir and a process block 3012 and then pump biofluid to the first reservoir and a process block 3014, analyze the results a process block 3016, understanding that it could take 10 to 20 minutes to fill each reservoir. A determination is made at a decision block 3018 as to whether there is a positive result, i.e., was there and an effectiveness determination made at this point, and, if so proceed to a decision block 3020 to determine if there are any higher concentrations to be tested for. If so, the next reservoir selected by opening gate or activating a micropump, as indicated by a process block 3022, and the proceed back to the process block 3014 in order to pump to this reservoir.

In the parallel process, a process block 3026 indicates an operation wherein the micropump pumps sufficient biofluid material to the parallel rated reservoirs to fill all of the reservoirs and into a process block 3028 in order to analyze the results.

In some embodiments, a biological specimen (i.e. saliva, blood, urine, semen, feces) may be provided by a user onto an analog testing device. The analog testing device may be used for testing strep (i.e. strep A, strep B, rapid strep), TP/INR, chronic conditions, MERS (Middle Eastern Respiratory Syndrome), diabetes, urinary tract infection and analysis, influenza, pregnancy, HIV, malaria, immunology, blood glucose, hemoglobin, blood electrolytes, cholesterol, fertility, troponin, cardiac markers, fecal analysis, sperm viability, food pathogens, HemoCues, CRP (put them in), dengue fever, HBA1C (put them in), Homocystein, salivary assay, drugs of abuse, drug interaction, infectious diseases, viral loads, tuberculosis, allergies (i.e. food and environment), Lyme disease, Methacillian-resistent MRSA, *staphylococcus* areas, sexually transmitted diseases, thyroid stimulating hormone (TSH), lipid profile, INR (put them in), TEG, magnesium, lactate, transcutaneous bilirubin, *Helicobacter pylori*, bacteria, cell count, cancer markers, tumor markers, resistant staph *aureus*, antibiotic resistance, stroke markers, sepias markers, DNA markers, parathyroid, renal, or any other type of analog testing device that utilizes a biological specimen to determine a user's disease, disability, discomfort or dissatisfaction state of health. In some embodiments, the analog testing device may be compact and hand-held. In some embodiments, the analog testing device may be a standard stand-alone device.

In some embodiments, the user may take a sample of the biological specimen and transfer the biological specimen to an input of the testing device. The input of the testing device may include an input window that guides and holds the biological specimen securely within the analog testing device. In some embodiments, more than one window may be provided on the analog testing device to accommodate more than one biological specimen. For instance, the analog testing device may include two windows for a pregnancy test, in which one window may be provided to receive urine to test for the presence of HCG and a second window may be provided to receive urine to test for urinary tract infection bacteria. In some embodiments, multiple analog testing devices with one or more input windows may be used to detect the biological specimen. In some embodiments, the analog testing device may include a results display window indicating a positive or negative sign, a color spectrum, a line, a circle, a curve, a balloon, a signature marker, or variance of the like. The results may be mathematical, geometrical, color spectral, light spectrum, cell multiplication, or the like. The display window may indicate the completion of the test, an error, the test results or a combination thereof.

In some embodiments, the user may capture the results on the results display window via a mobile computing device, for instance in the form of audio, video, photo, scan, or a combination thereof. The mobile computing device may include one or more peripheral devices, for instance, an image scanner, microphone, video recorder, digital camera, speakers, and the like, to capture the results from the analog testing device and convert the results into a digital data package.

Figure 31:
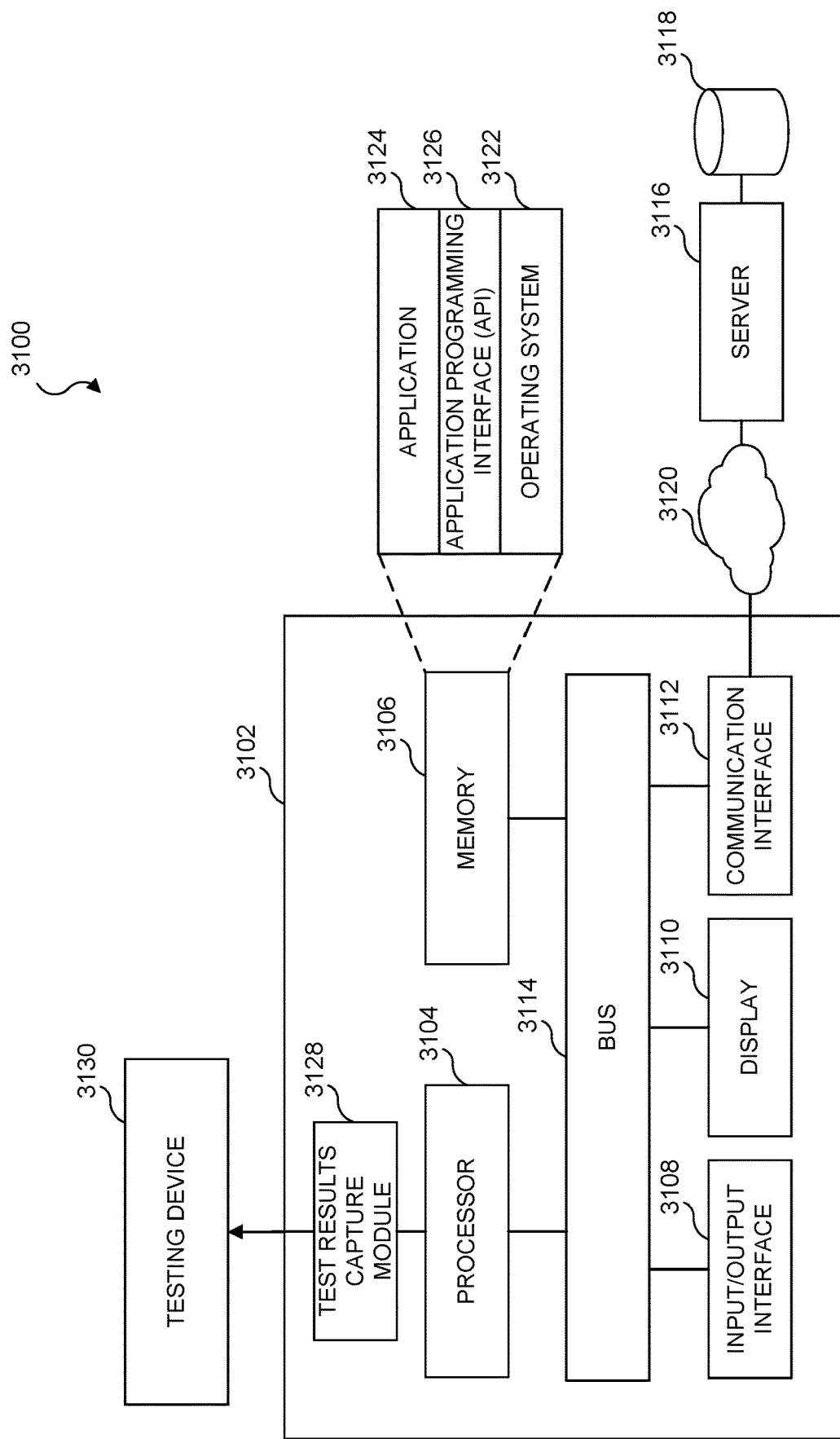
FIG. 31 illustrates a diagrammatic view of a biofluidic triggering system in accordance with various embodiments of the present disclosure.

FIG. 31 illustrates a diagrammatic view of a biofluidic analysis system 3100 in accordance with various embodiments of the present disclosure. The system 3100 may include a mobile device 3102. The mobile device 3102 may be a mobile handheld user device, such as a smart phone, tablet, or the like. The mobile device 3102 may include a processor 3104, a memory 3106, an input/output (I/O) interface 3108, a display 3110, and a communication interface 3112 all connected via a bus 3114. The communication interface may connect the mobile device 3102 to outside sources, such as a server 3116 having a database 3118 associated therewith, over a network 3120, i.e. a cellular network or Internet network. The memory 3106 may store an operating system 3122 and various special-purpose applications, such as a browser by which webpages and advertisements are presented, or special-purpose native applications, such as weather applications, games, social-networking applications, shopping applications, and the like. The digital data package may provide data to a special purpose native application 3124 stored in the memory 3106, the application 3124 having associated therewith an application programming interface (API) 3126. The digital data package may be obtained by the mobile device 3102 by an test results capture module 3128 connected to the processor 3104. The test results capture module 3128 may capture an image, scan, video, or other digital media of a testing device 3130, converting the analog biologic sample testing device and the results presented on the device to a digital format and to create a unique identifier that can be used to trigger a plurality of events.

The unique identifier comprising the digital data package may be analyzed by the application 3124 to determine the results from the analog testing device. In some embodiments, the determination of the test results, due to the type of analog testing device, is not determined locally by the application 3124. In some embodiments, the unique identifier may be transmitted to the server 3116, via the network 3120, for remote analysis of the data contained in the unique identifier. In some cases, results from the analog testing device may be determined locally and remotely. In some instances, the user of the mobile device 3102 may not have cellular network or Internet connection, for instance, the settings for connectivity on the mobile device 3102 is disabled, turned off or a combination thereof. In this case, the transmission of the unique identifier to the server 3116 may be postponed until a connection is available.

In some embodiments, the mobile device 3102 may include a location sensor, such as a global positioning system (GPS) sensor or other components by which geographic location is obtained, for instance, based on the current wireless environment of the mobile device 3102, like SSIDs of nearby wireless base stations, or identifiers of cellular towers in range. In some cases, geographic locations are inferred by, for instance, an IP address through which a given mobile device 3102 communicates via the Internet, which may be a less accurate measure than GPS-determined locations. In other cases, geographic location is determined based on a cell tower to which a mobile device 3102 is wirelessly connected. Depending on how the geographic data is acquired and subsequently processed, that data may have better or less reliable quality and accuracy.

Figure 32:
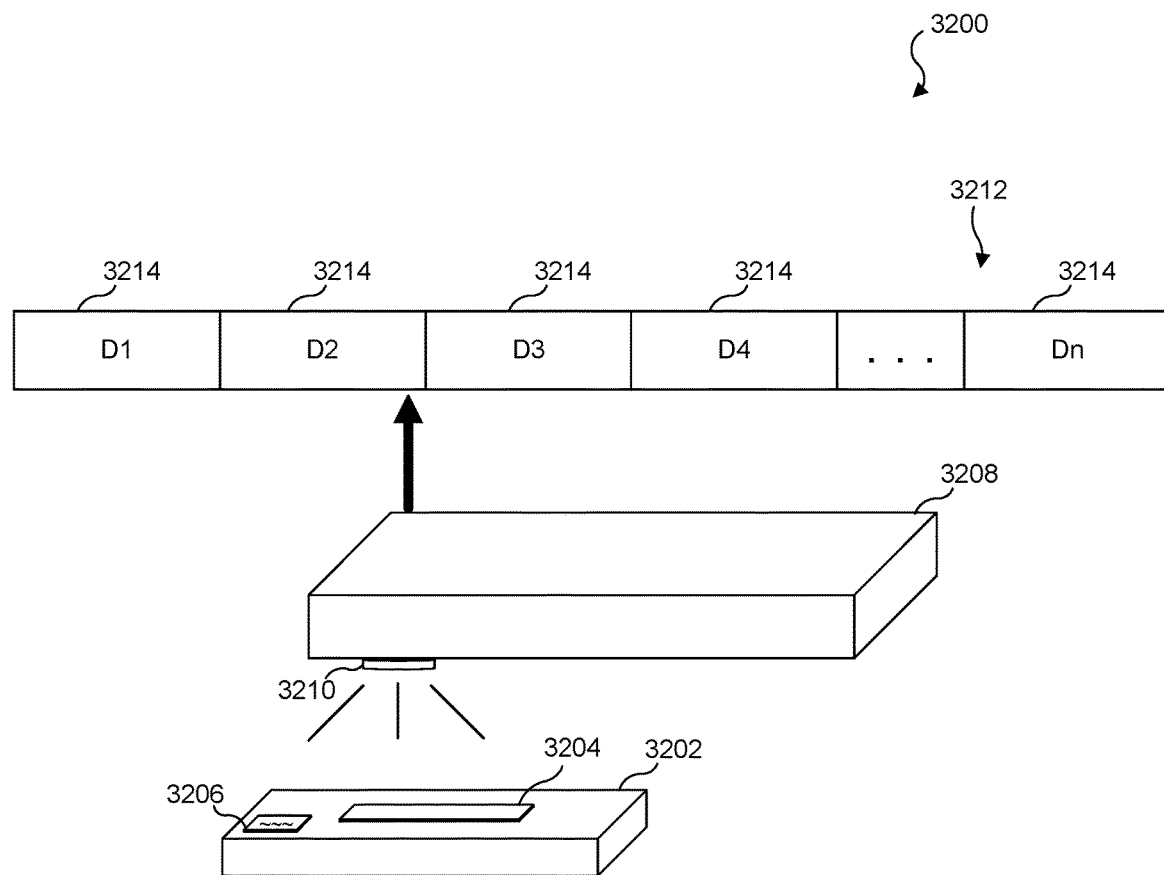
FIG. 32 illustrates a diagrammatic view of an analog testing device to a digital format and unique identifier conversion process.

FIG. 32 illustrates a diagrammatic view of an analog testing device to a digital format and unique identifier conversion process 3200 in accordance with various embodiments of the present disclosure. A testing device 3202 may provide medical test results in an analog format, such as in a results display window 3204 indicating a positive or negative sign, a color spectrum, a line, a circle, a curve, a balloon, a signature marker, or variance of the like. A biologic specimen may be deposited into the testing device 3202 where the biologic may bind or react with particular reagents specific to the type of test to which the testing device 3202 pertains. The testing device 3202 may also include a test type identifier 3206, such as a code, graphic, symbol, or other indicator on a surface of the testing device 3202.

A mobile device 3208, which may be the mobile device 3102 described herein, may include a capture device 3210. The mobile device 3208 may convert use the capture device 3210, in addition to other data known or otherwise obtained by the mobile device 3208, to convert the analog data and biologic presented by the testing device 3202 to a digital unique identifier 212. When digital media such as an image, video, or other digital format of the testing device 3202 is captured by the capture device 3210, certain properties may be analyzed, processed, and stored into as a digital data package. For instance, the test type associated with the testing device 3202 may be determined by the mobile device 3208 by identifying the particular test associated with the test type identifier 3206 captured within the digital media.

Test results provided in the results display window 3204 or elsewhere on the testing device 3202 may also be captured within the digital media and analyzed. For example, in the case of a color indicator as the result of the test, the RGB values of the pixels contained in the digital media of the test results may be determined in order to provide a digital value for the test results. The test result may be stored in the digital data package in a particular digital format, for instance, a positive or negative test result value. The value may be a binary value, a rating, a probability, or other type of result indicator. The biologic specimen used to conduct the test may also be included in the digital data package. The biologic specimen provided into the testing device 3202 may be determined from the test type identifier 3206, since in many cases the specific test will dictate the biologic to be used.

The data provided by the digital data package may also include the type, manufacture and serial number of the testing device 3202, and a timestamp for when the capture device 3210 captured the digital media. The manufacture, serial number and cellular provider of the mobile device 3208 may also be included in the digital data package. The application 3124 may then generate the unique identifier 3212 from the data of the testing device 3202 and mobile device 3208, in combination with data of the user of the mobile device 3208. Data of the user may be the user's name, birthday, age, gender, social security number, height, weight, race, diagnosis status, insurance information, medical codes, drug codes, and the like, and a combination thereof.

In some embodiments, the unique identifier may be verified by a verification server, such as the server 3116, to determine the authentication of the biological specimen. In some cases, the user may provide the analog testing device 3202 with a substance not classified as a biological specimen. In this instance, an application on the server 3116 will provide the application program 3124 with a message indicating an error, in which the user may be required to provide a biological specimen to a different analog testing device. In some embodiments, after verification of a biological specimen, the local application program 124 or the server 3116 via the user's application program 124 will provide the user with a positive or negative outcome of the analog testing device 3202. In some cases, the user is displayed a negative test result and the application program 124 of the mobile device 3208 indicates that testing is completed. In other cases, the user is displayed a positive test result by the application program 124 on the display 3110 of the mobile device 3208.

The unique identifier 3212 may include of a plurality of digital data streams 3214 used during creation of the unique identifier 3212, such as information included within the digital data package, or otherwise known or obtained by the mobile device 3208 or the server 3116. The plurality of digital data streams 3214 (D1, D2, D3, D4 . . . Dn) may be assembled together to create the unique identifier 3212, and the mobile device 3208, the server 3116, or the authorized system components may parse or deconstruct the unique identifier 3212 to analyze specific user properties or test properties, and to trigger events based on the properties.

Creating a single unique identifier 3212 which contains many different items of information is an efficient way of associating many different types of information with a single biologic, user, test, etc. Every time a test is conducted, a new unique identifier 3212 may be created. Each unique identifier created may include the plurality of data streams 3214. Each one of the plurality of data streams 3214 in the unique identifier 3212 stores a different type of information. In some embodiments, the information stored in data streams 3214 includes the test type, the test results, demographics of the user, or an identification number, such as an IMSI number, for the mobile device 3208. Different embodiments may include different data streams 3214, as is described hereinbelow with respect to FIGS. 4A-4K. In some embodiments, the unique identifier 3212 is set up in a structural format, such that each data stream 3214 is a subcomponent of the unique identifier 3212. In some embodiments, unique identifier 3212 is a string of alphanumeric characters, and the data streams 3214 which make up the unique identifier 3212 are simply different portions of the character string. In these embodiments, the format of the unique identifier 3212 is known to a database or server which can correctly parse the unique identifier 3212 into the separate data streams 3214 for analysis.

Figure 33:
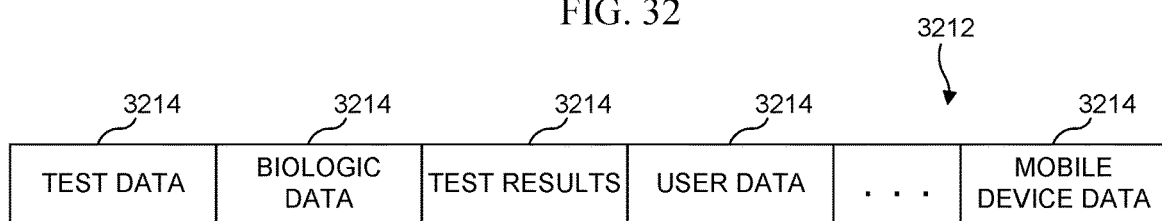
FIG. 33 illustrates one example of a unique identifier in accordance with various embodiments of the present disclosure.

FIG. 33 illustrates one example of a unique identifier 302 in accordance with various embodiments of the present disclosure. In this example, the plurality of data streams 3212 includes, but is not limited to, test data, such as test type, biologic data, such as biologic type or types used by the test, test results obtained upon completion of the test, user data such as demographics, and mobile device data, such as an IMSI number.

Figure 34A:
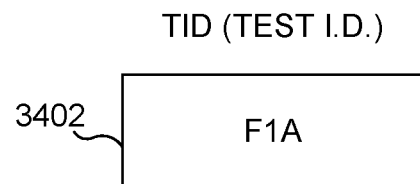
FIG. 34A illustrates an embodiment in which one of the data streams of the unique identifier is a test identification, TID field.

Referring now to FIG. 34A, there is illustrated an embodiment in which one of the data streams 3214 of the unique identifier 3212 is a test identification, TID data stream 3402. The TID data stream 3402 identifies the type of test which the user is conducting (pregnancy, HIV, peanut allergy, etc.). In the example depicted in FIG. 34A, the TID data stream 3402 is a character string of "F1A," which indicates that the test is for the flu, is test version "1," and is a test of an example "A" type of flu substrain. Different embodiments of TID data stream 3402 will have different sizes of character strings, or will not be character strings at all. In some embodiments, this information is obtained when a user uses the mobile application to scans a barcode or image from the test product, or when the user inputs an identification code into the mobile application. In some embodiments, the data in the TID data stream 3402 is used by the mobile application to determine which database to access when processing the results of the medical test.

Figure 34B:
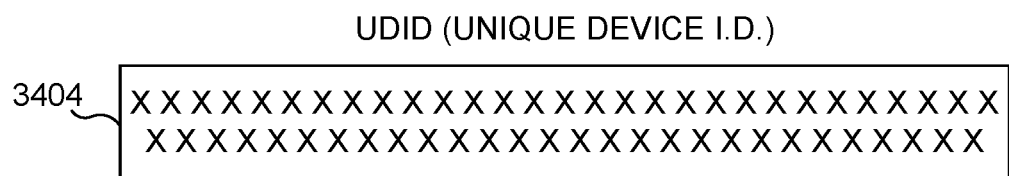
FIG. 34B illustrates an embodiment in which one of the data streams of the unique identifier is a unique device identification, or UDID field.

Referring now to FIG. 34B, there is illustrated an embodiment in which one of the data streams 3214 of the unique identifier 3212 is a unique device identification, or UDID data stream 3404. The UDID data stream 3404 contains information which uniquely identifies the mobile device on which the application is running. Many devices, such as mobile phones, have unique identifiers built-in by the manufacturer, often in the form of long character strings, such as an IMSI number. In some embodiments, the UDID data stream 3404 is a character string which includes such an identifier. In other embodiments, the UDID 3404 is generated by the mobile application or the mobile application user.

Figure 34C:
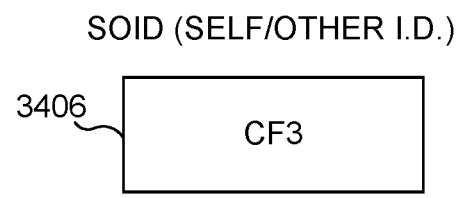
FIG. 34C illustrates an embodiment which includes a SOID (self/other identification) field.

Referring now to FIG. 34C, there is illustrated an embodiment which includes a SOID (self/other identification) data stream 3406. The SOID data stream 3406 is a data stream 3214 which designates whether the medical test is being performed on the mobile application user, or whether the test is being performed on an individual other than the user. The SOID data stream 3406 also identifies the relationship between the person being tested and the mobile application user. Some embodiments also include basic demographic data, such as gender or age range, in the SOID data stream 3406. For example, if the person being tested is a small child, then the actual user of the mobile application may be the child's mother or father. In the example depicted in FIG. 34C, the SIOD data stream 3406 is a character string which reads "CF3," which indicates that the person being tested is a child of the mobile application user, is female, and is three-years-old. Naturally, other embodiments will have different formats for the SOID data stream 3406, and may not be character strings.

Figure 34D:
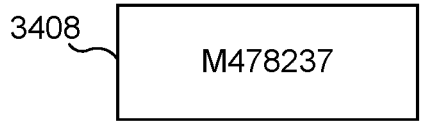
FIG. 34D illustrates an embodiment which includes a data stream which contains demographic information.

Referring now to FIG. 34D, there is illustrated an embodiment which includes a data stream 2302 which contains demographic information. A DEMZIP data stream 3408 (demographic/ZIP code) contains information about the person being tested with the medical test. In the example illustrated in FIG. 34D, the DEMZIP data stream 3408 includes a character string which represents the gender, age range, and geographic location (in the form of a ZIP code) of the person being tested. For example, in FIG. 34D, the DEMZIP data stream 3408 indicates that the test subject is a male, in age range 4, who is located in the ZIP code 78237. In other embodiments, the DEMZIP data stream 3408 will have additional demographic traits included, such as height or weight. Some embodiments will contain geographic location information in a format other than ZIP code, such as city, state, or country names. In some embodiments, such as is illustrated in FIG. 34D, the DEMZIP data stream 3408 will be a character string, while in other embodiments, it will take other forms.

Figure 34E:
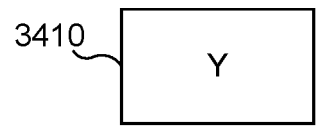
FIG. 34E illustrates an embodiment in which the unique identifier contains a data stream which indicates whether or not the user has supplied their personal email address.

Referring now to FIG. 34E, there is illustrated an embodiment in which the unique identifier 3212 contains a data stream 3214 which indicates whether or not the user has supplied their personal email address. A personal email data stream 3410 does not actually contain the email address of the user, but it does indicate whether or not the user has supplied an email address to the mobile application. In some embodiments, if personal email data stream 3410 indicates that the user has supplied an email address, then when the unique identifier 3212 is passed to a remote server, the remote server will link the unique identifier 3212 with the email address of the user which has been stored in a separate database. In some embodiments, such as illustrated in FIG. 34E, the personal email data stream 3410 is a simple character string of "Y" or "N" to indicate "yes" or "no" with regard to whether an email has been supplied. Other embodiments will have a "1" or a "0" for "yes" or "no" or may have other character strings or data formats.

Figure 34F:
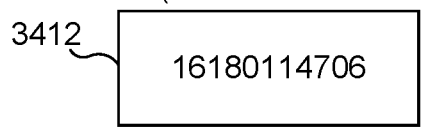
FIG. 34F illustrates an embodiment of a data stream for a unique identifier which contains a timestamp of when a completed medical test is scanned or photographed by the mobile application.

Referring now to FIG. 34F, there is illustrated an embodiment of a data stream 3214 for a unique identifier 3212 which contains a timestamp of when a completed medical test is scanned or photographed by the mobile application. Knowing exactly when a medical test was scanned by a mobile application can be very important in different types of analysis. In this embodiment, the DTS data stream (date/time stamp) 3412 indicates the time in a YYMMD-DHHMMSS format, that is, the first two characters indicate the year, the next two indicate the month, the next two indicate the day, the next two indicate the hour (in a 24-hour day format), the next two indicate the minute, and the last two indicate the second. Naturally, some embodiments will have other formats for the DTS data stream other than a 12-character string, and will have different levels of specificity with regard to the time.

Figure 34G:
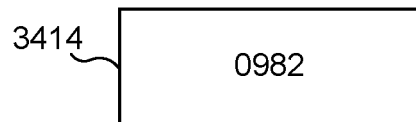
FIG. 34G illustrates a data stream for an embodiment in which a unique identifier contains information related to the results of a medical test.

Referring now to FIG. 34G, there is illustrated a data stream 3214 for an embodiment in which a unique identifier 3212 contains information related to the results of a medical test. These embodiments will have test results, or information related to test results as part of the overall unique identifier 3212 as an EVRK (Evaluation of Results and Ranking of the Diagnosis) data stream 3414, as opposed to, or in addition to, the results being in a totally separate file. In embodiments of the system which use numerical values for test results, these values will be incorporated into the EVRK data stream 3414. Some embodiments will also include an escalation scale, which is a numerical indication, as a number on a predetermined scale, of how urgent or serious a potential medical problem might be. In the example illustrated in FIG. 34G, the EVRK data stream 3414 is a character string and has a value of "0982," with the first three digits representing the results of the test and the last digit representing the escalation scale value. Other embodiments will have other formats for the EVRK data stream 3414 and will have the results indicated in other ways, such as alphanumerically, rather than just numerically.

Figure 34H:
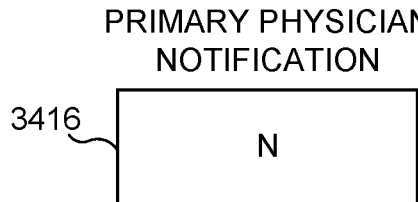
FIG. 34H illustrates a data stream for an embodiment in which a unique identifier includes an indication of whether or not the user wishes to have the test results sent to a healthcare provider.

Referring now to FIG. 34H, there is illustrated a data stream 3214 for an embodiment in which a unique identifier 3212 includes an indication of whether or not the user wishes to have the test results sent to a healthcare provider. In these embodiments, the unique identifier 3212 includes a PDr (personal doctor) data stream 3416. The PDr data stream 3416 is simply an indication of whether or not the user wishes to have the test results transmitted to the user's healthcare provider. In some embodiments, a user inputs this preference into the mobile application after completing the medical test, while in other embodiments, this preference is input into the mobile application separately from any particular test. In some embodiments, an indication of wanting the results sent to the healthcare provider will initiate a telemedicine session with the healthcare provider. In some embodiments, such as that which is illustrated in FIG. 34H, the PDr data stream 3416 is a short, simple character string, such as "Y," "N," "1," or "0." Other embodiments will have different formats.

Figure 34I:
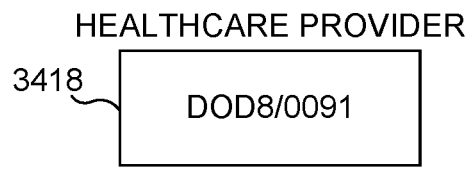
FIG. 34I illustrates a data stream for an embodiment in which a unique identifier includes information identifying the user's healthcare provider.

Referring now to FIG. 34I, there is illustrated a data stream 3214 for an embodiment in which a unique identifier 3212 includes information identifying the user's healthcare provider. In these embodiments, the unique identifier 3212 includes a Healthcare Provider data stream 3418. The Healthcare Provider data stream 3418 includes information which can be used in a storage database to look up the healthcare providers identification and contact information. This information would be used in situations where the mobile application user indicates that they wish to have the medical test results sent to the healthcare provider. In some embodiments, the Healthcare Provider data stream 3418 contains a code which is used to look up more detailed information from another storage database, while in other embodiments, the identification information and the contact email address or phone number is stored in the data stream itself.

Figure 34J:
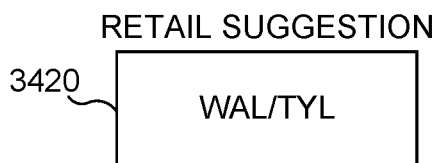
FIG. 34J illustrates a data stream for an embodiment in which a unique identifier includes information relating to a retail suggestion.

Referring now to FIG. 34J, there is illustrated a data stream 3214 for an embodiment in which a unique identifier 3212 includes information relating to a retail suggestion. For these embodiments, a Retail Suggestion data stream 3420 is included in the unique identifier 3212. The Retail Suggestion data stream 3420 includes data which identifies a retailer or a product or service which can be suggested (for example, through the mobile application) to a user. In some embodiments, these suggestions are based on the type of medical test performed. In other embodiments, the suggestions are based on the results of the medical test. For example, if the medical test is a pregnancy test which returns a positive result, then the suggestion might be for a brand of baby diapers. In the example illustrated in FIG. 34J, the Retail Suggestion data stream 3420 provides a suggestion of Tylenol ("TYL") which can be purchased at Walgreens ("WAL"). In the example illustrated in FIG. 34J, the Retail Suggestion data stream 3420 is a character string. In other embodiments, the format of the Retail Suggestion data stream 3420 will be different. In some embodiments, the Retail Suggestion data stream is utilized in situations where the PDr data stream 3416 indicates that the user does not wish to have the test results communicated to a healthcare provider.

Figure 34K:
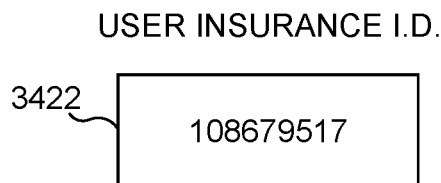
FIG. 34K illustrates a data stream for an embodiment in which a unique identifier includes information identifying the user's insurance I.D.

Referring now to FIG. 34K, there is illustrated a data stream 3214 for an embodiment in which a unique identifier 3212 includes information identifying the user's insurance I.D. In these embodiments, the unique identifier 3212 includes an insurance I.D. data stream 3422. The insurance I.D. data stream 3422 includes information which can be used in a storage database to look up a user's insurance information. This information would be used in situations where the mobile application user indicates that they wish to have the medical test results sent to the healthcare provider, pharmacy, or other entity to allow the user's insurance to be used for a transaction, such as filling a prescription.

Figure 35A:
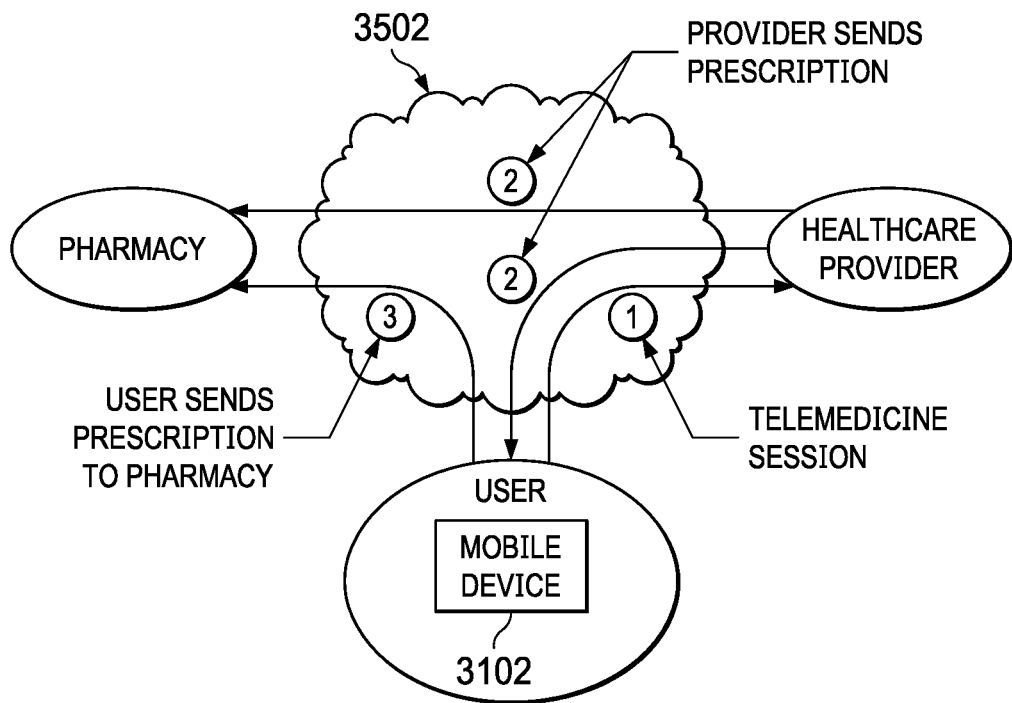
FIGS. 35A and 35B illustrate systems for transmitting prescriptions to a pharmacy using telemedicine.

Referring now to FIG. 35A, there is illustrated an embodiment of a system in which a prescription is transmitted to a pharmacy using a medical test and telemedicine. In these embodiments, rather than the patient needing to physically travel to a pharmacy to drop off a prescription to be filled, the user uses a mobile application to electronically transmit the prescription information to the pharmacy. These embodiments improve upon embodiments which use medical tests and telemedicine and take advantage of the fact that the user is already engaged in a telemedicine session with the user's healthcare provider through a network 3502 such as the internet. In these embodiments, the user engages in a telemedicine session with a healthcare provider as described herein, via Path ①. When the user and the healthcare provider complete the telemedicine session, the healthcare provider can prescribe necessary medicine to the mobile application user. However, since the user is not physically present with the healthcare provider, the user does not pick up a physical prescription slip. Instead, the healthcare provider transmits via Path ②  the prescription in electronic form either to the user's mobile application, or to the pharmacy of the user's choice. If the healthcare provider transmits the "electronic prescription" to the user's mobile application, then the user can then store the electronic prescription on his mobile device 3102 in the mobile application until he is ready to get the prescription filled. The user then uses the mobile application to send the electronic prescription to the pharmacy via Path ③. The pharmacy then fills the prescription as normal.

Figure 35B:
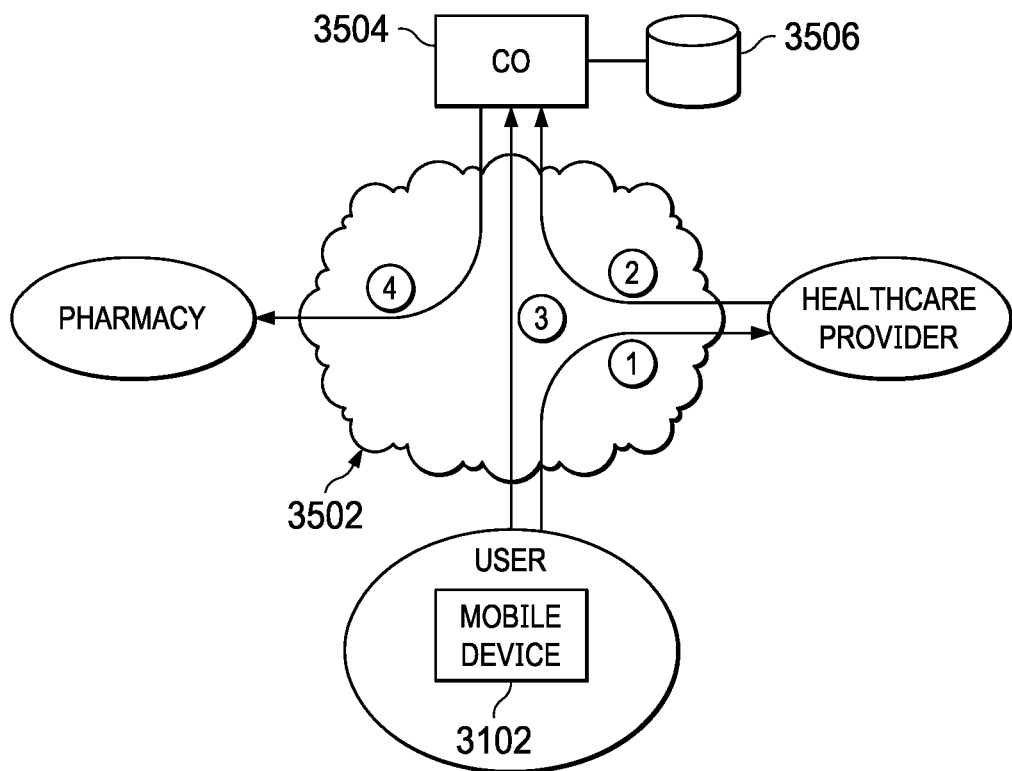

Referring now to FIG. 35B, there is illustrated another embodiment of a system in which a prescription is transmitted to a pharmacy using a medical test and telemedicine. These embodiments are similar to those described herein with respect to FIG. 35A. The system includes a user with a mobile device 3102 running a mobile application, a healthcare provider, a pharmacy, and a remote server or central office with a records database. In these embodiments, the user participates in a telemedicine session with a healthcare provider via Path ① as described herein. Next, if the healthcare provider decides that a prescription is needed, the healthcare provider creates a prescription record and transmits the record through a network 3502 such as the internet to a central office 3504 or remote server via Path ②. The central office 3504 then stores the record in a records database 3506. When the user is ready to have their prescription filled, they use the mobile application on the mobile device 3102 to contact the central office 3504 via Path ③. The central office 3504 then retrieves the prescription record from the database 3506 and sends the prescription record to the pharmacy via Path ④ to have the prescription filled. With this method, the healthcare provider does not have to worry about which pharmacy to send the prescription to, and the fact that the prescription record does not have to be stored on the mobile device 3102 means that the user could potentially access the prescription record from another mobile device or any other compatible device with network access.

Figures 36, 37, 38:
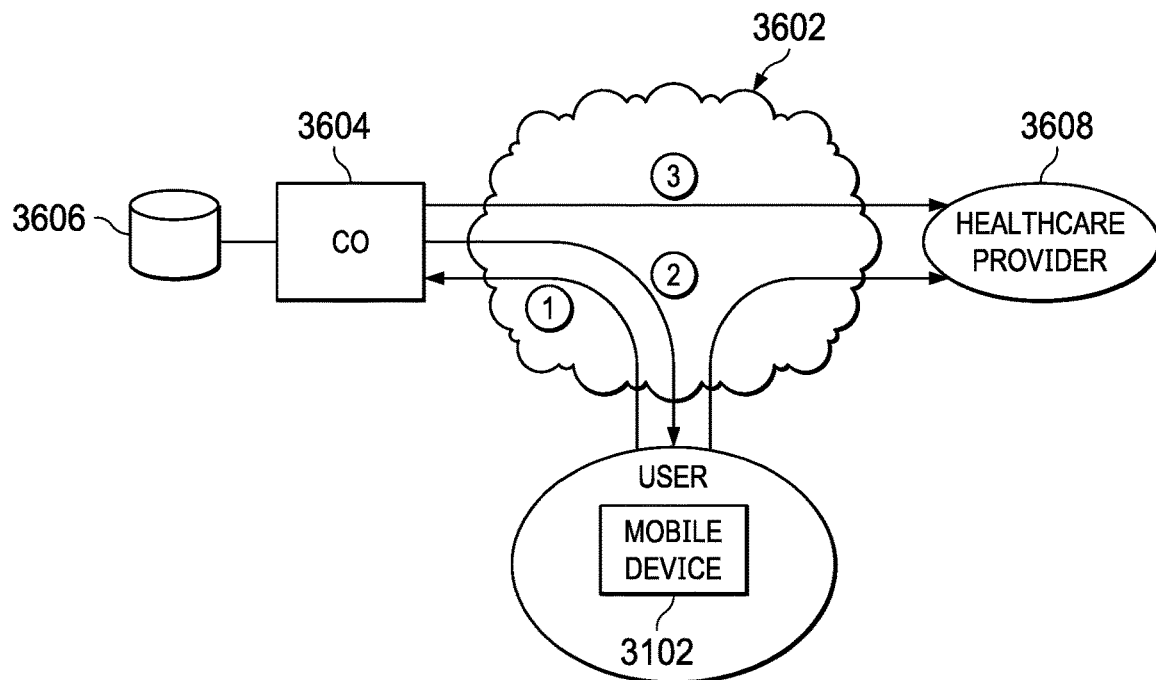
FIG. 36 illustrates an embodiment of a system which utilizes a remote diagnostic test to initiate a medical escalation and intervention.
FIG. 37 illustrates an example of a table which would be found in the database of a central office and which contains criteria for when to initiate a medical intervention based on the results of a remote diagnostic test.
FIG. 38 illustrates an embodiment which includes mapping a diagnostic test to an individual user to create a unique profile on a remote database.

Referring now to FIG. 36, there is illustrated an embodiment of a system which utilizes a remote diagnostic test to initiate a medical escalation and intervention. In some situations, the result of a medical diagnostic test will indicate that immediate or urgent medical attention is needed for the patient. In some embodiments, medical attention will be summoned automatically in these situations. In these embodiments, the user performs a medical medical test and uses a mobile application running on a mobile device 3102 to capture an image of the test product, as described herein. The mobile application then transmits, via Path ①, the test information through a network 3602 to a remote server or central office 3604. The central office 3604 accesses a database 3606 for the necessary information to generate a result for the medical test. The central office 3604 may also retrieve from the database 3606 criteria for determining whether or not a medical escalation or intervention is warranted on the basis of the test results. The central office 3604 generates a test result and checks the criteria to determine if medical escalation is needed. If no medical escalation is needed, the central office 3604 simply returns, via Path ②, the test results to the mobile device 3102 through the network 3602. If, however, the central office 3604 determines that some type of medical escalation is warranted, then the central office transmits, though the network 3602 via Path ③, the test and test result information, along with information about the user (such as any relevant personal, demographic and/or contact information collected from the user) to a healthcare provider 3608. Alternatively, instead of the healthcare provider 3608 being contacted by the central office 3608, in some embodiments, the fact that a medical escalation is needed is transmitted along with the test results from the central office 3602 through the network 3602 via Path to the mobile device 3102 running the mobile application. The mobile device 3102 then transmits the test and test result information to a healthcare provider 3608 through the network 3602 via Path ④.

The manner of the medical escalation or intervention varies depending on the embodiment, and may vary depending on the type of test and/or the test results. In some embodiments, the escalation takes the form of notifying emergency medical personnel, rather than a healthcare provider 3608, of an urgent medical situation. In these embodiments, the central office may call 911 or in some other way notify emergency services These embodiments would be useful, for example, if a blood test shows that the medical test user has near fatal levels blood sugar or that the user is having a heart attack or stroke. In other embodiments, the medical escalation takes the form of the mobile application on the mobile device automatically initiating a telemedicine session with a healthcare provider 3608. These embodiments are useful, for example, in urgent, but not quite emergency, situations. For example, elevated blood sugar or high blood pressure might not be immanently deadly to a patient, but should still be addressed and brought to the attention of a healthcare 3608 provider quickly. In other embodiments which are most useful for urgent—but not quite emergency—situations, the central office 3604 notifies the healthcare provider 3608 of the test results, and leaves it up to the healthcare provider to determine the best next course of action to take with respect to the patient.

Referring now to FIG. 37, there is illustrated an example of a table which would be found in the database of a central office 3606 and which contains criteria for when to initiate a medical intervention based on the results of a remote diagnostic test. The table 3702 includes several columns of information. In the example embodiment depicted in FIG. 37, the diagnostic test is a quantitative one which produces a numerical rating as part of the test result, similar to the embodiments described herein. An example of such a test could be a blood glucose test, wherein a certain risk is generally associated with a range of glucose levels. In this example, a low test result "rating" indicates a low health risk for the condition being tested, while a higher "rating" indicates a higher risk. In the some embodiments which use a table such as table 3702, different types of medical intervention are used for different test results. The first column 3704 of table 3702 specifies a range of test result "ratings," while the rest of the columns 3704, 3706, and 3708 specify information correlating to that rating range. Column 3706 specifies the health risk associated with a particular test result rating from column 3704, and column 3708 specifies what type of medical intervention will be initiated for a test result within a given range. For example, if a user conducts the example medical test, and the central office 3604 generates a test result rating of 57 (which indicates a dangerous health risk), then the central office will not only return the test result to the user, it will also initiate an urgent medical intervention, such as initiating a telemedicine session between the user and a healthcare provider. If the central office 3604 generates a test result rating of 93 (which would indicate a deadly health risk), then the central office will initiate an emergency health intervention, such as notifying emergency medical services of the user's condition. On the other hand, if the test result rating is in the "NORMAL" or "ELEVATED" range, then no medical intervention will be initiated, and the central office 3604 will simply return the test results to the user and the mobile device 3102. Naturally, other embodiments will have different styles of tables in the central office 3604 database. Some embodiments which have qualitative rather than quantitative tests (for example, testing simply "positive" or "negative" for a disease) will not have various multiple different types of medical intervention.

Referring next to FIG. 38, there is illustrated an embodiment which includes mapping a diagnostic test to an individual user to create a unique profile on a remote database. Each time a patient conducts a medical test, there is a change to gather information about that patient and the patient's test. Instead of each piece of information about a patient or a test being regarded individually, multiple data points and pieces of information for a common patient can be associated with each other, providing a greater insight into and creating a detailed profile of the patient. Referring to FIG. 38, there is illustrated a unique profile record 3800. Each unique profile record 3800 is associated with an individual patient or diagnostic test user and has a unique ID 3802. The unique profile record 3800 contains information associated with the patient/user, such as the patient name 3804, the name of a healthcare provider 3806 associated with the patient, or the name of a pharmacy 3808 associated with the patient. Importantly, the unique profile record 3800 also includes the biologic IDs 3810 associated with the user. Each biologic ID 3810 is the same ID as the biologic header 3902 in one of the unique biologic ID database tables 3900. Thus, the unique profile record 3800 includes a "link" to the record of each biologic used by the patient associated with the unique profile record. Each time a diagnostic test is conducted on a biologic sample, the biologic sample is associated with the unique profile record 3800, which means the unique biologic ID database table 3900 (which includes data about the test) is associated with the unique profile record 3800 and the user. This means that more information about the patient is collected and accumulated.

Different embodiments will include different types of data to be stored within each unique profile record 3800. In some embodiments, the unique profile record 3800 includes information about food or medications to which the patient is allergic. Some embodiments of the unique profile record 3800 include records of which illnesses which the patient has had. Virtually any type of information related to the patient/user can be included in the unique profile record 3800 in various embodiments, so long as it contributes to construction a better "picture" of the patient/user.

Referring now to FIG. 39, there is illustrated an example of a unique biologic ID database table 3900. The table 3900 is illustrative of the type of data stored in association with data for a biologic transmitted by a mobile device 3102 for storage on the database 3118. A biologic ID header 3902 is provided that shows that the biologic sample has been given a unique ID. All data concerning the biologic may be stored in association with the unique biologic ID. The table 3900 also includes a biologic type entry 3904. This designates what type of biologic that the biologic associated with the unique ID is, such as blood, urine, stool, saliva, sweat, or other biologics. The table 3900 also provides a plurality of test ratings 3906, for various tests performed on the biologic. In the example shown in FIG. 39, a blood biologic is provided having an assigned ID of 2402, and having been testing for pregnancy markers, the Zika virus, and for glucose levels. The rating for pregnancy was a 99 rating, the rating for a Zika infection was a 75, and the rating for glucose levels was a 10. This would indicate that the test subject has an extremely high likelihood of both a pregnancy and a Zika infection, which would have resulted in a warning to seek medical attention at the conclusion of the tests. Other information may also be stored in the database in relation to the biologic, including other condition ratings, time and date each test was performed, user information such as ethnicity, gender, and age, and status indicators such as whether a test subject visited a physician as a result of the tests. The database 3118 thus provides the test subject with a growing collection of information that may be accessed by the test subject. This allows the test subject to present the test results to her physician for medical attention or additional testing, and allows for others who may access the database, such as disease researchers, to have access to data on various biologic samples and their markers.

Figure 40:
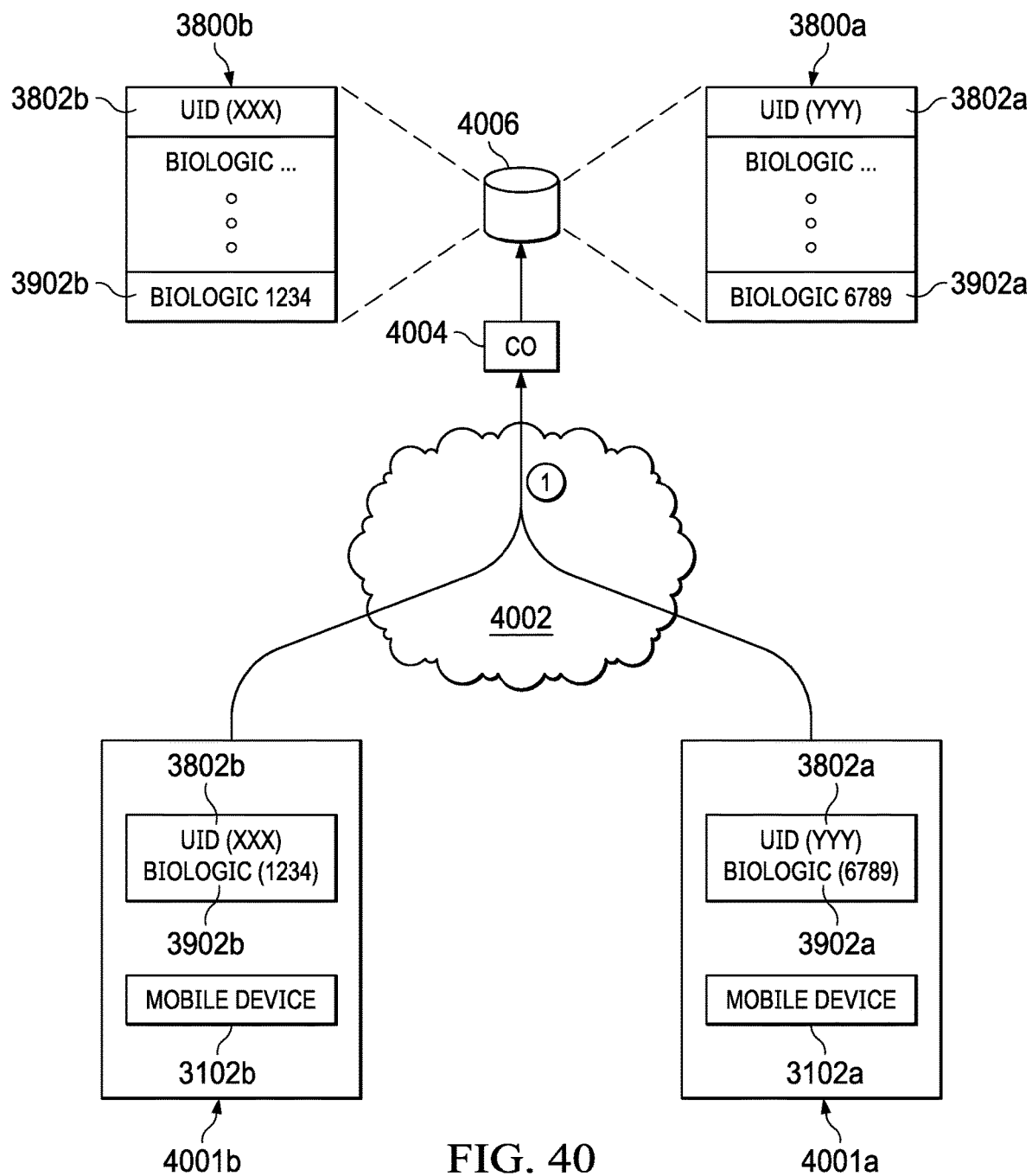
FIG. 40 illustrates an embodiment which includes mapping diagnostic tests to individual users to create unique profiles.

Referring next to FIG. 40, there is illustrated an embodiment which includes mapping diagnostic tests to individual users to create unique profiles. The patient/user 4001 conducts a medical test using a mobile device 3102. The first time the patient 4001 uses the mobile application on the mobile device 3102, the application allows the patient to create a unique ID 3802 to be assigned to the unique profile record 3800 associated with the patient. In some embodiments, the unique ID 3802 is simply assigned by the mobile application instead of being chosen by the user 4001. After a test is conducted, the mobile application transmits the biologic ID 3902 of the biologic tested along with the unique ID 3802 along Path CI through a network 4002, such as the internet, to a remote server or central office 4004. Once the biologic ID 3902 and the associated unique ID 3802 reaches the central office server 4004, the central office server transmits the biologic ID and the unique ID to a connected database 4006. Within database 4006 are stored the unique profile records 3800 for each patient/user 4001. Once the database 4006 receives the biologic ID 3902 and the unique ID 3802, the database uses the unique ID to identify the correct unique profile record 3800 and then appends the biologic ID 3902 to that unique profile record. If this is the first test conducted for/by a particular patient/user 4001, then the database 4006 creates a new unique profile record 3800 with the provided unique ID 3802 and appends the biologic ID 3902. In this way, each time a user 4001 conducts a diagnostic test, the unique ID 3802 and the biologic ID 3902 are sent to the database 4006, where the unique profile record is incrementally augmented with additional information about the user/patient 4001. In some embodiments, the biologic ID 3902 is not assigned by the application on the mobile device 3102. Instead, the mobile device sends the information relating to the biologic (test type, test results, etc.) to the central office serve 4004 and database 4006, which then assign a biologic ID 3902 to the biologic data and associate it with the appropriate unique ID 3802.

Data for other users 4001 with other unique profiles 3802 will be handled similarly. Since each user 4001 has a unique profile record 3800 associated with him or her, the database 4006 will be able to associated biologic IDs 3902 with the correct user. In this way, the database 4006 will be populated with unique profile records 3800, from which potentially vast amounts of data can be obtained.

Figure 41:
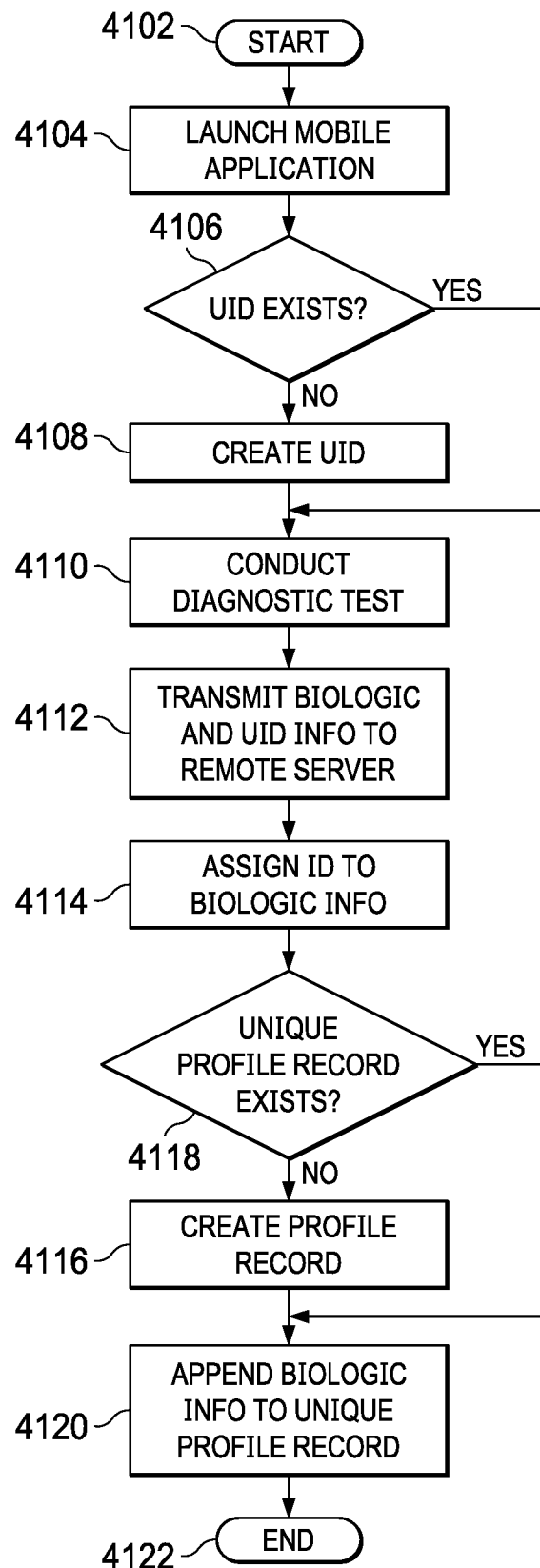
FIG. 41 illustrates a flowchart for an embodiment which includes mapping a diagnostic test to an individual user to create a unique profile on a remote database.

Referring now to FIG. 41, there is illustrated a flowchart for an embodiment which includes mapping a diagnostic test to an individual user to create a unique profile on a remote database. The process starts at Start block 4102 and proceeds to function block 4104, where the user launches the mobile application on the mobile device 3102. The process then moves to decision block 4106. If a unique ID 3802 for the user does not exist, the process moves to function block 4108, where a unique ID is created by the mobile application. The process then moves to function block 4110. If, at block 4106, a unique ID 3802 for the user does exist, the process skips block 4108 and moves to function block 4110. At block 4110, the user conducts a diagnostic test with a testing device 3130 and a mobile device 3102 as described herein. The process then moves to block 4112, where the mobile application transmits the biologic ID information 3902 (which will also link the user to data about the type of diagnostic test) and the unique ID 3802 to the remote server 4004. At step 4114, an ID is assigned to the biologic information. The process then moves to decision block 4118. If a unique profile record 3800 for the user does not exist, the process moves to function block 4116, where a unique profile record is created. The process then moves to function block 4120. If, at decision block 4118, a unique profile record 3800 for the user already exists, the process moves to block 4120. At block 4120, the database 4006 appends the biologic ID information 3902 to the unique profile record 3800. The diagnostic test performed by the user is now mapped to the user's profile 3800 through the biologic database ID table 3900. The process then ends at End block 4122.

In some embodiments, a medical test may be performed by a doctor, lab technician, etc. and may use an automated testing device to perform the test. In this scenario, the test may be used to determine a treatment regimen for a patient based on the test results. For instance, if the test is designed to determine the proper medication and dosage level of that medication to effectively treat a patient, this information may be added to a patient file and transmitted to other parties to alert the other parties to take action in order to enact the treatment plan.

Figure 42:
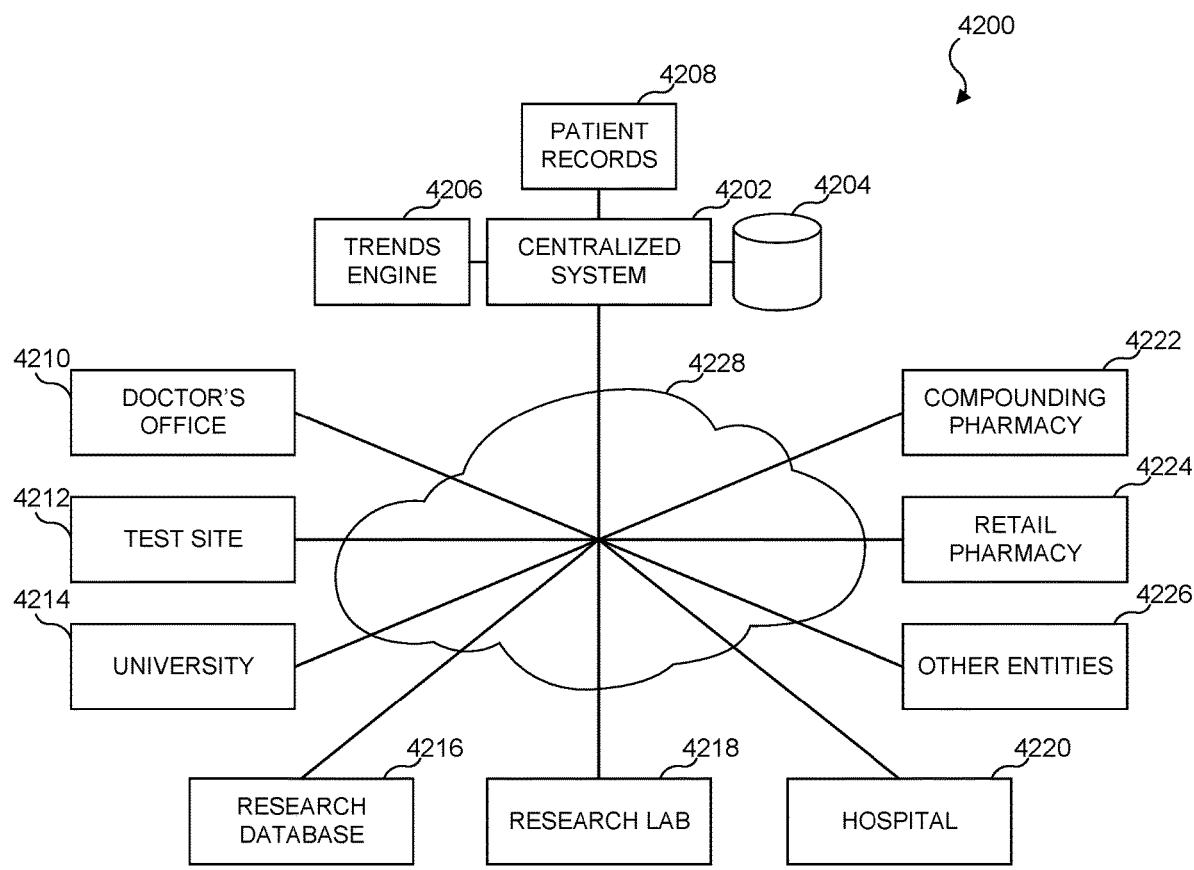
FIG. 42 illustrates a diagrammatic view of a medical test results, trends, and response system.

FIG. 42 illustrates a diagrammatic view of a medical test results, trends, and response system 4200. The system 4200 includes a centralized system 4202. The centralized system 4202 may include or be connected to an actionable analytics database 4204, a trends engine 4206, and a plurality of patient records 4208. The plurality of patient records 4208 may include patient demographics and personal information, medical history including test results, doctor's notes, etc., medical information specific to the patient such as DNA data, blood type, markers detected during tests on the patient, or other types of information. The centralized system 4202 may act as a central hub of information for various entities related to the medical industry. These various entities may be interconnected with each other as well as with the centralized system 4202.

For example, the system 4200 illustrated in FIG. 42 further includes one or more of the following: a doctor's office 4210, a test site 4212, a university of higher learning 4214, a research database 4216, a research lab 4218, a hospital 4220, a compounding pharmacy 4222, a retail pharmacy 4224, the centralized system 4202, and other entities 4226. All these entities may be interconnected over a network 4228 to share information and otherwise provide an infrastructure for tracking medical test results, disease trends, pharmaceutical effectiveness trends, triggering medical actions for patients, etc. For example, test results generated by using the microfluidic chip described herein may include drug efficacy and proper dosage information pertaining to a patient. This information may be passed from the entity in the system 4200 that performed the test, such as a doctor's office 4210, a hospital 4220, a research lab 4218, or any other test site 4212 or other entity 4226. The results may then be received by the centralized system 4202 to update a patient record 4208 stored in associated with the centralized system 4202. The test results, test information, patient information, and other data may be stored in the database 4204 or processed by the trends engine 4206 to evaluate overall patient health, and to determine whether the patient is susceptible to other medical conditions or whether the test results received regarding the patient are indicative of trends or other medical conditions concerning other patients whose information is stored in the centralized system 4202. The results may also be utilized in advancing medical research, such as by universities 4214, research labs 4218, and by updating research databases 4216.

Referring now to FIG. 43, and still to FIG. 42, patient records on file with any of the entities 4210-4226 may also be updated to reflect the new information obtained as a result of the test. FIG. 43 illustrates the types of information that may be recorded in a patient record 4208, or in the database 4204, in accordance with various embodiments of the present disclosure. FIG. 43 shows that a patient may have a patient record 4302. This patient record may be stored as a document on the centralized system 4202, such as a text file, PDF file, excel file, or other document, or the data in the patient record 4302 may be stored in the database 4204. Particular test types may have ID numbers associated with the particular test types. The ID for the test type may be stored in relation to a patient record when the test associated with the test ID is performed on the patient associated with the patient record. Results of the test performed on the patient or on a patient's biologic specimen may also be stored in relation to the patient.

For example, FIG. 43 shows that test results 4304 of a test having a test ID of 10 are stored in relation to a patient having a patient ID of 1002. Test information results, treatment plans, and other information may be stored in relation to the patient. For example, and as illustrated in FIG. 43, if a patient is found to be positive for a bacterial infection, such as streptococcal bacteria, and results from a test conducted using the microfluidic chip described herein indicate that the most effective medication and dosage to treat the infection is amoxicillin at 250 mg, this information may be transmitted across the system 4200. The centralized system 4202 may receive the test results and generate a treatment plan or regimen that indicates that the patient should take amoxicillin at 250 mg twice daily for two weeks. The treatment regimen may be generated for the patient and this treatment regimen may be transmitted to entities responsible for enacting the treatment regimen, such as the doctor's office 4210, the compounding pharmacy 4222 or the retail pharmacy 4224, etc.

Figure 44:
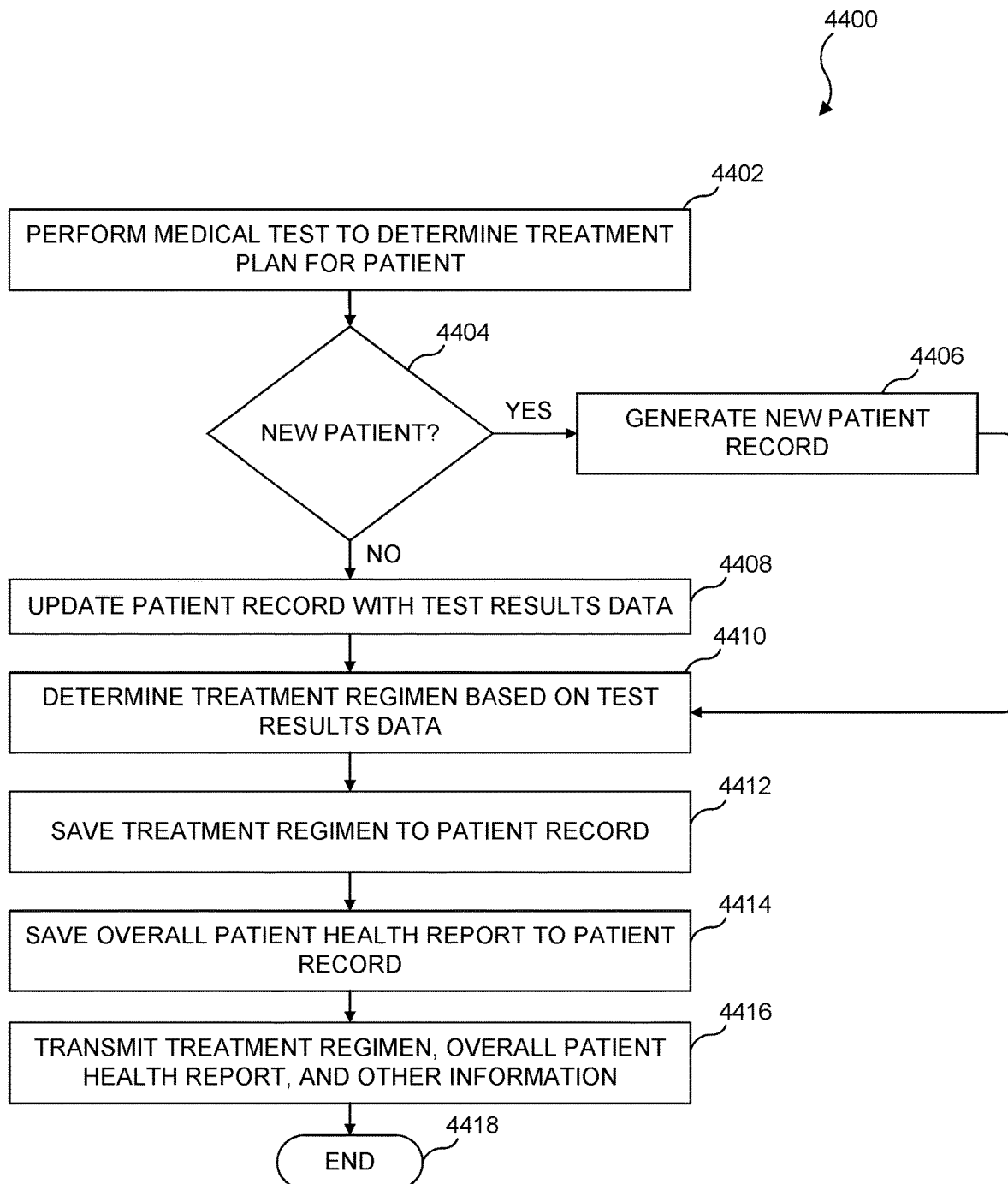
FIG. 44 illustrates a flowchart of a patient record update/creation process.

Referring now to FIG. 44, there is illustrated a flowchart of a patient record update/creation process 4400. The process begins at step 4402 when a medical test is performed to determine a treatment plan for a patient, such as a test using the microfluidic chip described herein. At decision block 4404, an entity such as the centralized system 4202 determines whether the patient is a new patient, which may be done by querying the database 4204 for personal information relating to the patient to determine if that information already exists in the database such as a social security number. If it is determined that the patient is a new patient, the process flows to step 4406 to generate a new record for the patient. The process then flows to step 4410. If at decision block 4404 it is determined that the patient already has a patient record stored, the process flows to step 4408 where the existing patient record is updated with the results of the test performed in step 4402. The process then flows to step 4410. At step 4410, a treatment regimen is determined for the patient based on the test results data. For instance, if a particular medication at a particular dosage level was tested as effective against a medical condition of the patient, a regimen of administration of the medication may be generated.

The process then flows to step 4412 to save the treatment regimen to the patient record. At step 4414, an overall patient health report may be saved to the patient record. This health report may include general information relating to the patient from other office visits, such as weight, medical states such as diabetes or other states, and may include the medical condition with respect to the test conducted in step 4402, such as stating the test date, severity of the condition, details regarding the treatment regimen and drug interactions and side effects, etc. The process then flows to step 4416. At step 4416, the treatment regimen, overall health report, and other patient information may be transmitted to entities that may use such information to treat the patient, such as a doctor's office, hospital, or other entity.

Figure 45:
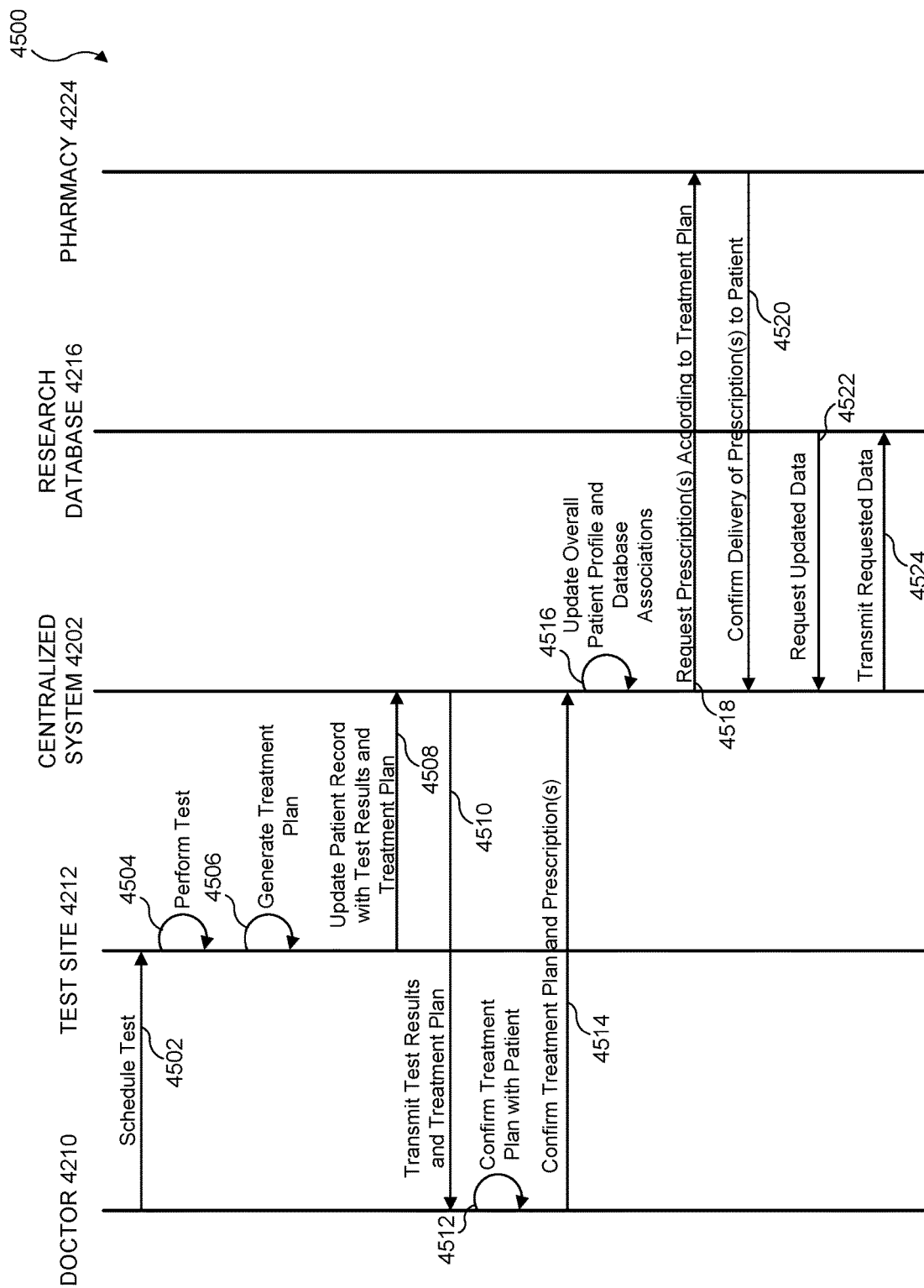
FIG. 45 illustrates a sequence diagram of a test results and treatment regimen enactment process.

Referring now to FIG. 45, there is illustrated a sequence diagram of a test results and treatment regimen enactment process 4500. At step 4502, a doctor sends a request to a test site to schedule a test. The test site at step 4504 then performs the scheduled test. At step 4506, a treatment plan is generated at the test site. The test site may generate the treatment plan when generation of the treatment plan is automated by the device performing the test, or by a professional analyzing the test. In some embodiments, the test results may be sent elsewhere for determining the treatment plan, such as to the doctor or to the centralized system.

At step 4508, the test site sends an update to the patient record at the centralized system with test results and a treatment plan. At step 4510, the centralized system transmits the test results and treatment plan to the doctor's office. At step 4512, the doctor's office confirms the treatment plan with the patient and at step 4514 the doctor's office sends a confirmation of the treatment plan and any written prescriptions to the centralized system. At step 4516, the centralized system updates the overall patient profile and database associations to that patient profile. For example, if the patient is a Caucasian female, and the test results were positive for Crohn's disease, such an association may be made in the database as a potential trend or susceptibility, but may wait for additional data before marking it as an active trend.

At step 4518, the centralized system requests one or more prescriptions from a pharmacy according to the treatment plan. At step 4520, the pharmacy transmits a confirmation to the centralized system that the prescriptions were delivered to or pickup by the patient. At step 4522, a research database may request updated data from the centralized system. The research database may utilize the centralized system as a storehouse for a multitude of information and data points related to diseases, patient demographics, biological markers, or other information useful to medical research and academia. At step 4524, the centralized system transmits the requested data to the research database.

Figure 46:
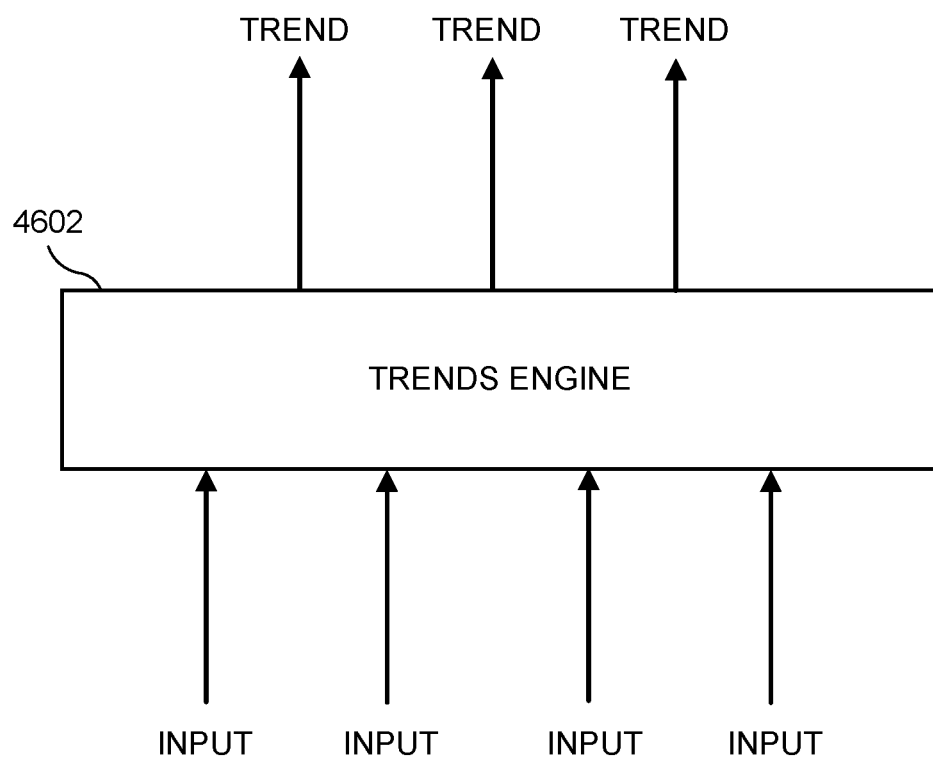
FIG. 46 illustrates a diagrammatic view of a trends engine in accordance with various embodiments of the present disclosure.

Referring now to FIG. 46, there is illustrated a diagrammatic view of a trends engine 4602 in accordance with various embodiments of the present disclosure. The trends engine 4602 may be a linear or non-linear deep learning neural network or trained database. Neural networks are non-parametric methods used for machine learning such as pattern recognition and optimization. They are able to generate an output based on a weighted sum of inputs, which is then passed through an activation function. Typically, the activation function determines the output by summing the inputs multiplied by the weights. A basic activation function is that of $y=f(\Sigma wx)$, where x is the vector of inputs, w is the vector of weights, f(.) is the activation function, and y is the output vector.

The inputs, weights, and outputs may be organized within a multilayer perceptron (MLP), wherein there is an input layer, one or more hidden layers, and an output layer. As shown in FIG. 46, a plurality of inputs may be entered into the trends engine 4602. The trends engine 4602 may include a series of weighted neurons that pass the inouts through an activation function t generate one or more outputs, or trends. The trends engine 4602 may be a feedforward network network. Although there could be any number of hidden layers, typically ranging from one to three, it will be appreciated by those skilled in the art that a single hidden layer can estimate differentiable functions, provided there are enough hidden units. A higher number of hidden layers also increases processing time and the amount of adjustments needed during neural network training.

It will be understood by those skilled in the art that the neural network would be trained in order for the neural network to become more accurate. Various training methods exist, such as supervised learning where random weights are fed into the neural network and adjusted accordingly, back-propagation methods, or other methods. Activation functions are applied to the weighted sum of the inputs to generate a certain outcome. The weights may be set to small random values initially. The input pattern may then be applied and propagated through the network until a certain output is generated for the hidden layer. Training results may be collected including the number of true positives, true negatives, false positives, and false negatives. If the number or percentage of false positives and negatives appear too high, additional training may be required.

The outputs of the hidden layer are used as entries for the output layer. Weighted and summed up, they are passed through an activation function to produce the final output. The way the weights are modified to meet the desired results defines the training algorithm and is essentially an optimization problem. When the activation functions are differentiable, the error back-propagation algorithm may be a good approach in progressing towards the minimum of the error function. The errors are then passed back through the network using the gradient, by calculating the contribution of each hidden node and deriving the adjustments needed to generate an output that is closer to the target value. It will be understood by those skilled in the art that neural networks can be set up and trained in various ways and that the above description is illustrative of but one method. It will be appreciated that the neural network may be organized in any way to allow for the functionality disclosed herein.

In some embodiments, the trends engine 4602 may function on a threshold system. For instance, if a certain number or percentage of patients that are within a specific haplogroup also test positive for a specific medical condition, this may indicate a trend output by the trends engine 4602. As more positive results are received for a particular medical condition, the trends engine 4602 may query the database 4206 to determine if there are any demographical or other commonalities between patients that have tested positive for the medical condition. For example, if the threshold is set to 75%, and 80% of patients of African descent have tested positive for a medical condition, the trend engine 4602 may communicate the trend to other entities within the system

4200, or provide the trend when the centralized system 4202 is accessed by other entities in the system 4200.

Referring now to FIG. 47, there is illustrated one embodiment of database tables showing a particular trend. There is shown a patient record 4702. The patient record 4702 includes various data concerning the patient, such as the test IDs for tests performed on the patient or a specimen from the patient. If a patient has a DNA test performed, a patient's haplogroup may be determined. Haplogroups may be Y-chromosomal or may be mitochondrial haplogroups. The centralized system 4202 may keep track of a patients' haplogroups to attempt to find trends among patients that share a common ancestry. For example, FIG. 47 illustrates that patient ID #1002, in record 4702, is within haplogroup C. Thus, the centralized system 4202 may link the patient to data accumulated and test results obtained regarding all patients that are within haplogroup C. Table 4704 illustrates that the centralized system 4202 may count the number of positive results for each test performed on a person of haplogroup C. In this example, patient ID #1002 has may have tested positive for test ID 10. The table 4704 shows that a large number of people in haplogroup C have also tested positive for test ID #10. There is also shown in patient record 4702 that the patient is susceptible to prostate cancer. This may be determined from a trend similar to that shown in 4704. For instance, if test ID #10 tested for prostate cancer markers, and the 10,720 positive results illustrated in FIG. 47 was above a threshold amount to activate a trend, all patients in haplogroup C, such as patient ID #1002, would have an entry added to his or her patient record noting a trending susceptibility to prostate cancer.

Figure 48:
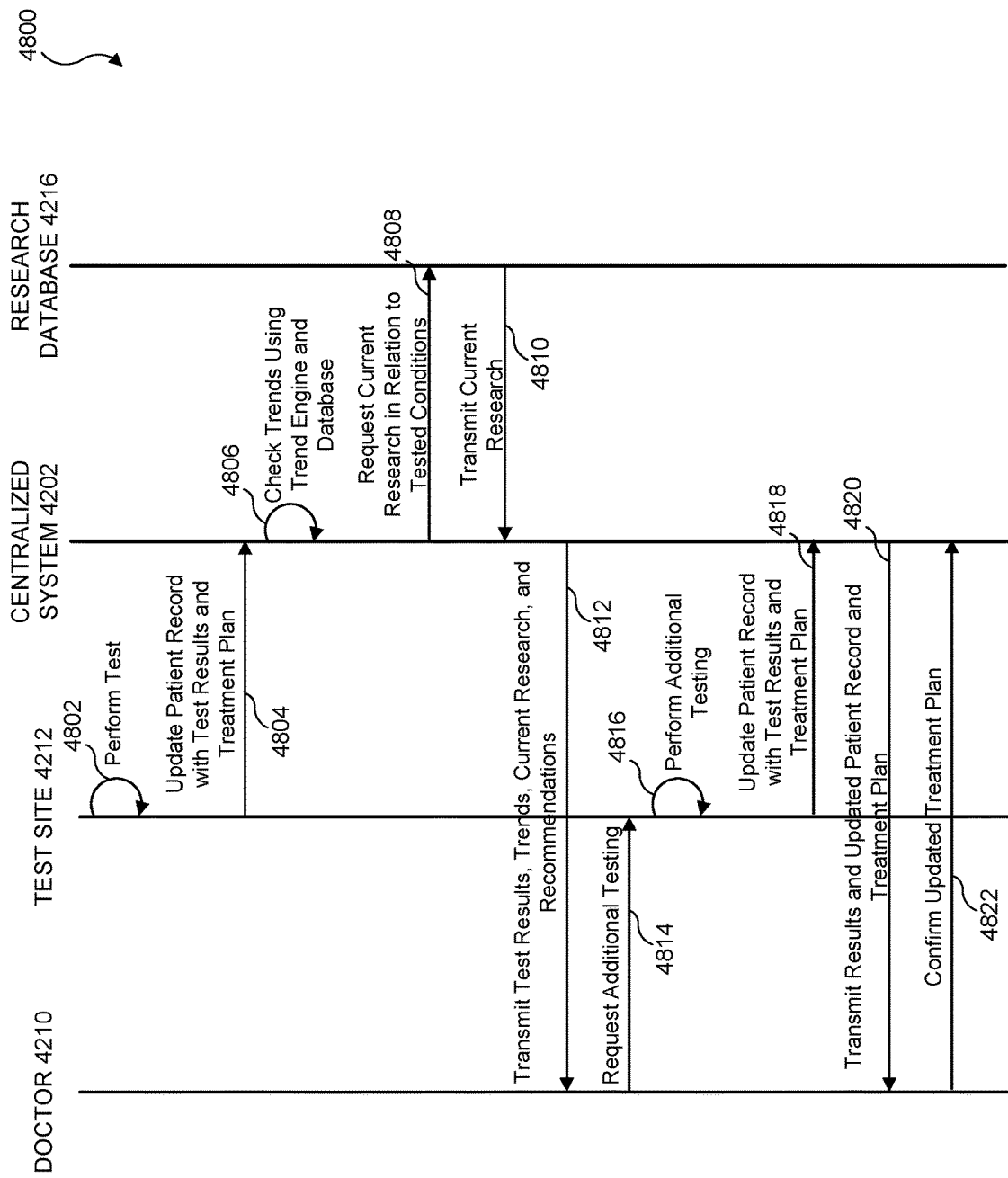
FIG. 48 illustrates a sequence diagram of a research and trends feedback process.

Referring now to FIG. 48, there is illustrated a sequence diagram of a research and trends feedback process 4800. At step 4802, a test site 4212 performs a medical test, such as a test using the microfluidic chip disclosed herein. At step 4804, the test site 4212 sends to the centralized system 4202 a patient record update including test results and a treatment plan. At step 4806, the centralized system 4202 checks trends via the trend engine 4206 and database 4204. At step 4808, the centralized system 4806 requests current research regarding the medical condition of the patient from a research database 4216. At step 4810, the requested research is transmitted from the research database 4216 to the centralized system 4202. At step 4812, the centralized system 4202 transmits the test results, any trends regarding the patient or others similar to the patient, the requested current research, and any recommendations based on this data to the doctor's office 4210. At step 4814, the doctor's office 4210 requests additional testing for the patient. The doctor may request additional testing because of trends regarding the patient's condition or research that was provided to the doctor in step 4812. At step 4816, the test site performs the additional testing.

At step 4818, the test site sends an update to the patient record including the test results for the additional testing and a new or updated treatment plan for the patient based on the additional testing. At step 4820, the test results are update patient record and treatment plan are transmitted from the centralized system 4202 to the doctor's office 4210. At step 4822, the doctor's office 4210 sends confirmation of the updated treatment plan to the centralized office 4822.

Figure 49:
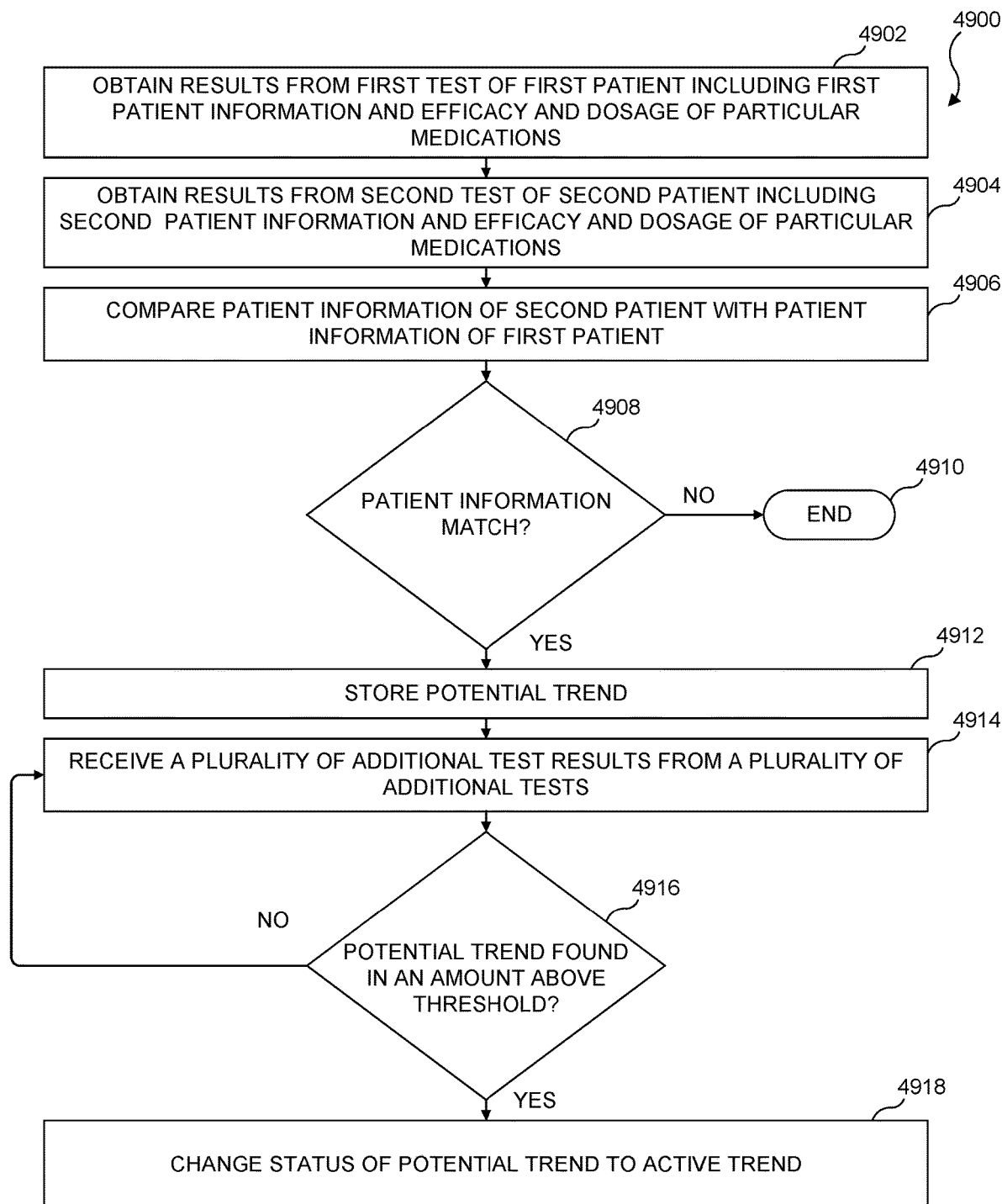
FIG. 49 illustrates a medical condition trend activation process.

Referring now to FIG. 49, there is illustrated a medical condition trend activation process 4900. The process 4900 begins at step 4902, where patient information and the efficacy and dosage for particular medications pertaining to a first patient produced by a first test are obtained by an entity such as the centralized server. At step 4904, patient information and the efficacy and dosage for particular medications pertaining to a second patient produced by a second test are obtained by an entity such as the centralized server. At step 4906, the server compares patient information of the second patient with the patient information of the first patient. At decision block 4908, it is determined whether there is any significant patient information matches. For example, if the tests conducted on both patients were for Crohn's disease, and both patients are of the same gender and ethnicity, then there may be a significant patient information match. If there is no significant patient information match the process flows to end block 4910. If there is a match, the process flows to step 4912 to store the potential trend.

A trend may be stored as a potential trend when there is a correlating data point, but not enough data to activate it as an active trend in the system. At step 4914, the system receives a plurality of additional test results from a plurality of addition conducted tests. The process then flows to decision block 4916 to determine whether additional instances of the potential trend stored in step 4912 is in an amount above a threshold. Such a threshold may be a certain number, a percentage of all patients related to the trend demographic or other data point (such as all female patients of a particular ethnicity), or other threshold types. If instance of the potential trend is not above the threshold, the process flows back to step 4914 to receive more test results. If at decision block 4916 it is determined that the instances of the potential trend is above the threshold, the process flows to step 4918. At step 4918, the system changes the status of the potential trend to an active trend.

Figure 50:
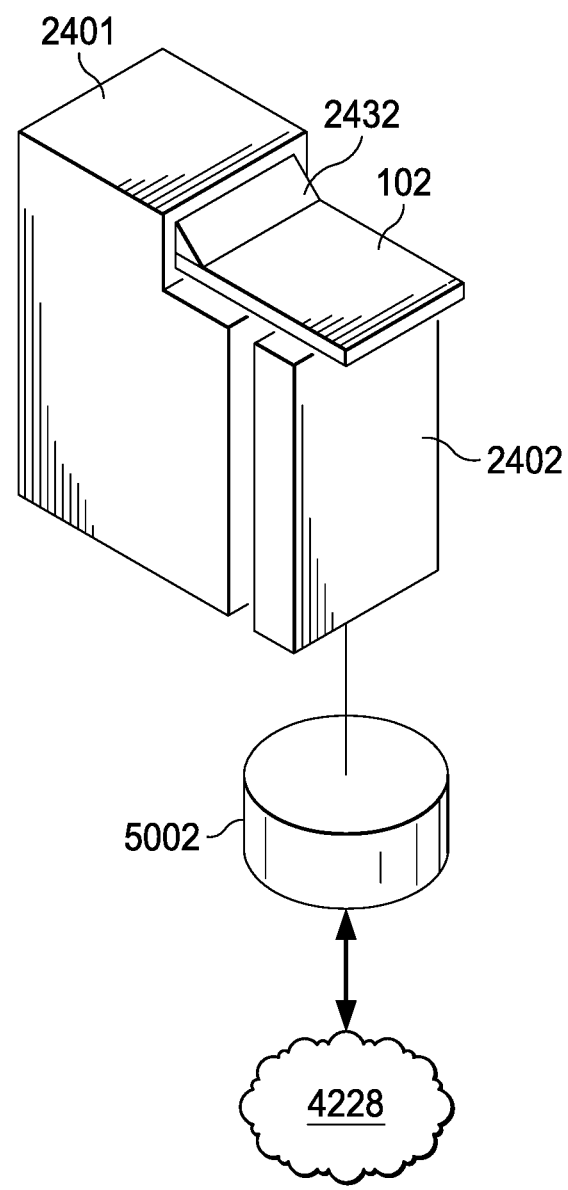
FIG. 50 illustrates a diagrammatic view of a medical voice-activated assistant device configured to connect to a medical testing device or mobile device in accordance with various embodiments of the present disclosure.

Referring now to FIG. 50, there is illustrated a diagrammatic view of a medical voice-activated assistant device 5002 configured to connect to a medical testing device or mobile device. In some embodiments such as that shown in FIG. 50, the voice-activated assistant device 5002 is connected to the smartphone 2402 to receive test results from the smartphone 2402 that are being collected by the smartphone 2402 from the multinode instrument 2401 and the microfluidic chip 102. In some embodiments, the voice-activated assistant device 5002 may connect directly the multinode instrument 2401, or in some embodiments may connect to a microfluidic chip described in the various embodiments disclosed herein.

The voice-activated assistant device 5002 may connect to the network 4228 in order to provide connectivity between the voice-activated assistant device 5002 and the entities 4202-4226 illustrated in FIG. 42. This allows the voice-activated assistant device 5002 to access patient records, research materials, studies, and papers, university studies, locate trending data, find recommended procedures or treatments for medical conditions, copy research to patient and/or doctor files, suggest additional tests, document test results, document procedures performed, and connect to other outside resources. The voice-activated assistant device 5002 may provide a plurality of information to a doctor working with the voice-activated assistant device 5002 to provide the doctor with valuable, up-to-date, information on current medical procedures, treatments, breakthroughs, drug interactions and side effects, and other information useful in treating the patient.

Figure 51:
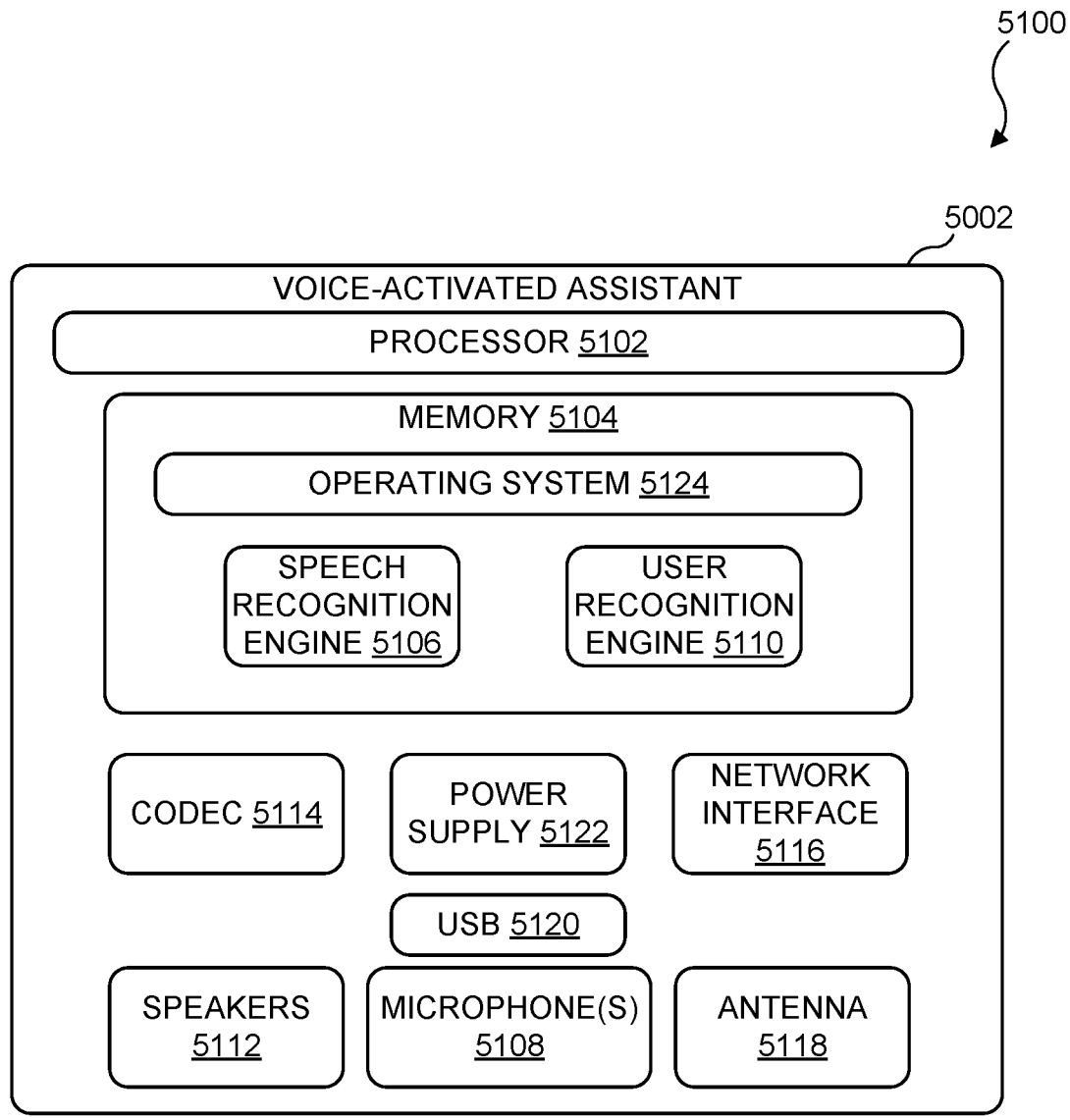
FIG. 51 illustrates a diagrammatic view of a voice-activated assistant device architecture of a voice-activated assistant device, in accordance with various embodiments of the present disclosure.

Referring now to FIG. 51, there is illustrated a voice-activated assistant device architecture 5100 of the voice-activated assistant device 5002, in accordance with various embodiments of the present disclosure. The voice-activated assistant device 5002 includes a processor 5102 and a memory 5104. The memory 5104 may store or access a speech recognition engine 5106. The processor 5102 may include multiple processors or be a multi-core processor. The speech recognition engine 5106 may perform speech recognition operations on audio or voice data captured by one or more microphones 5108, such as commands spoken by a physician, nurse, physician's assistant, lab technician, or other personnel. A user recognition engine 5110 may determine whether a user's voice being detected is authorized to use the device in some embodiments. In some embodiments, the user recognition engine 5110 may also be trained to recognize a user's voice in order to assist with speech recognition operations.

In response to commands received and speech captured and recognized by the voice-activated assistant device 5002, the voice-activated assistant device 5002 may perform actions based on the commands or speech captured. For example, "recite the side effects of acetaminophen," may cause the voice-activated assistant device 5002 to audibly recite the side effects to the user via the speakers 5112. Predefined commands may also be set up to enable quick actions to be performed, such as "call assistant" immediately calling the user's assistant via cellular or data communication. In some embodiments, another voice-activated assistant device 5200 may be set up near the user's assistant to alert the user's assistant. In some embodiments, speech recognition may not be performed locally. Rather, the voice-activated assistant device 5002 may transmit the captured audio to a remote entity such as the centralized system 4202 to allow the remote entity to perform the speech recognition and transmit the appropriate command and audible response to the voice-activated assistant device 5002. In some embodiments, a codec 5114 may be coupled to the one or more microphones 5108 and speakers 5112 to encode and/or decode audio signals. The codec 5114 may also convert audio data from analog to digital format. Thus, the user may interact with the voice-activated assistant device 5002 by speech alone, without the use of input/output devices such a keyboard or display.

The voice-activated assistant device 5002 may connect to the network 4228 via a network interface 5116. The network interface 5116 may include wired connections, or wireless connections such as Bluetooth, RF, cellular technologies, etc. The voice-activated assistant device 5002 may also include an antenna 5118 that may be connected to the network interface 5116 to facilitate a wireless connection the network 4228. The voice-activated assistant device 5002 may also include a wired interface 5120 such as a USB interface to allow other devices to be connected to the voice-activated assistant device 5002. A power supply 5122 may also be included to distribute power to the various components of the voice-activated assistant device 5002.

Several modules such as instructions, datastores, etc. may be stored within the memory 5104, and configured to execute on the processor 5102, such as an operating system 5124. The operating system 5124 may be configured to manage hardware and services such as wireless, USB, or codec services, for the benefit of other modules within the voice-activated assistant device 5002.

Figure 52:
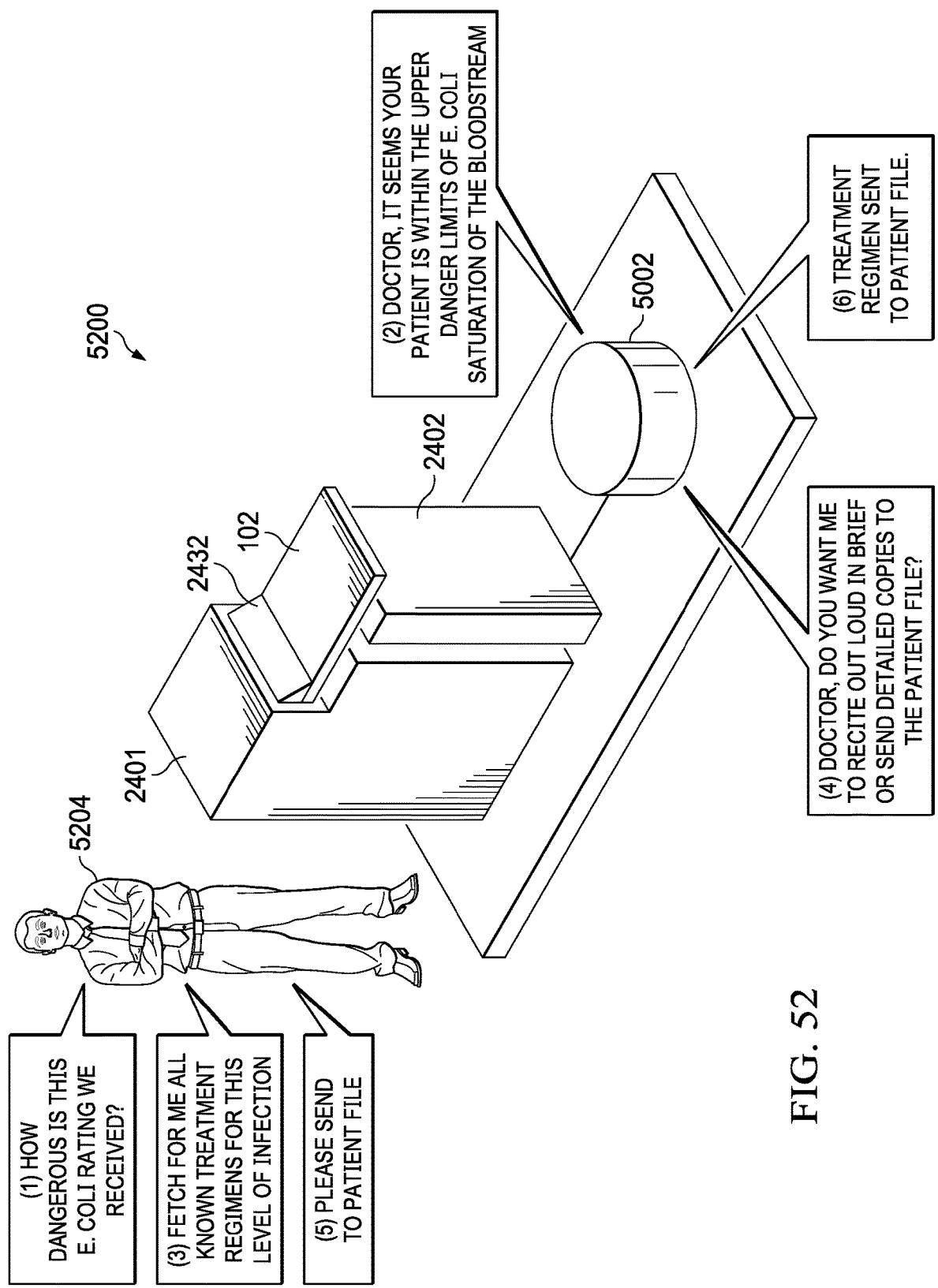
FIG. 52 illustrates a diagrammatic view of a voice-activated request process in accordance with various embodiments of the present disclosure.

Referring now to FIG. 52, there is illustrated a diagrammatic view of a voice-activated request process 5200. There is illustrated the voice-activated assistant device 5002 positioned on a surface such as a table or counter, with and coupled to a medical testing device 5202 such as those described herein. It will be understood that in some embodiments, the voice-activated assistant device 5002 may be placed elsewhere, such as mounted on a wall, in a cabinet, in a wall or in the ceiling, etc. It will also be understood that multiple voice-activated assistant devices may be setup. For example, there may be one set up near the testing device as shown in FIG. 52, while another voice-activated assistant device is installed in the a doctor's personal office, so that the doctor can ask receive test results and ask questions of the voice-activated assistant device set up in the doctor's personal office without having to be near the voice-activated assistant device set up near the medical testing device. Voice-activated assistant devices may be set up all over a facility in this way, and may even be set up in a residential location such as the doctor's home to allow the doctor access to patient and medical information while away from the office. The voice-activated assistant devices may be set up to communicate with each other over the network 4228, over a private local network, or other configurations.

Upon conclusion of a medical test using the medical testing device 5202, a physician 5204, or other person such as a lab technician, nurse, physician's assistant, pharmacist, etc., may request additional information from the voice-activated assistant device 5002. It will be understood that this is but one example of an interaction with the voice-activated assistant device 5002. At step (1), the physician 5204 asks the voice-activated assistant device 5002, "how dangerous is this *E. coli* rating we received?" In this example, at step (2), the voice-activated assistant device 5002 replies, "doctor, it seems your patient is within the upper danger limits of *E. coli* saturation of the bloodstream." At step (3), the physician 5204 issues the command, "fetch for me all known treatment regimens for this level of infection." At step (4), the voice-activated assistant device 5002, after, in some embodiments, sending out a request over the network 4228 for the treatment regimen information, replies, "doctor, do you want me to recite out loud in brief or send detailed copies to the patient file?" At step (5), the physician 5204 states, "please send to the patient file." At step (6), the voice-activated assistant device 5002 may issue a confirmation, stating, "treatment regimen sent to patient file."

Figure 53:
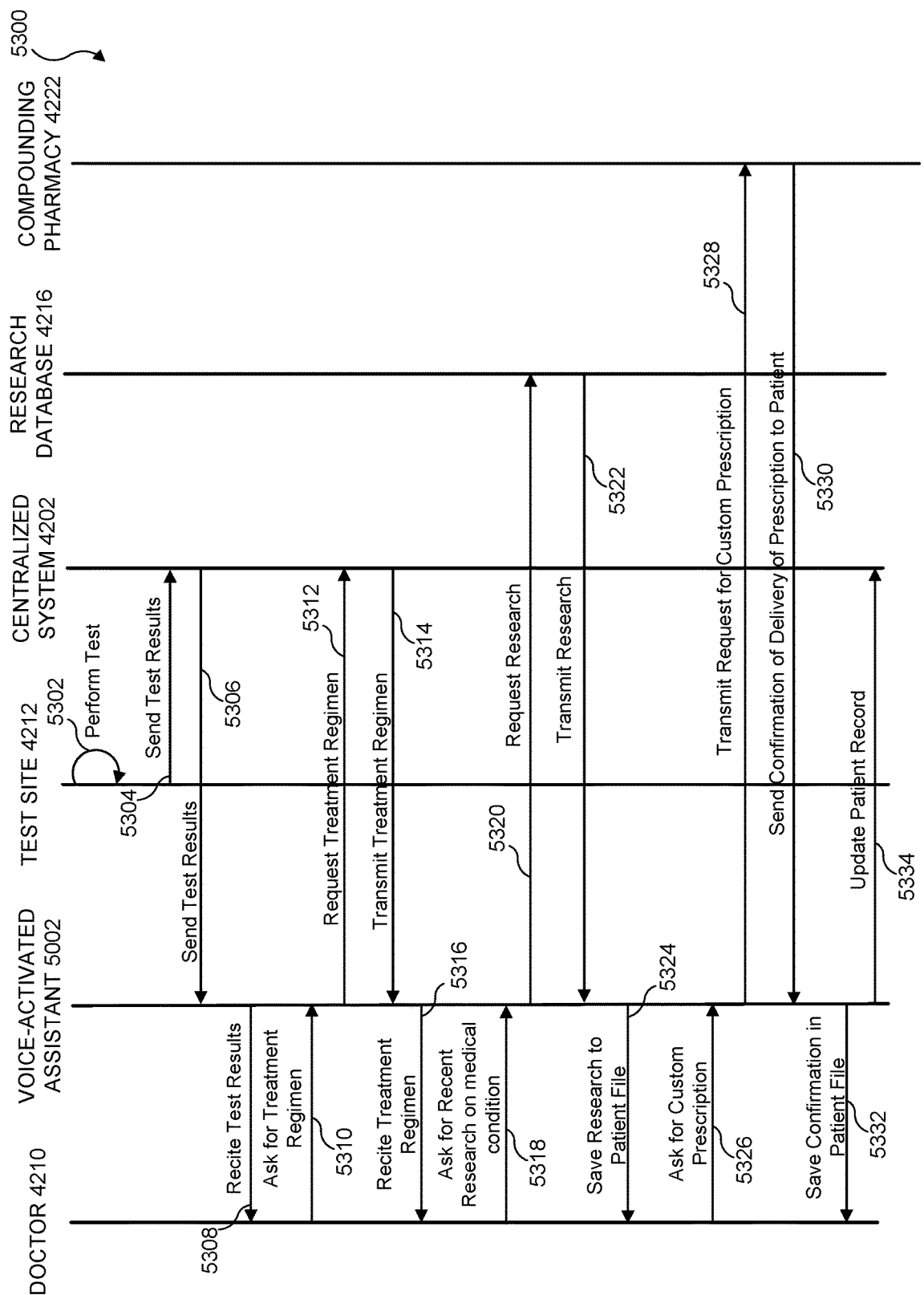
FIG. 53 illustrates a sequence diagram a process of a voice-activated assistant device interaction with various outside resources in accordance with various embodiments of the present disclosure.

Referring now to FIG. 53, there is illustrated a sequence diagram of a process 5300 of a voice-activated assistant device 5002 interaction with various outside resources. At step S302, a test is performed at a test site 4212. The test site may be a lab, a doctor's office, a hospital, or any other location where a medical test is conducted. At step S304, the test site transmits the test results to the centralized system 4202. In some embodiments, the test results may be sent directly to the doctor's office 4210 or the voice-activated assistant 5002. At step S306, the centralized system 4202 transmits the test results to the voice-activated assistant 5002. At step S308, the voice-activated assistant 5002 recites the test results to the doctor or other medical professional. At step S310, the doctor asks the voice-activated assistant 5002 for a treatment regimen in accordance with the test results. At step S312, the voice-activated assistant 5002 transmits a request for a treatment regimen from the centralized system 4202. At step S314, the centralized system 4202 transmits the treatment regimen information to the voice-activated assistant 5002. At step S316, the voice-activated assistant 5002 recites the treatment regimen information to the doctor.

The voice-activated assistant 5002 may also in some embodiments allow a medical professional to request medical research on a topic. This allows for the medical professional to seek additional education from recent studies or other information that may assist the medical professional in treating the patient. As illustrated in FIG. 42, research database and other entities may be connected to the centralized system 4202 over the network 4228 and thus also to the voice-activated assistant 5002.

At step S318, the doctor asks the voice-activated assistant 5002 for recent research on the medical condition related to the test results. At step S320, the voice-activated assistant 5002 requests pertinent research from a research database 4216. At step S322, the research database 4216 transmits the requested research to the voice-activated assistant 5002. At step S324, the voice-activated assistant 5002 saves the research to the patient file. In some embodiments, the voice-activated assistant 5002 may recite information from the research. In some embodiments, the voice-activated assistant 5002 may ask the doctor whether the research should be recited, saved to a patient file, emailed to someone such as the patient or a physician's assistant, or otherwise stored or accessed. The voice-activated assistant 5002 may also be used to send information to the patient, such as recipes for achieving a better diet (such as if the patient has diabetes), specifics on the treatment plan, research and information concerning the patient's condition, etc. The voice-activated assistant 5002 may also connect to a voice-activated device owned by the patient to relay information to the patient. In this way, the voice-activated assistant 5002 can provide not only medical information and interconnectivity to medical systems, but may also provide patients, health, lifestyle, and quality of life information and assistance.

At step S326, the doctor may ask the voice-activated assistant 5002 to request a custom prescription. Based on the test results, the treatment regimen, and the research accumulated by the voice-activated assistant 5002 and the doctor, the doctor may determine that a typical prescription will not be as effective in treating the patient. The doctor may thus request that a custom prescription requiring one or more drugs combined together at particular dosages. At step S328, the voice-activated assistant 5002 transmits a request for the custom prescription from a compounding pharmacy 4222. At step S330, the compounding pharmacy may send a confirmation to the voice-activated assistant 5002 that the patient has received the custom prescription. The voice-activated assistant 5002 may at 5332 save the confirmation to the patient file, recite to the doctor that the prescription was received by the patient, or perform other actions such as notifying the physician's assistant. At step S334, the voice-activated assistant 5002 may update the patient record at the centralized system 4202 with all steps taken during the process 5300 in relation to the patient, such as the treatment regimen enacted, the prescriptions written for the patient, an overall health report, etc. It will be understood that multiple update steps similar to step S334 may occur throughout process 5300 to ensure the centralized system 4202 is consistently up-to-date.

It will be understood that the voice-activated assistant 5002 may be connected to all entities illustrated in FIG. 42, and may allow for the sharing of information between doctor's offices, labs, hospitals, researchers, universities, etc. The voice-activated assistant 5002 may retrieve data, studies, papers, etc., from any or all of various primary research types such as basic research including theoretical research (such as method development (physics, chemistry biology, bioinformatics, biometrics, psychology), analytical measurement procedure, imaging procedure, biometric procedure, and test development assessment procedure), and applied research (such as animal studies, cell studies, genetic engineering/gene sequencing, biochemistry, material development, and genetic studies). Primary research retrieved may also include clinical research such as experimental research (including clinical studies and phase I-IV studies) and observational research (including therapy studies, prognostic studies, diagnostic studies, observational studies with drugs, secondary data analysis, case series, and single case reports). Primary research retrieved may also include epidemiological research such as experimental epidemiological research (including intervention studies, field studies, and group studies) and observational epidemiological research (including cohort studies— prospective and historical, case control studies, cross-sectional studies, ecological studies, and monitoring).

Secondary research may also be retrieved such as meta-analysis, reviews, systematic research, and simple (narrative) research. Additional research and information may be retrieved such as information and research from and regarding: the Consolidated Standards of Reporting Trials, pharmaceutical research, FDA information, translational research, medicine research, pre-clinical research, drug and pipelines, medical device research, human genome project information, biomedical research, medical ethics, research ethics, regulations and guidelines, immunology, neurology, treatment research, prevention, diagnostic, screening, quality of life, genetic studies, cancer research, medical technology, evidence-based medicine, aging population issues, behavior/mental, child health, community benefit/community health needs, economics, policy, literacy, public health services and systems, behavoristic factors, school health policies and practices, U.S. Census data.

Additional research may be retrieved from disconnected resources such as the FDA, Wellcome Trust, National Institute of Health, the Bill and Melinda Gates Foundation, the National Health and Medical Research Council, information subject to the 1980 Bayh-Dole Act, the Public Health Database, the OVID database, the National Library of Medicine, the MedLine database, the PubMed database, Cochran databases, the International Pharmaceutical Abstracts, EmBase, the Education Resources Information Center (ERIC), EBSCO databases, CINAHL databases, NHS Evidence database, Trip Medical Database, Royal Marsden Manual of Clinical Nursing, the Scopus database, Health Business Elite, Health Management Consortium, Allied and Complimentary Medicine database, PEDro (physiotherapy evidence database), Occupational Therapy database, Health Services Research Info Central (HSRIC) database, Domestic Violence database, Rural Health database, Center for Disease Control (CDC), Big Cities Health Coalition, Comparable State Data on the Affordable Care Act, Homelessness Data Exchange, Medicare/Medicaid databases, Medicare provider database, National Program for Cancer Registries, National Cancer Institute, Surveillance, Epidemiology, and End Results Program, Substance Abuse and Mental Health Services Admin database, State Health Systems Performance database, Council of State Governments and Performance database, CMS Central Repository, Data.gov, health.data.gov, Open Trials FDA database, Rochester Epidemiology Project, Social Sciences Data Archive, Administration for Community Living, Agency for Healthcare Research and Quality (AHRQ) database, AHRQ Innovations database, AHRQ Kids database, CDC Wonder, Childstats.gov, and Chronic Conditions Data Warehouse.

Figure 54:
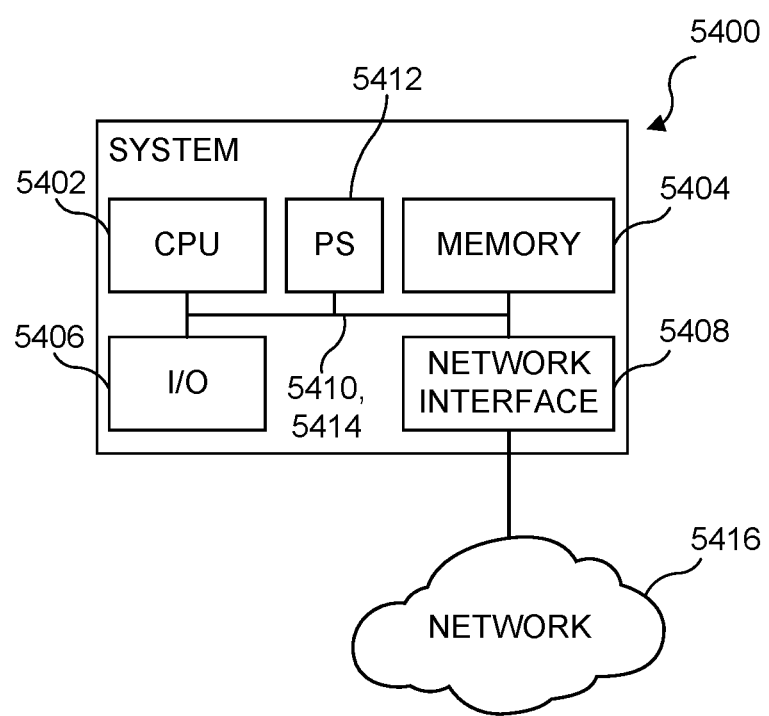
FIG. 54 illustrates a diagrammatic view of one embodiment of a system device that may be used within the environment described herein.

Research and other information may be retrieved from a variety of sources, which include, but are not limited to, the following:

Referring to FIG. 54, one embodiment of a system device 5400 is illustrated. The system device 5400 is one possible example of a device used by an end user, and/or a device such as the mobile device, the server 4202, or other devices. Components of the system device 5400 may also be used in the voice-activated assistant device 5002. Embodiments include cellular telephones (including smart phones), personal digital assistants (PDAs), netbooks, tablets, laptops, desktops, workstations, telepresence consoles, and any other computing device that can communicate with another computing device using a wireless and/or wireline communication link. Such communications may be direct (e.g., via a peer-to-peer network, an ad hoc network, or using a direct connection), indirect, such as through a server or other proxy (e.g., in a client-server model), or may use a combination of direct and indirect communications. It is understood that the device may be implemented in many different ways and by many different types of systems, and may be customized as needed to operate within a particular environment.

The system 5400 may include a controller (e.g., a central processing unit ("CPU")) 5402, a memory unit 5404, an input/output ("I/O") device 5406, and a network interface 5408. The components 5402, 5404, 5406, and 5408 are interconnected by a transport system (e.g., a bus) 5410. A power supply (PS) 5412 may provide power to components of the computer system 5400, such as the CPU 5402 and memory unit 5404, via a power system 5414 (which is illustrated with the transport system 5410 but may be different). It is understood that the system 5400 may be differently configured and that each of the listed components may actually represent several different components. For example, the CPU 5402 may actually represent a multi-processor or a distributed processing system; the memory unit 5404 may include different levels of cache memory, main memory, hard disks, and remote storage locations; the I/O device 5406 may include monitors, keyboards, and the like; and the network interface 5408 may include one or more network cards providing one or more wired and/or wireless connections to a network 5416. Therefore, a wide range of flexibility is anticipated in the configuration of the computer system 5400.

The system 5400 may use any operating system (or multiple operating systems), including various versions of operating systems provided by Microsoft (such as WINDOWS), Apple (such as Mac OS X), UNIX, and LINUX, and may include operating systems specifically developed for handheld devices, personal computers, servers, and embedded devices depending on the use of the system 5400. The operating system, as well as other instructions, may be stored in the memory unit 5404 and executed by the processor 5402. For example, the memory unit 5404 may include instructions for performing some or all of the methods described herein.

It should be understood that the drawings and detailed description herein are to be regarded in an illustrative rather than a restrictive manner, and are not intended to be limiting to the particular forms and examples disclosed. On the contrary, included are any further modifications, changes, rearrangements, substitutions, alternatives, design choices, and embodiments apparent to those of ordinary skill in the art, without departing from the spirit and scope hereof, as defined by the following claims. Thus, it is intended that the following claims be interpreted to embrace all such further modifications, changes, rearrangements, substitutions, alternatives, design choices, and embodiments.

What is claimed is:

1. An artificial intelligence response system, the system comprising:
   a centralized system including associated therewith a trained database, a trends engine, and a plurality of patient records;
   a plurality of interconnected entities connected over a network to the centralized system; and
   a voice-activated assistant device connected over the network to the centralized system and to the interconnected entities, the voice-activated assistant device including a memory operatively coupled to at least one processor;
   a speech recognition engine contained within the memory for identifying a voice command from a medical professional;
   a user recognition engine within the memory for determining if the voice command comes from an authorized individual;
   wherein the at least one processor is configured to:
      receive test results pertaining to a patient from the centralized system;
      receive a first voice command to request a treatment regimen from the medical professional;
      determine if the medical professional is the authorized individual responsive to the first voice command using the user recognition engine;
      request a treatment regimen for a patient from the centralized system in response to the first voice command if the medical professional is determined to be the authorized individual;
      receive a second voice command from the medical professional to update medical records for the patient;
      determine if the medical professional is the authorized individual responsive to the second voice command using the user recognition engine;
      update the medical records for the patient in response to the second voice command if the medical professional is determined to be the authorized individual; and
      performing one or more actions related to treating the patient.

2. The system of claim 1, wherein the voice command from the medical professional includes a request for research information on a particular medical condition.

3. The system of claim 2, wherein the at least one processor is configured to request additional medical information in response to the voice command by requesting the research information on the particular medical condition from a research database disposed over a network.

4. The system of claim 3, wherein the at least one processor is configured to save the research information on the particular medical condition to a patient file.

5. The system of claim 1, wherein the one or more actions related to treating the patient include
   requesting a prescription based on the treatment regimen.

6. The system of claim 5, wherein, to request the prescription based on the treatment regimen, the at least one processor is further configured to:
   receive a voice data request for the prescription;
   transmit a prescription request to a compounding pharmacy system over a network; and
   receive a confirmation of receipt of the prescription request from the compounding pharmacy system.

7. The system of claim 6, wherein, to update a patient record, the at least one processor is further configured to store the confirmation of receipt of the prescription request from the compounding pharmacy system in association with the patient record.

8. The system of claim 5, wherein, to update a patient record, the at least one processor is further configured to store, in association with the patient record, at least one of the treatment regimen or an overall health report.

9. The system of claim 1, wherein the at least one processor is further configured to determine, via the trends engine, that a potential trend is found in an amount that is above a threshold.

10. The system of claim 9, wherein the threshold is at least one of a certain number of instances of a condition or a percentage of patients related to a trend demographic.

11. A method of an artificial intelligence response system, the method comprising:
   receiving, by a voice-activated assistant device, test results pertaining to a patient from a centralized system, wherein the voice-activated assistant device is connected over a network to the centralized system and to a plurality of interconnected entities, and wherein the centralized system includes associated therewith a trained database, a trends engine, and a plurality of patient records;
   receiving, by the voice-activated assistance device, a first voice command to request a treatment regimen from a medical professional;
   determining, by the voice-activated assistance device, if the medical professional is an authorized individual responsive to the first voice command using a user recognition engine;
   requesting, by the voice-activated assistant device, a treatment regimen for a patient from the centralized system in response to the first voice command if the medical professional is determined to be the authorized individual;
   receiving, by the voice-activated assistant device, a second voice command from the medical professional to update medical records for the patient;
   determining, by the voice-activated assistant device, if the medical professional is the authorized individual responsive to the second voice command;
   updating, by the voice-activated assistant device, the medical records for the patient in response to the second voice command if the medical professional is determined to be the authorized individual; and
   performing, by the voice-activated assistant device, one or more actions related to treating the patient.

12. The method of claim 11, wherein the voice command from the medical professional includes a request for research information on a particular medical condition.

13. The method of claim 12, wherein requesting the additional medical information in response to the voice command includes requesting, by the voice-activated assistant device, the research information on the particular medical condition from a research database disposed over a network.

14. The method of claim 13, further comprising saving, by the voice-activated assistant device, the research information on the particular medical condition to a patient file.

15. The method of claim 11, wherein the one or more actions related to treating the patient include at least one of:
   requesting, by the voice-activated assistant device, a prescription based on the treatment regimen; or
   updating, by the voice-activated assistant device, a patient record.

16. The method of claim 15, wherein requesting the prescription based on the treatment regimen includes:
   receiving, by the voice-activated assistant device, a voice data request for the prescription;
   transmitting, by the voice-activated assistant device, a prescription request to a compounding pharmacy system over a network; and
   receiving, by the voice-activated assistant device, a confirmation of receipt of the prescription request from the compounding pharmacy system.

17. The method of claim 16, wherein updating the patient record includes storing, by the voice-activated assistant device, the confirmation of receipt of the prescription request from the compounding pharmacy system in association with the patient record.

18. The method of claim 15, wherein updating the patient record include storing, by the voice-activated assistant device, in association with the patient record, at least one of the treatment regimen or an overall health report.

19. The method of claim 11, further comprising determining, by the voice-activated assistant device via the trends engine, that a potential trend is found in an amount that is above a threshold.

20. The method of claim 19, wherein the threshold is at least one of a certain number of instances of a condition or a percentage of patients related to a trend demographic.

* * * * *